(12) United States Patent
Klein

(10) Patent No.: US 10,322,083 B2
(45) Date of Patent: *Jun. 18, 2019

(54) TUMESCENT DRUG DELIVERY

(71) Applicant: Jeffrey Alan Klein, San Juan Capistrano, CA (US)

(72) Inventor: Jeffrey Alan Klein, San Juan Capistrano, CA (US)

(73) Assignee: HK Pharma, San Clemente, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 15/489,225

(22) Filed: Apr. 17, 2017

(65) Prior Publication Data

US 2017/0216198 A1 Aug. 3, 2017

Related U.S. Application Data

(63) Continuation of application No. 14/578,147, filed on Dec. 19, 2014, now Pat. No. 9,623,030, which is a continuation of application No. 13/512,880, filed on May 30, 2012, now Pat. No. 8,957,060, which is a continuation-in-part of application No. PCT/US2010/058440, filed on Nov. 30, 2010, said application No. 14/578,147 is a continuation-in-part of application No. 13/189,775, filed on Jul. 25, 2011, now Pat. No. 8,506,551, which is a continuation of application No. 11/800,355, filed on May 4, 2007, now Pat. No. 8,105,310, which is a continuation-in-part of application No. 10/877,566, filed on Jun. 25, 2004, now abandoned.

(60) Provisional application No. 61/265,286, filed on Nov. 30, 2009.

(51) Int. Cl.
| | |
|---|---|
| *A61K 9/00* | (2006.01) |
| *A61M 5/14* | (2006.01) |
| *A61K 45/06* | (2006.01) |
| *A61M 25/00* | (2006.01) |
| *A61K 31/137* | (2006.01) |
| *A61K 31/167* | (2006.01) |
| *A61K 31/546* | (2006.01) |

(52) U.S. Cl.
CPC .......... *A61K 9/0021* (2013.01); *A61K 9/0019* (2013.01); *A61K 31/137* (2013.01); *A61K 31/167* (2013.01); *A61K 31/546* (2013.01); *A61K 45/06* (2013.01); *A61M 5/14* (2013.01); *A61M 25/007* (2013.01)

(58) Field of Classification Search
CPC combination set(s) only.
See application file for complete search history.

(56) References Cited

U.S. PATENT DOCUMENTS

| | | |
|---|---|---|
| 2,708,437 A | 5/1955 | Hutchins |
| 3,082,805 A | 3/1963 | Royce |
| 3,732,858 A | 5/1973 | Banko |
| 3,734,099 A | 5/1973 | Bender |
| 3,764,099 A | 5/1973 | Bender et al. |
| 3,927,672 A | 12/1975 | Garcia |
| 3,955,579 A | 5/1976 | Bridgman |
| 3,994,297 A | 11/1976 | Kopf |
| 4,167,944 A | 9/1979 | Banko |
| 4,203,444 A | 5/1980 | Bonnell et al. |
| 4,210,670 A | 7/1980 | Cooke |
| 4,311,140 A | 1/1982 | Bridgman |
| 4,314,560 A | 2/1982 | Helfgott et al. |
| 4,402,684 A | 9/1983 | Jessup |
| 4,405,322 A | 9/1983 | Jessup |
| 4,460,360 A | 7/1984 | Finegold |
| 4,487,600 A | 12/1984 | Brownlie et al. |
| 4,530,356 A | 7/1985 | Helfgott et al. |
| 4,536,180 A | 8/1985 | Johnson |
| 4,577,629 A | 3/1986 | Martinez |
| 4,586,921 A | 5/1986 | Berson |
| 4,589,414 A | 5/1986 | Yoshida et al. |
| 4,713,053 A | 12/1987 | Lee |
| 4,735,605 A | 4/1988 | Swartz |

(Continued)

FOREIGN PATENT DOCUMENTS

FR  2 777 462 A1  10/1999

OTHER PUBLICATIONS

Gordley, Seminars in Plastic surgery/vol. 20, No. 4, 2006.*
NHS Lanarkshire, 2011, p. 1-30.*
Bussolin (Anesthesiology, 2003, 99, 1371-5).*
NCI, 2008 (Year: 2000).*
NHS, 2013 (Year: 2013).*
Gurney, British J of Cancer, 2002 (Year: 2002).*
Wasil, The Oncologist, 2005 (Year: 2005).*
NIH-Cancer Institute, 2018 (Year: 2018).*
Borg et al., "Potential Anti-Thrombotic Effects of Local Anesthetics Due to Their Inhibition of Platelet Aggregation," *Acta Anaesthesiologica Scandinavica*, vol. 29(7), pp. 739-742 (1985).

(Continued)

*Primary Examiner* — Umamaheswari Ramachandran
(74) *Attorney, Agent, or Firm* — Knobbe, Martens, Olson & Bear LLP

(57) ABSTRACT

A method of subcutaneous delivery of a drug or a therapeutic agent to a subject comprising administering to said subject a mass of fluid of a tumescent composition comprising: (a) the drug or the therapeutic agent; (b) a vasoconstrictor; and (c) a pharmaceutically acceptable carrier, wherein a relatively large total amount of the drug is isolated from systemic circulation in the subject because only drug in an outer boundary of the mass of fluid is the available for absorption, whereas a portion of the drug located within a central portion of the mass of fluid is virtually isolated from the systemic circulation by virtue of profound capillary vasoconstriction, wherein epinephrine-induced vasoconstriction dramatically slows systemic absorption of the drug or therapeutic agent, and wherein the mass of fluid is a reservoir that delivers the drug or the therapeutic agent to the subject with pharmacokinetics that are analogous to a slow-release oral tablet or a slow constant intravenous (IV) Infusion.

19 Claims, 13 Drawing Sheets

(56) References Cited

U.S. PATENT DOCUMENTS

| | | |
|---|---|---|
| 4,775,365 A | 10/1988 | Swartz |
| 4,784,649 A | 11/1988 | Imonti et al. |
| 4,790,830 A | 12/1988 | Hamacher |
| 4,815,462 A | 3/1989 | Clark |
| 4,850,354 A | 7/1989 | McGurk-Burleson et al. |
| 4,886,491 A | 12/1989 | Parisi et al. |
| 4,919,129 A | 4/1990 | Weber, Jr. |
| 4,925,450 A | 5/1990 | Imonti et al. |
| 4,932,935 A | 6/1990 | Swartz |
| 4,938,743 A | 7/1990 | Lee |
| 5,052,999 A | 10/1991 | Klein |
| 5,112,302 A | 5/1992 | Cucin |
| 5,181,907 A | 1/1993 | Becker |
| 5,186,714 A | 2/1993 | Boudreault et al. |
| 5,203,769 A | 4/1993 | Clement et al. |
| 5,236,414 A | 8/1993 | Takasu |
| 5,242,386 A | 9/1993 | Holzer |
| 5,244,458 A | 9/1993 | Takasu |
| 5,286,253 A | 2/1994 | Fucci |
| 5,295,980 A | 3/1994 | Ersek |
| 5,314,407 A | 5/1994 | Auth |
| 5,348,535 A | 9/1994 | Cucin |
| 5,352,194 A | 10/1994 | Greco |
| 5,446,070 A | 8/1995 | Mantelle |
| 5,447,493 A | 9/1995 | Blugerman et al. |
| 5,453,088 A | 9/1995 | Boudewiin et al. |
| 5,472,416 A | 12/1995 | Blugerman et al. |
| 5,489,291 A | 2/1996 | Wiley |
| 5,514,086 A | 5/1996 | Parisi |
| 5,643,198 A | 7/1997 | Cucin |
| 5,655,544 A | 8/1997 | Johnson |
| 5,725,495 A | 3/1998 | Strukel et al. |
| 5,795,323 A | 8/1998 | Cucin |
| 5,800,407 A | 9/1998 | Eldor |
| 5,807,282 A | 9/1998 | Fowler |
| 5,817,050 A | 10/1998 | Klein |
| 5,884,631 A | 3/1999 | Silberg |
| 5,947,988 A | 9/1999 | Smith |
| 5,968,008 A | 10/1999 | Grams |
| 6,020,196 A | 2/2000 | Hu et al. |
| 6,039,048 A | 3/2000 | Silberg |
| 6,071,260 A | 6/2000 | Halverson |
| 6,102,885 A | 8/2000 | Bass |
| 6,113,569 A | 9/2000 | Becker |
| 6,129,701 A | 10/2000 | Cimino |
| 6,162,202 A | 12/2000 | Sicurelli et al. |
| 6,168,611 B1 | 1/2001 | Rizvi |
| 6,238,355 B1 | 5/2001 | Daum |
| 6,238,373 B1 | 5/2001 | de la Torre et al. |
| 6,280,424 B1 | 8/2001 | Chang et al. |
| 6,319,230 B1 | 11/2001 | Palasis et al. |
| 6,375,648 B1 | 4/2002 | Edelman |
| 6,428,499 B1 | 8/2002 | Halverson |
| 6,436,116 B1 | 8/2002 | Spitz et al. |
| 6,475,196 B1 | 11/2002 | Vachon |
| 6,503,263 B2 | 1/2003 | Adams |
| 6,524,300 B2 | 2/2003 | Meglin |
| 6,592,559 B1 | 7/2003 | Pakter et al. |
| 6,613,026 B1 | 9/2003 | Palasis et al. |
| 6,685,666 B1 | 2/2004 | Fontenot |
| 6,692,473 B2 | 2/2004 | St. Cyr et al. |
| 6,706,026 B1 | 3/2004 | Goldstein et al. |
| 6,916,292 B2 | 7/2005 | Morawski et al. |
| 6,969,371 B2 | 11/2005 | Palasis et al. |
| 6,969,373 B2 | 11/2005 | Schwartz et al. |
| 7,004,923 B2 | 2/2006 | Deniega et al. |
| 7,056,315 B2 | 6/2006 | Gonon |
| 7,410,480 B2 | 8/2008 | Muni et al. |
| 7,465,291 B2 | 12/2008 | Massengale |
| 2002/0095124 A1 | 7/2002 | Palasis et al. |
| 2002/0123723 A1 | 9/2002 | Sorenson et al. |
| 2003/0009132 A1 | 1/2003 | Schwartz et al. |
| 2003/0032942 A1 | 2/2003 | Theeuwes et al. |
| 2004/0076671 A1 | 4/2004 | Tippett |
| 2004/0215143 A1 | 10/2004 | Brady et al. |
| 2004/0236286 A1 | 11/2004 | Klein |
| 2004/0236307 A1 | 11/2004 | Klein |
| 2004/0236313 A1 | 11/2004 | Klein |
| 2005/0086072 A1 | 4/2005 | Fox, Jr. et al. |
| 2005/0287134 A1 | 12/2005 | Klein |
| 2006/0259111 A1 | 11/2006 | Peterson |
| 2007/0213688 A1 | 9/2007 | Klein |
| 2007/0255238 A1 | 11/2007 | Cochrum et al. |
| 2008/0108971 A1 | 5/2008 | Klein |
| 2008/0287866 A1 | 11/2008 | Heller |
| 2009/0177184 A1 | 7/2009 | Christensen et al. |
| 2010/0069827 A1 | 3/2010 | Silberg |

OTHER PUBLICATIONS

Chen, G. et al. 1999 "Study on the effect of Lidocaine on the in vitro aggregation function of platelets" Chin J Intern Med 38(1): 780-781.

Coleman, et al. 2000 "When one liter does not equal 1000 milliliters: Implications for the tumescent technique" *The American Society for Dermatologic Surgery*; 26; 1024-1028.

Cui, S. 2000 "Rational use of cephalosporins" *Modern Medicine Health* 16(5): 489-490.

Extended European Search Report issued in European Patent Application No. 10834060.5, dated Apr. 26, 2013.

Goodman, et al. 2001 "The pharmacological basis of therapeutics" *Chemotherapy of Microbial Diseases*, 10 edition, 1206 and 1210.

Goodman, et al. 2001 "The pharmacological basis of therapeutics" *Chemotherapy of Microbial Diseases*, 10 edition, p. 1656.

International Search Report dated Feb. 8, 2011, received in connection with PCT/US10/58440.

Klein, J.A. 1987 "The Tumescent Technique for Lipo-Suction Surgery" *The American Journal of Cosmetic Surgery* 4(4): 263-267.

Klein, J.A. 1993 "Tumescent Technique for Local Anesthesia Improves Safety in Large-Volume Liposuction" Plast Reconstr Surg 92: 1085-1098.

Klein, J.A., 1990 "Tumescent Technique for Regional Anesthesia Permits Lidocaine Doses of 35 mg/kg for Liposuction" J Dermatol Surg Oncol 16(3): 248-263.

Klein, J.A. 1990 "The Tumescent Technique Anesthesia and Modified Liposuction Technique" *Dermatologic Clinics* 8(3): 425-437.

Neil-Dwyer, et al. 2001 "Tumescent steroid infiltration to reduce postoperative swelling after craniofacial surgery" *British Journal of Plastic Surgery* 54; 565-569.

Office Action in related Chinese Application No. 201080062364.2, dated May 7, 2014.

Office Action in related European Application No. 10 83 4060, dated Oct. 16, 2014.

Office Action in related Chinese Application No. 201080062364.2, dated Nov. 17, 2014.

Patient-Controlled Transdermal Fentanyl Hydrochloride vs. Intravenous Morphine Pump for Postoperative Pain, JAMA, 291(11), Mar. 17, 2004, 9 pages.

Qiao, C. and Baxian, Y. 1999 "The effects of different anesthetic techniques on haemorheaology in patients undergoing total hip replacement" J Clin Anesthesiology 15(1): 11-13.

Reese, R.E. and Betts, R.F. 1996 "Chapter 28B—Prophylactic Antibiotics" in *Practical Approach to Infectious Diseases*, 4th ed.

SeromaCath Wound Drainage System pamphlet and instructions for use, Greer Medical, Inc., on the World-Wide-Web at greermedical.com (2 pages). Dated May 17, 2001.

SeroVac II and SeroVac Series drainage products, Axiom Medical, Inc., on the World-Wide-Web at axiommed.com/Medical-Products/Plastics/SeroVac-.html (1 page). Dated Sep. 9, 2013.

SeromaCath Wound Drainage System, on the World-Wide-Web at greermedical.com/Html/product1.htm (4 pages). Dated Aug. 14, 2003.

Viscusi, E.R. et al. 2004 "Patient-Controlled Transdermal Fentanyl Hydrochloride vs. Intravenous Morphine Pump for Postoperative Pain" *JAMA* 291(11):1333-1341.

Zhu W. 1993 "Clinical application of Cephalosporin antibiotics" *Chinese Journal of Rural Medicine* 21(12):30-32.

\* cited by examiner

TUMESCENT DRUG DELIVERY

BACKGROUND OF THE INVENTION

Field of the Invention

The present embodiments relate to compositions, kits and methods of use of a solution comprising an anesthetic component, a vasoconstrictor component, and an antibiotic component for use in medical procedures.

Description of the Related Art

Many medical procedures require infiltration of fluids, such as a local anesthetic. For example, liposuction may be performed entirely by tumescent local anesthesia which was invented by Jeffrey A. Klein. Dr. Klein first published the description of tumescent local anesthesia to perform liposuction in 1987 (Klein J A. The tumescent technique for liposuction surgery. J Am Acad Cosmetic Surg 4:263-267, 1987). The tumescent technique was invented in order to eliminate the dangers of liposuction surgery under general anesthesia and the associated excessive bleeding. With proper technique, tumescent infiltration permits liposuction totally by local anesthesia with virtually no surgical blood loss.

One method of infiltration of local anesthetic is via a blunt tipped infiltration cannula. Infiltrators are known as sprinkler-tip or Klein™ needle infiltrators. These cannulae are constructed out of a rigid stainless steel and have one or more apertures, which are typically round or oval, and are distributed about the distal end of the cannula. The apertures are distributed over about 15% to 25% or less than 5.0 cm. of the distal end of the cannula needle. These traditional infiltration cannulae are intended to be inserted through a small incision in the patient's skin and then moved in and out through the subcutaneous tissue while a dilute solution of local anesthetic (or other pharmaceutical solution) is ejected through the distal apertures. Since the cannula needle is moved in and out, only the distal end (e.g., about 15% to 25%) of the cannula needle may have apertures. Otherwise, fluid may squirt out of the apertures and onto medical professionals when the cannula needle is moved out too much. Such infiltrators typically have a blunt tip and require the placement of a small hole (made by a one mm skin-biopsy punch or a small surgical blade) through which the blunt tipped cannula can be passed. Unfortunately, the piston-like in and out motion of the cannula causes the patient discomfort.

Another type of infiltration cannula is the sharp tipped tumescent infiltration cannula which is available as 1) a single long sharp needle similar to a spinal needle and 2) a group of short sharp hypodermic needles each connected by separate plastic tube to a manifold that distributes Tumescent Local Anesthesia (TLA) solution. The first type of needle is inserted into subcutaneous fat and infiltration proceeds while the needle is continuously moved in and out along paths that radiate from the skin puncture site. A targeted area is eventually anesthetized after multiple skin punctures. The second type, the group of short sharp needles, consists of a group of individual hypodermic needles each attached to an individual IV extension tube, which are in turn connected to a multi port manifold which connected to a reservoir (IV bag) of tumescent fluid. These sharp-tipped tumescent infiltration devices have been associated with puncture-injury to deeper tissues such as the lungs causing pneumothorax or intra-abdominal viscera causing peritonitis.

In summary, there are two causes of pain associated with the blunt and sharp tipped infiltration cannulae. One significant cause of pain is a continuous in and out motion of the cannula as it moves through non-anesthetized tissue. In order to deliver tumescent anesthetic solution throughout an entire compartment of subcutaneous fat, the anesthetist must move the cannula with a continuous to and fro reciprocating motion, and repeatedly change directions. Each advance of the cannula through fat causes discomfort and pain. The second cause of pain is associated with an excessively rapid distention of tissue resulting from a high rate of fluid injection into a relatively small volume of tissue via limited number of holes on the distal tip of the infiltration cannula. Ironically, the pain associated with each of these two factors often necessitates the use of narcotic analgesia, IV sedation, or general anesthesia in order to infiltrate local anesthesia. The present embodiments eliminate or greatly reduce these two sources of pain.

Another method of fluid insertion is via a peripherally inserted central catheter, also called a PICC line comprising an elongate plastic tube that is placed inside a vein of the patient. PICC lines are typically used for procedures requiring delivery of fluids over a prolonged period of time. For example, a PICC line may be used when a patient needs to receive intravenous (IV) fluids, such as medication or nutrients over a prolonged period of time, such as a week or more.

The On-Q® Pain Management System marketed by I-Flow® Corporation employs a flexible plastic or silicone catheter system for continuously providing local anesthetic. This system provides prolonged local anesthesia by means of an elastomeric (elastic container) device that continuously infiltrates a solution of local anesthesia over many hours. The On-Q® device comprises a long soft flexible tube with many small holes arranged along a significant portion of the tube. The On-Q® device is designed to be initially positioned within a surgical wound at the time of surgery. After the surgical wound is closed, the On-Q® device permits slow steady infiltration of a local anesthetic solution into the wound, thereby attenuating post-operative pain. The On-Q® device cannot be inserted through a tiny hole in the skin when there is a need. Therefore the On-Q device cannot achieve infiltration of local anesthesia and prevent post-operative pain in a preemptive fashion. In some versions of the On-Q device, as described in U.S. Pat. No. 7,465,291 (Massengale), a long flexible multi-holed catheter is inserted subcutaneously using an introducer wire and an introducer catheter. This device requires a large sterile field (an area upon which to lay all of the sterile devices used during the insertion process), a complicated insertion protocol, and either general anesthesia or careful pre-insertion infiltration of local anesthesia. Further, the Massengale device is not intend for or capable of being repeatedly inserted in and out of different areas of subcutaneous tissue; it cannot be inserted quickly by untrained personnel in-the-field and far from a sophisticated medical facility. It has been shown that preemptive local anesthesia in the form of peripheral nerve blocks, can prevent nocioception by the central nervous system (CNS) during general anesthesia, and thereby prevent chronic post-operative pain syndromes similar to "phantom-limb syndrome." Thus there is a need for a simple device that can permit the direct percutaneous insertion of a multi-holed infiltration cannula into subcutaneous tissue for the localized delivery of medications such as local anesthetics, chemotherapeutic agents, or crystalloids for parenteral hydration. There is also a need for a device that can easily provide localized fluid resuscitation to burn victims whereby fluid is infiltrated into the subcutaneous tissue directly subjacent to burned skin.

Traditional techniques for subcutaneous injection of local anesthetic solutions (e.g. peripheral nerve blocks) use a high-concentration/low-volume of local anesthetic. This is associated with a rapid systemic absorption of the local anesthetic. In order to achieve a prolonged local anesthetic effect, the traditional techniques for using local anesthetics necessitate either frequent repeated injections or slow continuous subcutaneous infusion of the local anesthetic. As described above, repeated injections or piston-like movement of the cannula causes patient discomfort. Slow continuous infiltration may not be desirable in certain situations. Furthermore, continuous infiltrations restrict patient movement for extended periods of time which also cause the patient discomfort. Thus, there is a need for a system for infiltration of a local anesthetic into intact subcutaneous tissue (not necessarily into peri-incisional tissue) which decreases patient discomfort preemptively, and allows prolonged local anesthesia either by rapid (less than 10 to 15 minutes) bolus injections, extended infiltration (e.g. over intervals ranging from 15 minutes to several hours) or continuous slow infiltration over many hours to days. Furthermore there is a need for a device that can provide preemptive local anesthesia before a surgical wound is created. There is also a need for a percutaneously-insertable infiltration cannula, with applications that are unrelated to the delivery of local anesthesia, which can be easily inserted by rescuers with minimal clinical skill or training. One example is the need for a cannula that permits emergency fluid resuscitation in situations where an IV cannot be established such as nighttime military combat conditions where using a flash light to establish an IV access would be extremely dangerous. Another example is the need to provide emergency fluid resuscitation to large numbers of patients in acute epidemic diarrhea (dehydration) associated with biological warfare, or mass-trauma situations such as a natural disaster (earth quake) or terrorist attack. There is also a need for a device that can easily provide localized fluid resuscitation to burn victims whereby fluid is infiltrated into the subcutaneous tissue directly subjacent to burned skin.

Other types of devices for delivering fluid to a patient exist in the prior art. For example, U.S. Pat. Pub. No. 2003/0009132 (Schwartz et al.) is directed to a micro-intravascular (never extra-vascular) catheter for infusing milliliter quantities of drugs for the lysis of intravascular blood clots (i.e., a micro target). Another embodiment of the Schwartz device is intended to improve the precision and safety of intra-myocardial delivery of micro-liter volumes of fluid for biologic gene therapy based angiogenesis.

Unfortunately, the Schwartz device requires a sterile high tech hospital environment and demands fluoroscopy and ultrasound guidance. The Schwartz device requires a highly trained, experienced and skilled medical professional to operate. In particular, the Schwartz infiltration catheter is defined by its obligatory guidewire and intravascular target. The intravascular insertion of the catheter via the guidewire is a complex procedure that requires significant clinical training, experience and skill. Specifically, it involves 1) preparation with a sterile surgical field, 2) making a skin incision and inserting an introducing catheter having coaxial stylet into the targeted vessel, 3) removing the stylet, 4) inserting the guidewire through the introducing catheter and into the vessel, 5) withdrawing the introducing catheter from the vessel without disturbing the intravascular location of the guidewire, 6) slipping the distal tip of the infiltration catheter over the proximal end of the guidewire, and advancing the infiltration catheter over the considerable length of the guidewire through the skin and into the intraluminal space of the targeted vessel, 7) withdrawing the guidewire and attaching the proximal end of the infiltration catheter to a source of the therapeutic fluid to be delivered into the targeted vessel. This insertion procedure is so specialized that a majority of physicians do not have the requisite expertise to qualify for hospital privileges for inserting an intravascular catheter using a guidewire. Locating a clotted blood vessel and inserting the Schwartz catheter into the vessel requires ultrasound guidance.

As understood, an important feature of the Schwartz device is the shape, size, direction and pattern of the holes on the infiltration cannula. As stated in paragraph 15 of the Schwartz disclosure, "there is a need for an injection device that gives control over the concentration, pattern, and location of the deposition of an injectate." The Schwartz device is intended to improve directional control over the direction of injection of minute volumes of injectate.

The Schwartz device appears to be specifically designed to avoid vascular compression. For the small needle embodiment of Schwartz, vascular compression resulting from injecting excessive volume of drug into myocardium may precipitate infarction or arrhythmia. Likewise, for the long cannula embodiment of Schwartz vascular compression appears to be contraindicated. The goal of infusing fluid into a vessel containing a blood clot is to open the vessel, and not compress it.

The Schwartz device also appears to be incapable of large volume (e.g., multi liter) subcutaneous infiltration. The long plastic Schwartz catheter appears to be specifically intended for intravascular use. Moreover, Schwartz cannula cannot have holes distributed along 100% of its entire length based on a contention that such situation will lead to a contradictory situation. If the Schwartz device does have holes along its entire length then either the entire length of the cannula would have to be positioned inside a vessel (unlikely without attaching the cannula proximally to another catheter in which case the bulky attachment mechanism would have to be passed through the wall of the vessel) or else some of the holes would have an extravascular location (unlikely because the therapeutic fluid would either leak onto the patient's skin or extravasate into the perivascular and subcutaneous tissues). In either case, the potential for serious adverse effects would be significant.

Moreover, the Schwartz device does not appear to be capable of being reciprocated in and out of the subcutaneous tissue of the patient to locally anesthetize an entire compartment.

In summary, the Schwartz infiltrator is intended for 1) intravascular insertion which demands a complex guidewire procedure involving several steps, 2) intravascular drug delivery (for lysis of blood clots) or intra myocardial injections, 3) injection of a miniscule volume (micro liters) of drug.

Another type of device for delivering fluid to a patient is described in U.S. Pat. No. 6,524,300, issued to Meglin. Similar to the Schwartz device, the Meglin device appears to be an intravascular device intended to inject a "medical agent into the target lumen of the body." (see Col. 2, lns. 41-48). Meglin is specifically intended to be inserted intraluminally into "a lumen of a blood vessel or another cavity within a patient's body." (see Col. 1, lns. 14-19). This is precisely opposite the goal of a tumescent infiltration cannula. A tumescent infiltration cannula is intended to deliver drugs to the subcutaneous space which excludes the vascular space and cavitary space. As such, the Meglin device appears to be specifically designed to avoid vascular compression and to not induce vasoconstriction. An important aspect of the Meglin device appears to be the size and density of the apertures to control the rate of flow of fluidic medication. Moreover, it appears that the medical professional utilizing the Meglin device requires a great deal of training, expertise and education based on a contention that the infusion segment of the device is located intravascularly by locating a radiopaque marker band with a fluoroscopy.

Another type of device for delivering fluid to a patient is described in U.S. Pat. No. 6,375,648, issued to Edelman, et al. Similar to prior art blunt or sharp tipped infiltration cannulae, the apertures are restricted to the distal 25% of the cannula. The reason is that otherwise, the fluidic medication would squirt out of the apertures and contaminate the operating room. Col. 2, lns. 22-25 states that "once within the tissue of a patient a treatment solution may be infused into the tissue by working the cannula 20 through the fat tissue of the patient." As understood, the Edelman device suffers from the same deficiencies discussed above in relation to the blunt or sharp tipped infiltration cannulae. The Edelman cannula is reciprocated in and out of the subcutaneous tissue, and thus, causes pain or discomfort to the patient. Moreover, the only novel aspect of Edelman appears to be the cannula's Teflon coating.

Surgical site infections are a significant source of postoperative morbidity and mortality. They account for 17% of all hospital acquired infections, require prolonged hospital stays and contribute substantially to health care costs. The incidence of surgical site infection is a function of the type of surgical procedure, the surgeon, and the hospital. The risk of surgical site infection is significantly associated with a number of factors including anesthetic risk scores, wound class and duration of surgery.

The true incidence of surgical site infection is probably higher than what has been reported in the literature. The primary surgical team is often not aware of incisional infections diagnosed after hospital discharge. Patients who had surgical site infection diagnosed after discharge require substantially more outpatient visits, emergency visits, radiology services and home healthcare services. A study published in 2004 found such infections cost $6,200 per patient for home care expenses associated with wound care. The major sources of infection are microorganisms on the patient's skin. A number of preoperative skin care techniques have been used to limit concentrations of bacteria at the surgical site, including antiseptic preparations, adhesive barrier drapes, topical antibiotics, hair removal and hand hygiene.

Antimicrobial prophylaxis with intravenous (IV) antibiotics is currently the most important clinical modality for preventing surgical site infection. The consensus recommendation for antimicrobial prophylaxis is for antimicrobial agents to be given as an IV infusion of antibiotics administered within the first 60 minutes before surgical incision and that prophylactic antimicrobial agents be discontinued within 24 hours of the end of surgery.

Recent Center for Disease Control (CDC) guidelines for antimicrobial prophylaxis do not mention preoperative perilesional infiltration of antibiotics (http://www.cdc.gov/ncidod/dhgp/pdf/guidelines/SSI.pdt). A recent review of surgical site infections only discussed intravenous (IV) delivery of prophylactic antibiotics. The possibility of preoperative peri-incisional infiltration to prevent SSI was not considered.

Several studies of surgical site infection in the 1980's compared the effectiveness of antimicrobial prophylaxis by IV infusion or by peri-incisional infiltration. A 1981 study of the incidence of wound infection among 405 abdominal surgery patients found no significant difference between 1 gm of cephaloridine given intravenously or intra incisional at the end of the surgery. Following this trial, IV antibiotics at the induction of anesthesia became standard practice.

An IV infusion of fluid is a common medical procedure to treat patients. Unfortunately, an IV infusion is associated with an inherent expense, difficulty and risk. There are also unfortunately times when an IV line cannot be established in the patient. By way of example and not limitation, the patient may be burned such that a vein of the patient cannot be located to establish an IV access. The patient may have been traumatized in such a way that will not allow a doctor to perform an IV cut down procedure. Additionally, the patient may be very obese such that the vein of the patient is difficult to locate. In other situations, occurring in remote locations where a trained medical professional is not available to establish the IV, such as the international space station or on an airplane. Currently, there does not appear to be any in-flight capability for treating an acute traumatic injury on a plane or on the space shuttle. If the pilot or astronaut survives the immediate effects of an explosion, burn, or decompression injury, or if there is an acute non-traumatic medical illness, it is assumed that the victim must return to terra firma for any significant therapeutic intervention such as providing systemic fluid replacement. Other situations include a mass casualty situation where there are insufficient numbers of trained medical professionals compared to the number of victims/patients, etc.

Other methods of delivering a drug to a patient other than IV administration may be oral delivery of the drug. Unfortunately, oral delivery of the drug results in inconsistent absorption of the drug into the gastrointestinal tract. The drug may alternatively be delivered via periodic intramuscular injections. Unfortunately, the fluidic drug serum may have varying levels of concentration at each of the periodic injections.

There are also problems with systemic administration of antibiotics, whether by IV or oral administration, as a prophylactic or treatment method for surgical site infection or other acute infections. For example, systemic levels in the blood may be high enough to cause significant side effects, while antibiotic levels at the surgical site or site of infections may not be sufficient to prevent or treat infection. One dose-related problem frequently reported by patients receiving systemic antibiotic administration is gastrointestinal toxicity. Systemic administration of antibiotics can kill off the protective natural flora in the gut, resulting in conditions favorable for the overgrowth of certain antibiotic-resistant pathogens, specifically *Clostridium difficile*. This can result in a condition known as *Clostridium difficile* colitis. It follows that there exists a need to improve the function of antibiotic prophylaxis at the surgical site while reducing the unwanted side effects of systemic antibiotic administration.

SUMMARY OF THE INVENTION

A method is disclosed for reducing surgical site infection in a patient during a medical procedure. The method comprises administering subcutaneously a tumescent antibiotic composition, comprising: (a) an antibiotic component; (b)

an anesthetic component; (c) a vasoconstrictor component; and (d) a pharmaceutically acceptable carrier.

In preferred embodiments of the method, the anesthetic component comprises lidocaine. The concentration of lidocaine is preferably approximately 500 mg to 1,000 mg per L of solution.

In preferred embodiments of the method, the vasoconstrictor component comprises epinephrine. The concentration of epinephrine is preferably approximately 0.5 to 1 mg per L.

In preferred embodiments of the method, the antibiotic component comprises cefazolin. In a variation to the method, the antibiotic component may comprise a mixture of two or more antibiotics.

In other embodiments of the method, the composition may further comprise an anti-inflammatory agent.

In preferred embodiments, the medical procedure is liposuction. In certain embodiments, the medical procedure may comprise removal of subcutaneous tissue from the patient. In other embodiments, the medical procedure may be selected from a mastectomy, fluid resuscitation, administration of antibiotics, and administration of anesthesia.

A method of preventing thromboembolism in a patient during a medical procedure is also disclosed. The method comprises administering into the subcutaneous fat compartment of the patient a composition comprising an antibiotic component, a vasoconstrictor component and an anesthetic component, in a pharmaceutically acceptable carrier.

A tumescent antibiotic composition is disclosed in accordance with certain preferred embodiments. The composition comprises: (a) an antibiotic component; (b) an anesthetic component; (c) a vasoconstrictor component; and (d) a pharmaceutically acceptable solvent.

The antibiotic component of the composition preferably comprises cefazolin at a concentration of between 250 to 1000 mg per liter of solvent. Alternatively, the antibiotic component may comprise a mixture of two or more antibiotics.

The anesthetic component of the composition preferably comprises lidocaine at a concentration of between 400 to 1200 mg per liter of solvent.

The vasoconstrictor component of the composition preferably comprises epinephrine at a concentration of 0.4 to 1.2 mg per liter of solvent. Alternatively, the vasoconstrictor component may comprise a mixture of epinephrine and one or more vasoconstrictors other than epinephrine.

The pH of the composition is preferably acidic.

In some embodiments, bicarbonate at a concentration of 5 to 25 mEq per liter of solvent is included.

In some embodiments, the pharmaceutically acceptable solvent may comprise a saline solution, lactated Ringer's solution, or Hartmann's solution.

In some embodiments, the solvent may further comprise a perflourocarbon.

In a further variation, the composition may also comprise an anti-inflammatory agent.

A kit for tumescent antibiotic delivery is disclosed in accordance with certain preferred embodiments. The kit may comprise a bag prefilled with a composition comprising: (a) an antibiotic component; (b) an anesthetic component; (c) a vasoconstrictor component; and (d) a pharmaceutically acceptable solvent, and a tumescent infiltration cannula. Preferably, the bag is visually distinguishable from IV bags. In some embodiments, the bag and/or the composition therein comprises a distinctive color. In some embodiments, the bag further comprises a printed warning against IV use. In some embodiments, the kit further comprises a non-luer connector.

A method of providing antibiotic treatment to an acute infection is also disclosed. The method comprises administering into the subcutaneous fat compartment a solution comprising an antibiotic component and a vasoconstrictor component. The antibiotic component preferably comprises cefazolin. The solution may also comprise an anesthetic component.

In preferred embodiments of the method, the vasoconstrictor component comprises epinephrine.

In a variation to the method, the solution may further comprise an anti-inflammatory agent.

In some embodiments the solution may further comprise an anti-inflammatory agent.

Some embodiments relate to a method of treating cancer, comprising administering subcutaneously a tumescent composition, comprising: a chemotherapy component; a vasoconstrictor component; and a solvent.

DETAILED DESCRIPTION OF THE INVENTION

Figure 1:
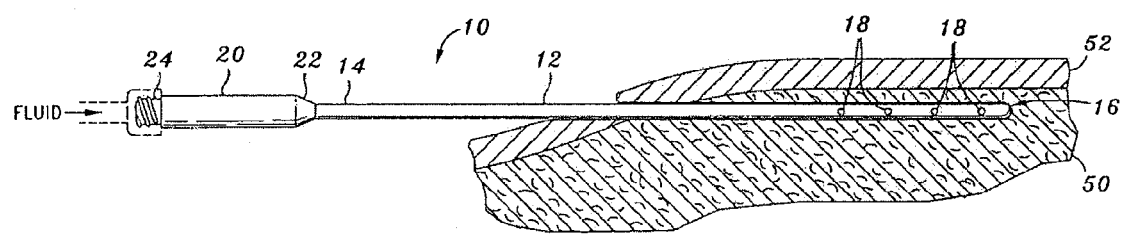
FIG. 1 is a side elevation view of a stainless steel infiltration cannula with a closed tip shown inserted in subcutaneous tissue shown in partial cross section.

As described in further detail below, the present embodiments take advantage of the tumescent technique in order to provide intermittent or continuous, brief or prolonged multi-liter infiltration of local anesthetic, physiologic fluid, antibiotics or other therapeutic solution with a significant decrease in patient discomfort due to the elimination of the piston-like in and out motion of the cannula. Once the cannula is positioned in place, there is no need to repeatedly move the cannula in and out through the tissue in order to deliver the fluid to a wide area. Using the tumescent technique and stainless steel versions of several embodiments, the time needed in order to complete the infiltration of a targeted anatomic area is reduced to nearly half of the time required when using traditional cannulae. The device and method of the present embodiments can use multiple (e.g., two or more) infiltration cannulae simultaneously. While one cannula is actively dispersing tumescent fluid into the subcutaneous tissue, the surgeon can reposition a second infiltration cannula. This allows the infiltration process to proceed without interruption, whereas prior art techniques of infiltration must be ceased each time the cannula is withdrawn from the skin and re-inserted into another direction.

The flexible plastic cannula version of the present embodiments provides a means for relatively rapid fluid resuscitation in emergency situations such as when establishing an intravenous (IV) access is not feasible. A large volume of a tumescent crystalloid solution to treat intravascular fluid deficit may be delivered subcutaneously when an intravascular (IV) line cannot be started for fluid replacement. (e.g., remote area, obese patient, burn/trauma victim, unavailable trained medical professional, etc.). As a further embodiment, rapid systemic absorption of physiologic saline can be achieved by adding a vasodilator drug to saline and using the tumescent technique to deliver the solution into subcutaneous tissue. For example, in the setting of overwhelming mass casualties where there is no hope or expectation of trained clinical personnel being available, the ability of untrained first-responders to provide immediate fluid resuscitation could save many lives. When a disaster causes an overwhelming number of trauma or burn victims, or when a cholera epidemic leaves victims with life-threatening dysentery and dehydration, it is unlikely that there will be sufficient trained personnel to start an IV line for IV fluid resuscitation. In such a setting, anyone (e.g., adult of average intelligence with minimal clinical training), perhaps even a victim himself, could simply insert one or more disposable plastic infiltration cannulae directly through the skin on the thigh(s) and into subcutaneous tissue and attach an IV bag and then allow the force of gravity to propel the fluid into the subcutaneous space in a tumescent fashion. The resulting systemic absorption and redistribution into the intracellular and intravascular compartments could be life-saving. This emergency resuscitation procedure can involve the combination of 1) the plastic-catheter embodiment and 2) absorption kinetics of tumescent fluid delivered to subcutaneous tissue.

The flexible cannula may also have important applications in treating a wounded soldier in night-time combat conditions when establishing an IV access in total darkness is nearly impossible or using a flashlight might attract enemy fire. The flexible cannula may similarly have important applications in other areas of use such as treating mass-casualty victims suffering hypovolemia as a result of epidemic infections, biologic warfare, or trauma such as explosions, burns or radiation exposure. The flexible cannula similarly has applications in surgical patients wherein the surgeon can provide localized pre-operative preemptive analgesia and simultaneously provide tumescent delivery of a prophylactic dose of an antibiotic aimed precisely at tissues targeted for surgical intervention.

The tumescent technique was discovered by Jeffrey Alan Klein, M.D. (the present applicant) in 1985. Dr. Klein first published a description of the tumescent technique in 1987 when he described the use of dilute lidocaine and epinephrine to permit liposuction totally by local anesthesia. The technique for tumescent local anesthesia is well known in dermatologic and plastic surgery literature. A detailed description of the tumescent technique has not been published in anesthesiology literature, and therefore, the unique benefits of the tumescent technique are not recognized by anesthesiologists.

In several embodiments, the tumescent technique comprises a drug delivery system that takes advantage of a recently discovered reservoir effect of injecting a relatively large volume of relatively dilute solution of a drug into the subcutaneous tissue.

Several embodiments take advantage of the tumescent reservoir phenomenon for one of its important applications. After a large volume (e.g., multi liter) of fluid containing dilute epinephrine is injected into subcutaneous tissue, the epinephrine-induced vasoconstriction dramatically slows the systemic absorption of the fluid and minimizes surgical blood loss. In effect, this large volume of subcutaneous fluid behaves in a fashion that is analogous to the behavior of a slow-release tablet in the stomach after oral ingestion. Although there is a relatively large total amount of drug in the patient's body, the drug is isolated from the systemic circulation because only the drug on the outer boundary of the mass of drug is the available for absorption, whereas the portion of the drug located within the central portion of the mass of fluid is virtually isolated from the systemic circulation by virtue of profound capillary vasoconstriction. In contrast, when the tumescent fluid does not contain epinephrine there is no clinically significant vasoconstriction after tumescent infiltration, and the tumescent fluid is absorbed relatively rapidly. This has important clinical applications in situations where patients are hypovolemic or dehydrated and unable to be given fluids by mouth or intravenously. The tumescent technique permits rapid systemic hydration by direct subcutaneous or intramuscular injection of a large volume of fluid through a multi-fenestrated infiltration cannula described in this invention.

A technique known as hypodermoclysis involves the slow and continuous infiltration of fluid subcutaneously using a type of steel hypodermic needle, known as a butterfly needle, having a single distal aperture in order to provide fluid to patients who cannot be given fluids by mouth and for whom an IV access cannot be established, such as in the treatment of infants, or cancer patients. The technique of hypodermoclysis is typically used to deliver relatively small volumes of fluid, for example an adult might receive 70 ml per hour. At this small hourly volume hypodermoclysis is not an efficient method for the rapid systemic delivery of fluid in emergency situations that might require two to four liters per hour. The reason is that when using a cannula with only a single distal aperture, the local interstitial fluid pressure increases rapidly immediately adjacent to the single aperture as fluid infiltrates locally, which in turn dramatically slows the rate of subsequent fluid flow into the area. In contrast, the multiple apertures formed along the length of the cannula as described in the present invention, distribute the fluid throughout a much larger volume tissue before there can be a sufficient increase in the interstitial fluid to decrease the rate of additional infiltration. Also, the amount of pain is reduced because the rate of fluid flow through each of the apertures is less than the rate of fluid flow through the single aperture at the distal end. Further more, it is common practice to infiltrate the tumescent fluid into the subcutaneous space under augmented external pressure provided by an external peristaltic pump specifically designed for tumescent infiltration. By way of example and not limitation, a preferred suitable peristaltic infiltration pump is described in pending U.S. patent application Ser. No. 10/811,733, filed Mar. 29, 2004, entitled INFILTRATION PUMP HAVING INSULATED ROLLERS AND PROGRAMMABLE FOOT PEDAL, the disclosure of which is expressly incorporated herein by reference.

The peristaltic pump provides a sufficient degree of pressure to easily overcome the localized increased interstitial pressure associated with the local effects of a tumescent infiltration. On the other hand, in situations where a peristaltic infiltration pump is not available, such as in remote locations without any available electrical power, the present invention still permits relatively rapid tumescent infiltration by virtue of the multiple holes distributed along the length of the flexible cannula. Furthermore, external hydrostatic pressure can be applied to the fluid flowing into the flexible cannula from the fluid reservoir by means of gravitational force derived from elevating the reservoir one to two or more meters above the patient. When using gravity to augment the flow of tumescent fluid, the infiltration process can be continuous or intermittent. In exemplary embodiments, the intermittent injections are administered at intervals ranging from every few minutes to eight to twelve hours or more.

With the tumescent technique for local anesthesia, a large volume of dilute solution of local anesthesia and epinephrine is injected into the subcutaneous space resulting in a large bolus (or interstitial reservoir) of solution. The profound vasoconstrictive effect (shrinking of the capillaries) caused by the dilute epinephrine, produces a dramatic delay in the systemic absorption of the local anesthetic, which prolongs the anesthetic effects of tumescent anesthesia for eight to sixteen times longer than traditional techniques.

Figure 2:
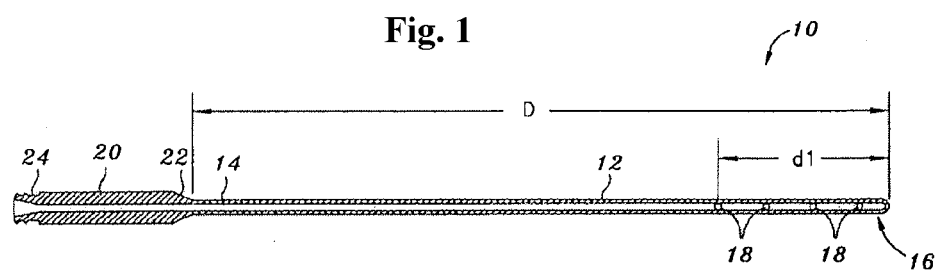
FIG. 2 is a section view of the infiltration cannula shown in FIG. 1.
Figure 3:
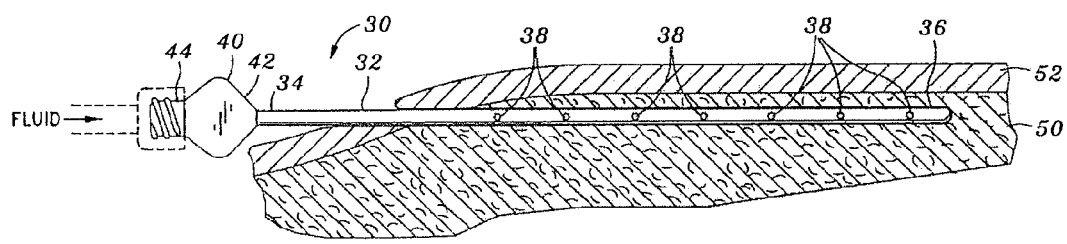
FIG. 3 is a side elevation view of a plastic infiltration cannula with a closed tip shown inserted in subcutaneous tissue shown in partial cross section.
Figure 4:
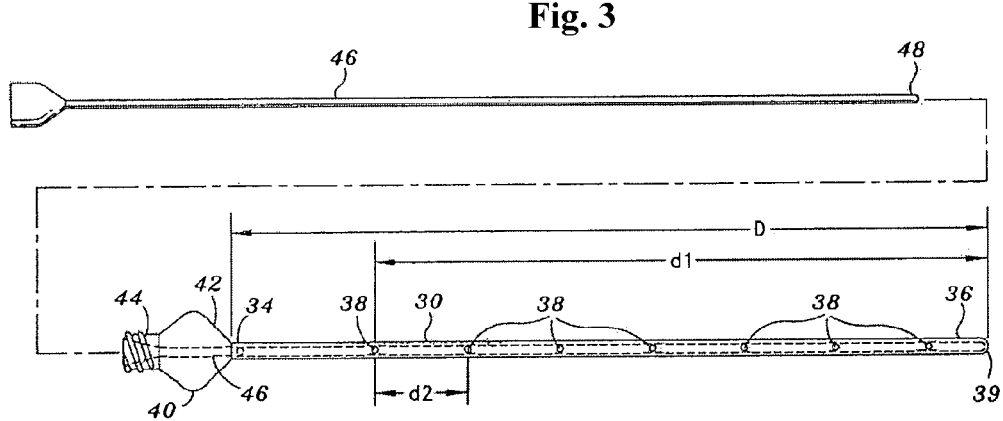
FIG. 4 is an exploded view of the infiltration cannula shown in FIG. 3 with a closed end.
Figure 6:
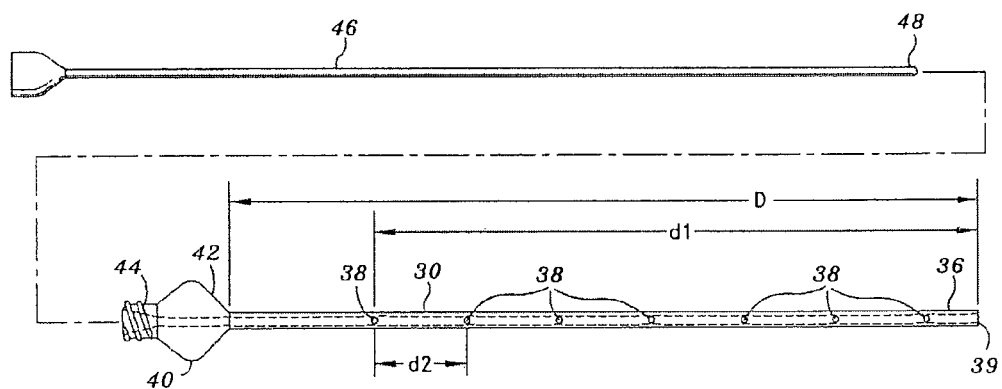
FIG. 6 is an exploded side elevation view of a plastic infiltration cannula through which a stylet can be inserted with an open end.

Referring now to the drawings wherein the showings are for purposes of illustrating preferred embodiments of the present invention only, and not for purposes of limiting the same, FIGS. 1 and 2 illustrate a stainless steel (reusable) infiltration cannula 10 and FIGS. 3-4 and 6 illustrate a (single use) plastic infiltration cannula 30. The cannula 10, 30 can be inserted under the skin 52 and into the subcutaneous tissue 50 and tumescent local anesthesia can be infiltrated either continuously until the clinical goal is achieved or intermittently (by way of example and not limitation, once every eight to twelve hours).

Stainless steel infiltration cannulae 10, such as the one shown in FIGS. 1 and 2, are formed having precision high quality and are preferably reusable. These cannulae can be used to provide tumescent local anesthesia for surgical procedures, such as liposuction, which require tumescent local anesthesia over a relatively large area.

The cannula 10 includes a tubular needle portion 12 which has a proximal end 14 and a distal end 16. The proximal end 14 of the tubular needle 12 is attached to a hub 20 that is used by the anesthesiologist or surgeon to grasp and hold the cannula 10 during the infiltration procedure. The hub 20 is connected to the tubular needle 12 at a first end 22 and has a connector 24, such as a luer lock, at an opposing second end. The connector 24 is connected to a fluid source, such as tubing connected to an IV bag. Fluid enters the cannula 10 via the connector 24.

In exemplary embodiments, the tip at the distal end 16 is closed. The local anesthetic is infiltrated into the patient via apertures 18 located proximate the distal end 16 of the tubular needle 12 of the cannula 10. It is contemplated that the apertures 18, 38 and 54 discussed herein may have a helical, spiral, linear or any random or ordered pattern. Also, in exemplary embodiments, the apertures 18 are disposed along the distal end 16 of the cannula 10 in a spiral or helical pattern and are distributed over the distal 33% to 100% of the tubular needle 12 of the cannula 10. For example, if the length of the tubular needle D is 15 cm and the apertures 18 at the distal end 16 cover a length d1 of 5 cm, the pattern of apertures of the cannula 10 are preferably distributed over 33% of the tubular needle 12 of the cannula 10. The size of the aperture and density of apertures on the tubular needle is limited by the structural integrity of the cannula. If the apertures 18 are too large or too close together then the cannula may bend or break during use (e.g., routine clinical applications). Prior art cannulae wherein the apertures are limited to the distal 25% of the cannula eject the fluid into the subcutaneous tissue at a high rate so as to cause discomfort to the patient. The apertures 18 which are located along a greater length of the cannula compared to prior art cannula allows fluid to flow out of each of the apertures at a slower rate but to achieve a greater amount of fluid flow as an aggregate so as to reduce the amount of discomfort to the patient due to the rate at which fluid flows out of each of the apertures. When tumescent fluid is injected into subcutaneous tissue, tumescent fluid spreads by means of simple bulk-flow through the interstitial gel substance. This process is extremely rapid and unimpeded by fibrous tissue.

The proximal portion 14 of the cannula 10 may be devoid of apertures in order to prevent fluid from leaking out of the cannula insertion site in the skin. Alternatively, if the proximal portion 14 of the cannula has aperture(s), then the hub may be used to prevent fluid from leaking out of the cannula insertion site in the skin in the follower manner. The hub of the infiltration cannula serves as a connector. The distal end of the hub attaches to the cannula, while the proximal end of the hub detachably connects to the plastic tube set which carries tumescent solution to the cannula. With a slight modification, the hub can also assist in reducing or virtually eliminating leakage of tumescent fluid out through the skin incision or adit site. An adit is a small round hole in the skin typically produced by a biopsy punch. The hub 20 may have a conical configuration. The hub 20 may become narrower from the proximal end of the hub to the distal end of the hub. The rate at which the hub 20 becomes narrow may be less than about fifteen degrees with respect to a centerline of the hub. The outer surface of the hub 20 may have a plurality of rounded circular ridges equally spaced apart. The adit may be formed so as to have a diameter which is less than a diameter of the cannula or the outer surface of the hub. To minimize leakage of tumescent fluid out onto the surface of the skin, the cannula may initially be inserted into the adit. The adit is slightly stretched to accommodate the cannula. The cannula may be fully inserted into the subcutaneous tissue of the patient such that the distal end of the hub contacts the adit. The hub may then be pushed into the adit such that the inner diameter of the adit expands and slides over the rounded circular ridges formed on the distal end of the hub. The hub is gently wedged into the adit until there is a snug fit between the infiltration cannula and the adit. Leakage of fluid out of the adit may also be minimized by placing the proximal most aperture on the cannula sufficiently deep within the subcutaneous tissue such that fluid injected from the most proximal hole produces localized interstitial tumescence and a snug fit of the tissue against the cannula. It is also contemplated that the hub has other shapes such as curved, linear, parabolic, or combinations thereof.

Flexible plastic infiltration cannulae 30, such as the one shown in FIGS. 3, 4 and 6 are single use cannulae and can be used in one of several unique ways. First, an anesthesiologist, surgeon, untrained first responder, or even a victim can insert infiltration cannula 30 with stylet 46 into the subcutaneous tissue 50, remove the stylet 46, then attach IV tubing to the infiltrator and inject tumescent local anesthesia or other tumescent fluid into the targeted area without subsequent repositioning of the infiltration cannula 30. The plastic flexible nature of the tubular needle 32 of the disposable plastic cannula 30 allows the patient to move or change position of the body without risk of injury that might result if a patient moves while a rigid steel cannula is inserted.

In some embodiments, the stylet 46 is formed of a rigid material such as metal, stainless steel, or plastic material. The stylet 46 should be sufficiently rigid so as to guide the tubular needle 32 of the cannula 30 into the subcutaneous tissue 50. The stylet 46 may be solid (see FIG. 4) or hollow (see FIG. 7) through its center. The stylet may either be straight or curved. The plastic cannula 30 can be blunt-tipped with the metal stylet tip 48 covered by the rounded tip 39 of the plastic cannula 30, as shown in FIG. 4. Alternatively, the plastic cannula 30 can be open-ended with the stylet 46 extending a short distance past the end 39 of the plastic cannula 30 as shown in FIG. 6. In the case of the open ended cannula, the stylet 46 can be either blunt-tipped (see FIG. 6; requiring a skin incision to permit insertion into the subcutaneous space), or sharp-tipped (see FIG. 7; permitting the cannula to be inserted directly through the skin and into the subcutaneous space or muscle without requiring a preparatory skin incision). The sharp-tipped stylet 46 can be formed in either a solid (see FIG. 4) or hollow (see FIG. 7) cross-sectional configuration. The utility of a sharp tipped hollow stylet is that it can be inserted directly through the skin and then advanced painlessly through the subcutaneous tissue by slowly injecting local anesthetic solution through the stylet as it is slowly advanced, thereby anesthetizing the tissue in advance of the stylet's tip.

Figure 7:
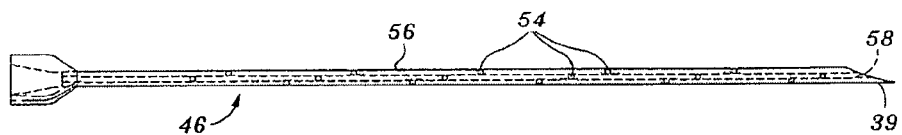
FIG. 7 is a side elevation view of a hollow sharp-tipped stylet with holes located along nearly the entire length of the stylet.

If the stylet 46 is hollow through its center 58, then apertures 54 may be formed along an entire length or along a portion (e.g., about 33% to 100%) of the length of the tubular needle 56 of the stylet 46, as shown in FIG. 7. The hollow stylet 46 (see FIG. 7) may be utilized in a similar fashion as the cannula 10 shown in FIGS. 1 and 2 and described herein. By way of example and not limitation, during use, the tubular needle 56 shown in FIG. 7 may be inserted into the cannula 30. The combined tubular needle 56 and cannula 30 may be inserted through the subcutaneous tissue 50 of the patient. The tubular needle 56 may be removed from the patient and the cannula 30. The tubular needle 56 of the stylet 46 may now be reinserted into the patient at a different site and used as a rigid cannula similar to the cannula 10 discussed in relation to FIGS. 1 and 2.

The stylet 46 shown in FIG. 7 has apertures 54 about the periphery of tubular needle 56 of the stylet 46. The apertures 54 may have a pattern which is dissimilar to the pattern of apertures 38 formed in the tubular needle 32 of the cannula 30. Alternatively, the apertures 54 may have a pattern which is identical to the pattern of apertures 38 formed in the tubular needle 32 of the cannula 30. As a further alternative, some of the apertures 54 may have a pattern which is identical to the pattern of apertures 38 formed in the tubular needle 32 of the cannula 30. Also, some of the apertures 54 may have a pattern which is dissimilar to the pattern of apertures 38 formed in the tubular needle 32 of the cannula 30. During use, the medical professional may insert the stylet 46 (see FIG. 7) with apertures 54 into the cannula 30. The apertures 54 of the stylet 46 may be aligned or misaligned to the apertures 38 of the tubular needle by turning the stylet 46 within the cannula 30. The stylet 46 may have a hub with a similar configuration as hub 40. The hub of the stylet 46 may also be wedged into the adit of the patient to minimize or eliminate leakage of fluid, as discussed herein.

The plastic cannula shown in FIGS. 3 and 4 is similar to an IV catheter except the sharp hollow stylet used for the insertion of an IV catheter can be replaced by a solid obturator/stylet 46 that can be either sharp or blunt tipped. Except for the removable stylet 46, the plastic cannula 30 is similar to the stainless steel cannula 10 shown in FIGS. 1 and 2 and described above. The plastic cannula 30 includes a flexible tubular needle 32 having a proximal end 34 and a distal end 36. The distal end has apertures 38 and the proximal end 34 may be devoid of apertures. As stated above, in exemplary embodiments, the pattern of apertures 38 in the cannula 30 are distributed over the distal 33% to 100% (see FIG. 4) of the tubular needle 32 of the cannula 30. For example, if the tubular needle 32 of cannula 30 shown in FIGS. 3 and 4 has a length D of 15 cm and the pattern of apertures are distributed over a length d1 of 13.5 cm, then the apertures 38 are distributed over 90% of the cannula. As a further example, if the tubular needle 32 of cannula 30 shown in FIGS. 3 and 4 has a length D of 15 cm and the pattern of apertures are distributed over a length d1 of 15 cm, then the apertures 38 are distributed over 100% of the cannula. To stop leakage of tumescent fluid out of the adit site, the hub may be wedged into the adit site, as discussed above.

A typical infiltration cannula 10, 30 may have a diameter equivalent to 20, 18, 16 or 14 gauge with small apertures 18, 38 placed every 5 mm along the cannula in a spiral or helical pattern. The infiltration cannula 10, 30 may be 20-14 cm in length. A typical infiltration cannula 10, 30 is 15 cm or 20 cm in length. It will be appreciated that the dimensions used herein are exemplary and that the cannula dimensions, range of gauge, length range of cannula, relative size shape and pattern of apertures can vary greatly depending upon clinical preference.

The proximal end 34 of the tubular needle 32 shown in FIGS. 3 and 4 is attached to a hub 40 that is used by the anesthesiologist or surgeon to hold the cannula 30 during the infiltration procedure. The hub 40 is connected to the tubular needle 32 at a first end 42 and has a connector 44 at an opposing second end. The connector 44 is connected to a fluid source. As described above and shown in FIG. 4, the stylet 46 can be inserted and removed from the cannula 30.

Infiltration using a plastic infiltration cannula 30, such as the one shown in FIGS. 3 and 4, can be accomplished using an infiltration pump. Alternatively, the force of gravity could be used to push the tumescent fluid into the tissues by hanging a reservoir plastic bag of tumescent local anesthesia (or other dilute drug, such as a chemotherapeutic agent or antibiotics) on an IV pole and connecting bag to the infiltration cannula by an IV line.

Tumescent local anesthesia may be provided to a localized area through which a surgeon plans to make a surgical incision. Tumescent local anesthesia involves the administration of dilute anesthetic solutions into the subcutaneous fat compartment. One example of a tumescent solution used in a liposuction procedure comprises a combination of 500-1000 mg of the anesthetic lidocaine per liter of solvent (typically normal saline or lactated Ringer's solution) along with a vasoconstrictor such as epinephrine to control the rate of lidocaine absorption and reduce bleeding. Bicarbonate may be included to reduce patient discomfort from an otherwise acidic solution. Anti-inflammatory agents may also be included. Once it was shown that this technique was able to safely provide consistent levels of local anesthesia for a large area of the body over a long period of time with little risk of toxicity, it became the standard of care for liposuction. A description of this procedure can be found in Jeffrey A. Klein, *The Tumescent Technique*, DERMATOLOGIC CLINICS, vol. 8, No. 3, pp. 425-437, 1990.

The use of tumescent local anesthesia converted liposuction from a hospital-based procedure requiring general anesthesia and often blood transfusions to an office-based procedure. The tumescent technique has subsequently been adapted for use in a variety of other surgical procedures including hair transplantation, phlebectomy, mastectomy, sentinel node biopsy, and others.

The effects of vasoconstriction, resulting from the epinephrine in the tumescent local anesthetic solution, within the tumesced tissue minimizes surgical bleeding. In a uniquely preemptive fashion, the pre-operative infiltration of tumescent local anesthesia produces prolonged post operative analgesia and preemptively reduces the risk of surgical wound infections resulting from the bactericidal effects of lidocaine.

Lidocaine is bactericidal in vitro against *S. aureus*, and this effect increases with greater duration of exposure. In a dose-dependent fashion, clinical doses of lidocaine have been shown to inhibit the growth of bacterial pathogens commonly encountered in nosocomial wound infections. A tumescent epinephrine induces profound local vasoconstriction resulting in significantly delayed systemic absorption of a tumescent antimicrobial drug from subcutaneous tissue. In commercially available concentrations, the systemic absorption of an aqueous solution of lidocaine requires approximately 2 to 4 hours. In contrast, the systemic absorption of tumescent lidocaine requires 24 hours or more. Accordingly, a tumescent antibiotic can be expected to remain within the peri-incisional tissue at least 12 times longer than a routine aqueous antibiotic solution and the action would be far more effective. Moreover, a tiny hematoma within an incision may be an isolated avascular space and a potential nidus for an infection. The profound and prolonged vasoconstriction induced by tumescent epinephrine minimizes surgical bleeding and hematoma formation and therefore reduces the risk of surgical site infection. Hypothermia is a major risk factor for postoperative surgical site infection. Mild perioperative hypothermia is common among patients having surgery under general anesthesia. The incidence of SSI was 5.8% in the normothermic (core body temperature 37 degrees C.) group and 18.8% in the hypothermic group (34.4 degrees C.) in a randomized, double blind trial. (Kurtz A, Sessler D I, Lenhardt R. Perioperative normothermia to reduce the incidence of surgical-wound infections and shorten hospitalization. Study of wound infection and temperature group. N Eng J Med 334:1209-15, 1996). Hypothermia also causes delays in moving the patient out of the recovery room. With surgery totally by tumescent local anesthesia there is no evidence of post operative hypothermia.

Some embodiments relate to infiltration of a tumescent solution comprising an anesthetic component, a vasoconstrictive component, and an antibiotic component. Other embodiments relate to infiltration of a tumescent solution comprising a vasoconstrictive component and an antibiotic component. Other embodiments relate to infiltration of a tumescent solution comprising an anesthetic component and an antibiotic component. Other embodiments relate to infiltration of a tumescent solution comprising an anesthetic component and a vasoconstrictive component. Some embodiments relate to infiltration of a tumescent solution comprising an anesthetic component. Some embodiments relate to infiltration of a tumescent solution comprising a vasoconstrictive component. Some embodiments relate to infiltration of a tumescent solution comprising an antibiotic component. Some embodiments relate to infiltration of a tumescent solution comprising crystalloid fluids/electrolytes.

In one embodiment, infiltration of a tumescent solution comprising lidocaine, epinephrine, and an antibiotic improves surgical site infection prophylaxis. Tumescent infiltration of antibiotics into peri-incisional skin and subcutaneous tissue offers the following advantages: prolonged local tissue concentrations of antibiotics and prolonged systemic delivery of antibiotic to tissues distant from the incision site. The systemic absorption of tumescent lidocaine mimics IV delivery of lidocaine which is known to reduce postoperative pain and hasten post operative discharge from the hospital. Embodiments of the infiltration cannula discussed herein may be used for tumescent delivery of antimicrobial drugs.

Several embodiments relate to application of the tumescent technique to provide an easily accessible route for systemic administration of crystalloid fluids/electrolytes for systemic hydration or for other types of drug therapy. Potential clinical applications include emergency resuscitation with systemic fluids in situations where insertion of an IV catheter into a vein cannot be readily achieved. Examples of situations where emergency access for intravenous delivery of fluids might not be possible include acute trauma or burn wound in civilian or military situations and very obese patients in which finding an accessible vein for IV access can be difficult even for a physician skilled in performing "IV cut-down" procedures. Embodiments of the infiltration cannula discussed herein may be a valuable adjunct to fluid resuscitation in an ambulance or an emergency room. Another application may be the emergency treatment of dehydration associated with pandemic influenza, prolonged vomiting or diarrhea as a result of chemical warfare or biological warfare (e.g., epidemic cholera among pediatric patients in rural third world settings) or other types of medical emergencies which overwhelm a medical center's capacity to care for incoming victims. A subcutaneous infiltration catheter can easily be introduced by a layman, whereas inserting an IV catheter into a vein of a patient that is severely dehydrated can be difficult even for a skilled physician. Delivery of systemic fluids by subcutaneous infiltration is safer than an IV infusion in a zero gravity situation (for example, the Space Station). The addition of a small amount of capillary vasodilator (e.g., methylnicotinamide) to the subcutaneous fluid can be used to accelerate the systemic absorption of the fluid or drug into the intravascular space. Further applicational uses for the present embodiments are described in co-pending application Ser. No. 10/877,337, filed Jun. 25, 2004, the disclosure of which is expressly incorporated herein by reference.

The continuous systemic drug delivery by tumescence has a similar therapeutic effect to continuous IV infusion but without the inherent expense, difficulties, and risk of an IV infusion. Compared to either oral delivery of a drug (inconsistent absorption from the gastrointestinal tract), or periodic intramuscular (IM) injections of a drug (variable serum concentrations), continuous systemic delivery is preferred in order to achieve prolonged and relatively uniform blood concentrations of the drug. This is especially true in critically ill patients. Tumescent delivery of a drug, placed in a tumescent solution containing epinephrine as a vasoconstrictor, produces prolonged continuous system absorption of the drug over an interval of more than 24 hours. The simplicity and inexpensive equipment required to achieve continuous tumescent systemic drug delivery is clearly an advantage among medically impoverished populations, and in the demanding conditions of battlefield or at the scene of a mass casualty.

Yet another application is related to astronauts and systemic delivery of medication. In particular, the therapeutic options for treating an injured astronaut are limited. The fate of injured airplane pilots, passengers and astronauts are similar in that we presently have virtually no in-flight capability for treating an acute traumatic injury. If a pilot or astronaut survives the immediate effects of an explosion, burn, or decompression injury, or if there is an acute non-traumatic medical illness, it is assumed that the victim must return to terra firma for any significant therapeutic intervention such as providing systemic fluid replacement. The tumescent infiltrator is capable of providing systemic fluid and thus it is successfully solving a problem that has either never before been recognized, or has never before been solved by a simple device and technique.

The present embodiments allow improved emergency medical care for an injured astronaut on-board the International Space Station. Repeated and prolonged extra vehicular activities (EVA) expose astronauts to greater risk of physical trauma injury. Potential injuries to astronauts include decompression injury-induced neurological injury and coma, acute pneumothorax, burns, and radiation injury. Assembly and maintenance of the International Space Station requires an unprecedented number of spacewalks, which expose astronauts to the risk of decompression sickness (DeS). In addition to humanitarian concerns, there is a strong economic incentive to provide on-board care for acute illness or trauma: the only alternative would be to abort an expensive mission and immediately return the victim to earth.

At present, there is no safe and easy means of providing the equivalent of IV fluids to a patient in space. Assuming there is a fellow astronaut with the requisite clinical skill to insert an intravenous (IV) catheter in a weightless environment, there is a problem of zero gravity. Whereas gravity separates air and water into distinct layers, in zero gravity there is a risk of air bubbles from the IV bag entering the IV line and causing intravascular air embolism. Because subcutaneous air is relatively safe, the tumescent infiltration cannula, by allowing effective systemic fluid resuscitation via subcutaneous infiltration, overcomes the above problems, and allows a person without clinical skills to safely provide the equivalent of IV fluids.

The cannula 10, 30 is intended to be inserted far enough through the skin 52 so that all of the apertures 18, 38 are within the fat 50 or muscle of the patient. If the apertures 18, 38 are distributed over about 100% of the cannula, the hub may be wedged into the adit to prevent or minimize leakage of the tumescent fluid out of the adit. Once the cannula 10, 30 is properly positioned, it can remain stationary while the local anesthetic (or other pharmaceutical) solution is injected. Since the cannula remains stationary, the associated pain or discomfort typically caused by the reciprocating in and out movement of prior art cannulae is reduced or eliminated. Accordingly, the cannula of the present invention permits infiltration of multi liter volumes of tumescent fluid into the patient in a safe and painless manner.

After one portion of the targeted area has been tumesced, the infiltration is briefly terminated (either by turning off the pump or by clamping the IV tubing) while the cannula 10, 30 is repositioned into another area of the subcutaneous tissue. Typically, the cannula is repositioned at the rate of about once per minute. The infiltration is then restarted with the cannula stationary in its new position. Since the apertures are distributed over the distal 33% to 100% of the cannula, the apertures distribute tumescent fluid into the patient along the entire length of cannula insertion. The cannula does not have to be reciprocated in and out to infiltrate the subcutaneous tissue like prior art cannula. Progressing repeatedly in this fashion, eventually all the fat within a targeted area becomes tumescent and profoundly anesthetized. Such method can obviate the need for general anesthesia or heavy IV sedation in most surgical procedures restricted to the skin and subcutaneous tissue.

The infiltrator 10, 30 can also be used in the traditional mode whereby the cannula 10, 30 is moved through the targeted tissue while the fluid is simultaneously pumped through the cannula 10, 30 and into the subcutaneous tissue 50.

Another unique aspect of the tumescent technique's reservoir effect is that one can conveniently achieve a long, slow, steady absorption of a drug delivered to the subcutaneous space 50 using periodic injections of a tumescent solution. In certain situations, using a slow IV infusion, the alternative technique, can achieve a slow systemic absorption of a drug but may be difficult, require greater clinical expertise, be more expensive, and therefore, less practical than the technique described herein.

Figure 5:
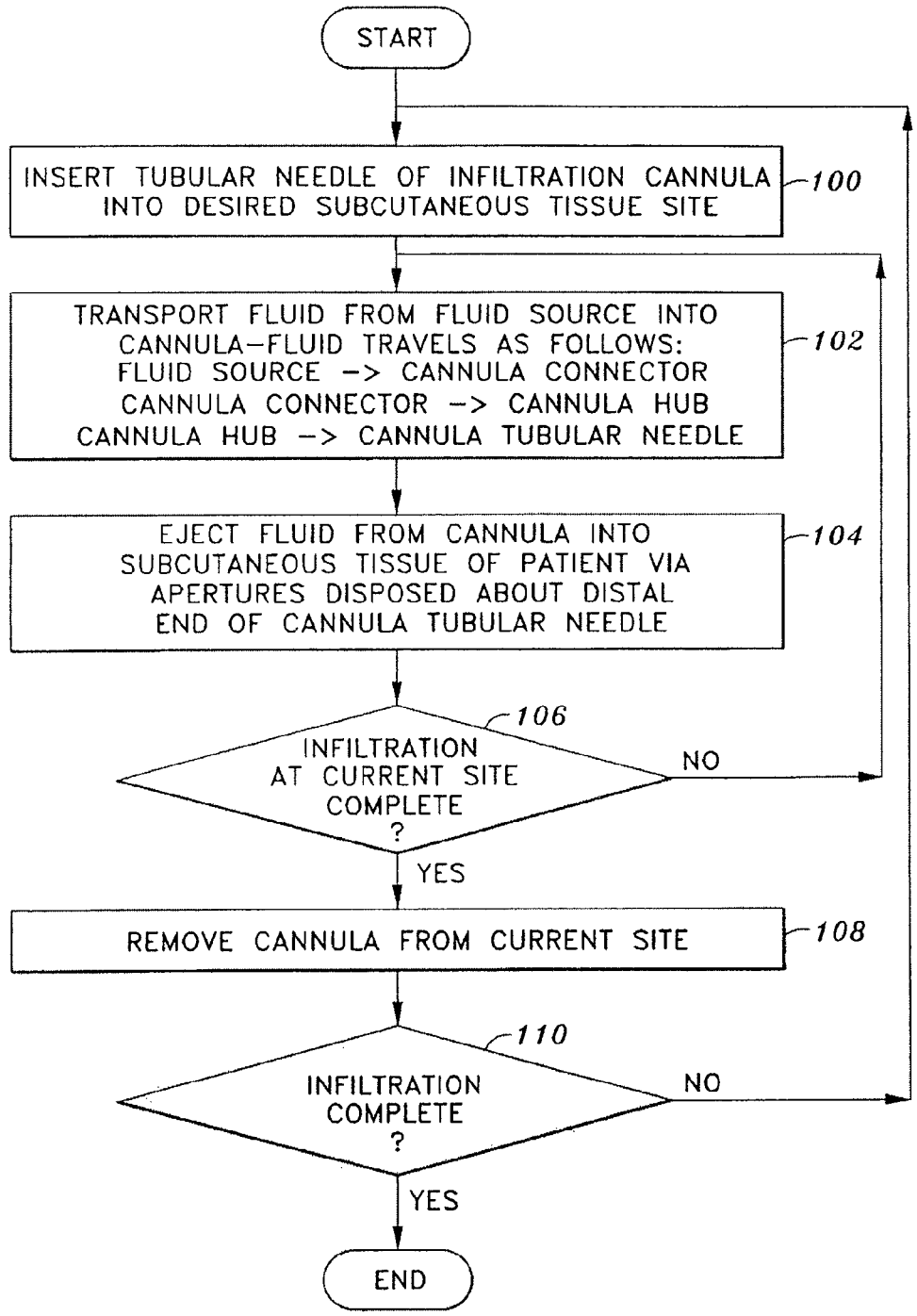
FIG. 5 is a flow diagram illustrating an exemplary procedure for using an infiltration cannula such as the one shown in FIG. 1 or the one shown in FIG. 3.

FIG. 5 is a flow diagram illustrating steps performed in an exemplary infiltration procedure using a cannula 10, 30 such as the one shown in FIGS. 1 and 2 or the one shown in FIGS. 3 and 4, respectively. The procedure begins by inserting the tubular needle 12, 32 of the infiltration cannula 10, 30 into a desired subcutaneous tissue site 50, e.g., via an incision in the patient's skin 52 (block 100). Fluid is then transported from the fluid source (e.g., an IV bag) into the cannula 10, 30 via the connector 24, 44 that is connected to the fluid source. The fluid is transported from the connector 24, 44 through the hub 20, 40 and into the tubular needle 12, 32 (block 102). The fluid is then ejected from the cannula 10, 30 into the subcutaneous tissue 50 of the patient via the apertures 18, 38 at the distal end 16, 36 of the tubular needle 12, 34 of the cannula 10, 30 (block 104).

The fluid is transported (block 102) and ejected (block 104) until infiltration at the current site is completed (yes in decision block 106). Complete infiltration at the current site may take approximately one or two minutes. The fluid can be injected into multiple sites in order to distribute the solution over a greater area.

Infiltration at a particular site may be deemed complete upon emptying of the fluid source or based on the anesthesiologist or surgeon's decision to stop the infiltration at the current site. After one portion of the targeted area has been tumesced, the infiltration can be briefly terminated (either by turning off the pump or by clamping the IV tubing) while the cannula 10, 30 is repositioned into another area of the subcutaneous tissue. The infiltration may then be restarted with the cannula stationary in its new position. If the infiltration at a site is complete (yes in decision block 106), the cannula is removed from the current site (block 108). If the infiltration at the current site is not complete (no in decision block 106), fluid is transported from the fluid source (block 102) and ejected into the subcutaneous tissue (block 104) until infiltration at the site is complete (yes in decision block 106).

If infiltration is complete at the current site (yes in decision block 106) but infiltration is not complete (no in decision block 110); the tubular needle 12, 32 of the infiltration cannula 10, 30 is inserted into a new area of subcutaneous tissue 50. By way of example and not limitation, the tubular needle 12, 32 may be inserted into a new area adjacent the current site. The adjacent site may be partially anesthetized by infiltration of the anesthetic solution at the current site. As such, pain to the patient caused by insertion of the tubular needle 12, 32 is minimized, eliminated or greatly reduced. The process described above is performed until the infiltration process is complete (yes in decision block 110). This process can be continuous or repeated intermittently. It is contemplated that infiltration of up to about 50% of the patient's body may be achieved in the manner described herein.

As described above, multiple infiltration cannulae (e.g., can be used at once). Thus, a second or additional cannulae can be inserted (block 100) at the same time as a first cannula is being removed (block 108). For example, the second cannula may be inserted parallel to the first cannula and into an area immediately adjacent to the area in which the first cannula is inserted. In this manner, the pain usually associated with the insertion of the cannula into the patient's fat tissue is reduced or eliminated because the first cannula has already at least partially anesthetized the area in which the second cannula is inserted. The second cannula is positioned adjacent the first cannula approximately every one or two minutes. The first cannula may then be removed from the patient's body after the second cannula is inserted. Moreover, the infiltration process need not be interrupted in order to reposition a single cannula. Progressing repeatedly in this fashion, eventually all the fat within a targeted area becomes tumescent and profoundly anesthetized. As such, such method can obviate the need for general anesthesia or heavy IV sedation.

The plastic infiltration cannula shown in FIGS. 3 and 4 may be used by either a lay person or a clinical professional for the delivery of tumescent fluid for either tumescent local anesthesia, tumescent antimicrobial therapy, or emergency delivery of systemic fluids by tumescent infiltration. In an aspect of the cannulae 10, 30, it is contemplated that such cannulae 10, 30 may be utilized for continuous systemic tumescent delivery of a drug which produces continuous system absorption of the drug over nearly 24 hours in a fashion similar to a continuous IV infusion.

The infiltration cannula 10, 30 discussed herein is a subcutaneous device and not an intravascular device for infiltration of multi-liter volumes of fluid into areas of up to 50% of the total body surface area. For example, the infiltration cannulae 10, 30 infiltrates approximately 1,000 times the volume of fluid delivered by the Schwartz device discussed in the background.

Additional modifications and improvements of the present invention may also be apparent to those of ordinary skill in the art. Thus, the particular combination of parts described and illustrated herein is intended to represent only a certain embodiments, and is not intended to serve as a limitation of alternative devices within the spirit and scope of the disclosure.

Tumescent Administration of Antibiotic

The tumescent technique may be used to deliver an antimicrobial solution by subcutaneous infiltration. In some embodiments, the antimicrobial solution may comprise an antibiotic. In some embodiments, the antimicrobial solution may also comprise a local anesthetic and/or a vasoconstrictor. Upon delivery of a large volume of solution to the subcutaneous compartment, the surrounding tissue becomes swollen and firm—tumescent. The tumescent technique can be advantageously employed to deliver antibiotics and other agents to a surgical site or the sites of other medical procedures. Some embodiments relate to tumescent antibiotic delivery (TAD) to areas of infection. TAD may be employed prophylactically to prevent an infection or TAD may be employed to treat an existing infection. In certain embodiments, a large volume (≥1 L for example) of dilute antibiotic solution is provided to a site where antibiotic is needed, foregoing the disadvantages of systemic delivery. The antibiotics for tumescent delivery may be provided in a solution of tumescent local anesthetic or without combination with local anesthetic.

Several embodiments relate to a solution comprising an antibiotic component, an anesthetic component, a vasoconstrictor component and a solvent (hereafter referred to as Tumescent Local Antibiotics or TLAnti) to be delivered utilizing the tumescent technique. The relative concentrations of the components of TLAnti may be varied depending upon the level of anesthesia required at a given surgical site, the likelihood of bleeding, risk of infection, or other factors specific to the patient such as age, weight, or liver function.

In some embodiments, the anesthetic component may be comprised of a mixture of 2 or more anesthetics. In some embodiments, the vasoconstrictive component may be comprised of a mixture of 2 or more vasoconstrictors. In some embodiments, the antibiotic component may be comprised of a mixture of 2 or more antibiotics. In some embodiments the anesthetic component may possess both anesthetic and antibiotic properties. In some embodiments, TLAnti may additionally comprise an antiviral and/or an antifungal component. In some embodiments, the TLAnti may comprise additional pharmacological agents, such as, but not limited to, anticonvulsants, stimulants, sedatives, antihistamines, retinoids, corticosteroids, calcium antagonists, chemotherapy agents, prostacyclins, and vasodilators.

In some embodiments, TLAnti comprises a water-soluble antibiotic component. In one embodiment, the water-soluble antibiotic may be Cefazolin. Cefazolin is a first generation cephalosporin that has been sold under the brand names Ancef and Kefzol. This medication is particularly effective against many varieties of gram-positive bacteria that are typically present on the epidermal surface such as *Staphylococcus aureus*. Antibiotic coverage for such ubiquitous organisms is particularly important in surgical procedures because they can enter the surgical site during the procedure and are therefore a likely cause of post-operative infection. In some embodiments, cefazolin is used at a dosage of approximately 250 to 750 mg per liter of solvent. For example, in one embodiment 500 mg of cefazolin is used in 1 liter of TLAnti. In other embodiments cefazolin may be used at a dosage of approximately 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, or 900 mg per liter of solvent.

Persons skilled in the art will recognize that there are a variety of water-soluble antibiotics other than cefazolin that can be used in TLAnti. In some embodiments, TLAnti may comprise a combination of two or more water-soluble antibiotics. In some embodiments, penicillins, cephalosporins, carbapenems, aminoglycosides, sulfonamides, quinolones, macrolides, tetracyclines, lipopetides and oxazolidinones may be used. In one embodiment, metronidazole is used in TLAnti. Suitable antibiotics can be substituted in cases wherein a patient has a known or suspected hypersensitivity to a class of antibiotics, such as cephalosporins, or if the procedure is being performed in an area where resistance to a particular antibiotic is prevalent. In some embodiments, TLAnti may be used to treat an existing infection. In such embodiments, the infective agent may be determined and tested for antibiotic resistance. The antibiotic or combination of antibiotics may be specifically selected based on the resistance profile of the bacterial flora.

Examples of suitable antibiotics include, but are not limited to: amoxicillin, ampicillin, bacampicillin, carbenicillin, cloxacillin, dicloxacillin, flucloxacillin, mezlocillin, nafcillin, oxacillin, penicillin G, penicillin V, Piperacillin, Pivampicillin, Pivmecillinam, Ticarcillin, cefacetrile, cefadroxil, cephalexin, cefaloglycin, cefalonium, cefaloridine, cefalotin, cefamandole, cefapirin, cefatoxin, cefatrizine, cefazaflur, cephalexin, cefazedone, cefazolin, cefepime, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefminox, cefotetan, cefoxitin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, imipenem, meropenem, ertapenem, doripenem, panipenem, betamipron, biapenem, razupenem, amikacin, arbekacin, gentamicin, kanamycin, neomycin, netilmicin, paromomycin, rhodostreptomycin, streptomycin, tobramycin, apramycin, framycetin, ribostamycin, bekanamycin, dibekacin, tobramycin, spectinomycin, hygromycin B, paromomycin sulfate, sisomicin, isepamicin, verdamicin, astromicin, sulfasalazine, sulfamethoxazole, sulfamethizole, sulfisoxazole, fluoroquinolone, ketolide, ceftobiprole, flumequine, nalidixic acid, oxolinic acid, piromidic acid, pipemidic acid, rosoxacin, ciprofloxacin, enoxacin, lomefloxacin, nadifloxacin, norfloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, azithromycin, erythromycin, clarithromycin, dirithromycin, roxithromycin, telithromycin, demeclocycline, doxycycline, minocycline, oxytetracycline, tetracycline, linezolid, clindamycin, metronidazole, vancomycin, rifabutin, rifampin, nitrofurantoin, chloramphenicol.

In several embodiments, TLAnti may also comprise an anesthetic component. In some embodiments, the anesthetic component may comprise lidocaine. In some embodiments, lidocaine may be provided at a concentration of between 30 mg and 1500 mg per liter of solvent. In some embodiments, lidocaine may be provided at a concentration of between 400 mg and 1250 mg per liter of solvent. In other embodiments, lidocaine may be provided at concentrations of 30 mg to 40 mg, 40 mg to 50 mg, 50 mg to 60 mg, 60 mg to 70 mg, 70 mg to 80 mg, 80 mg to 90 mg, 90 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, 900 mg to 1,000 mg, 1,000 mg to 1,100 mg, 1,100 mg to 1,200 mg, 1,200 mg to 1,300 mg, 1,300 mg to 1,400 mg, 1,400 mg to 1,500 mg, and 500 mg to 1,000 mg per liter of solvent.

In some embodiments, anesthetics other than lidocaine can be used. Examples of anesthetics include, but are not limited to saxitoxin, tetrodotoxin, benzocaine, chloroprocaine, cocaine, cyclomethycaine, dimethocaine, larocaine, propoxycaine, novocaine, proparacaine, tetracaine, amethocaine, articane, bupivacaine, carticaine, cinchocaine, dibucaine, etidocaine, levobupivacaine, mepivacaine, piperocaine, prilocaine, ropivacaine, trimecaine. In some embodiments, combinations of two or more anesthetics may be used. Suitable concentrations of anesthetic are approximately 30 mg to 40 mg, 40 mg to 50 mg, 50 mg to 60 mg, 60 mg to 70 mg, 70 mg to 80 mg, 80 mg to 90 mg, 90 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, 900 mg to 1,000 mg, 1,000 mg to 1,100 mg, 1,100 mg to 1,200 mg, 1,200 mg to 1,300 mg, 1,300 mg to 1,400 mg, 1,400 mg to 1,500 mg, and 500 mg to 1,000 mg per liter of solvent.

The concentration of the anesthetic component can be varied depending on the sensitivity of the treatment area and the sensitivity of the patient to pain. If the TLAnti is to be used in sensitive areas such as the face or breasts, a higher concentration of anesthetic can be used. Lower concentrations of anesthetic can be used in the TLAnti solution for procedures in less-sensitive areas such as the hips.

TLAnti may further comprise a vasoconstrictor component. Not wishing to be bound by a particular theory, the inclusion of a vasoconstrictor serves two functions. The first is to control the otherwise substantial bleeding resulting from the removal of adipose or other tissue. The second is to control the systemic distribution of the anesthetic and antibiotic components of TLAnti from the subcutaneous fat compartment into the systemic circulation. This helps to concentrate these medications in the area where they are needed for a prolonged period of time, thereby enabling them to exert sufficient anesthetic and antibiotic effects in the surgical site post-operatively or at the site of infection. In addition, the use of a vasoconstrictor limits the systemic absorption of other medications, which reduces the risk of systemic toxicity from elevated serum levels of these medications and thereby minimizes the risk of side effects.

In some embodiments, the vasoconstrictor component is epinephrine. Epinephrine may be provided at a concentration of ≤1 mg/L. In some embodiments, epinephrine is present in a concentration of 0.4 to 1.2 mg per liter of solvent. In other embodiments, epinephrine may be present in a concentration of 0.2 to 0.3 mg, 0.3 to 0.4 mg, 0.4 to 0.5 mg, 0.5 to 0.6 mg, 0.6 to 0.7 mg, 0.7 to 0.8 mg, 0.8 to 0.9 mg, 0.9 to 1 mg, 1 to 1.1 mg, 1.1 to 1.2 mg, 1.2 to 1.3 mg, 1.3 to 1.4 mg, or 1.4 to 1.5 mg per liter of solvent. Stability of epinephrine is optimized is solutions of a moderately acidic pH. TLAnti solutions containing epinephrine would be manufactured with a moderately acidic pH in the range of 3.8 to 5.0 in order to optimize the shelf life of the TLAnti solution. In order to avoid the burning discomfort associated with the infiltration of an acidic solution, the TLAnti solution can be neutralized prior to subcutaneous infiltration by the addition of approximately 10-25 mEq of sodium bicarbonate.

Individuals skilled in the art will recognize that vasoconstrictors other than epinephrine can be used in some embodiments of TLAnti. Examples of suitable vasoconstrictors include, but are not limited to, methoxamine, metraminol, ephedrine, noradrenaline, vasopressin, levonordefrin, prostaglandins, thromboxane A2, leukotriene D4, angiotensin II, neuropeptide Y, and endothelin.

In some embodiments, other constituents may optionally be present in the TLAnti. In one embodiment, bicarbonate can be present in the TLAnti. This helps to neutralize the otherwise acidic solution and reduce the burning sensation reported by many patients. In other embodiments, the TLAnti can further comprise perfluorocarbons. An example can be found in U.S. Pat. No. 6,315,756, the disclosures of which are incorporated in their entirety by reference thereto. In some embodiments TLAnti can further comprise an anti-inflammatory component. Examples of anti-inflammatories include but are not limited to glucocorticoids and NSAIDS. Persons skilled in the art will note that there are a number of potential compounds that can be added to the TLAnti.

In one embodiment, TLAnti comprises lidocaine as the anesthetic component. Lidocaine has a synergistic effect with antibiotics in the prevention and/or treatment of infection at the surgical site. While primarily used as for anesthesia, lidocaine has also been found to have antibiotic properties. Lidocaine is well known to be bactericidal based on in-vitro studies although the precise mechanism has not been explained. Lidocaine is a trans-membrane anion (Na+, K+, Ca+) transport pump inhibitor in prokaryotic cells. Not to be bound by a particular theory, it is believed that lidocaine also acts as an antibiotic efflux pump inhibitor (inhibitor of multidrug resistant efflux systems in bacteria). Lidocaine can thus act synergistically at the local tissue level when both lidocaine and an antibiotic are delivered directly into the targeted tissue using the tumescent drug delivery technique. By inactivating efflux pumps, lidocaine eliminates a mechanism of potential resistance to the cefazolin or other antibiotics used in TLAnti. By flooding the surgical site with significant dosages of two drugs with different and complimentary mechanisms of bactericidal action, the risk of surgical site infection may further be reduced. In addition, tumescent antibiotic delivery of antibiotics together with tumescent lidocaine provides a unique therapeutic benefit in preventing and treating biofilm infections. In contrast, the IV delivery of antibiotics is relatively ineffective against biofilm infections.

Advantages to Using the Tumescent Technique

Tumescent delivery of pharmaceutical agents can provide a highly localized and sustained dosage of the pharmaceutical agent to the delivery site. For example, use of the tumescent technique to deliver TLAnti can provide a high, sustained dosage of antibiotics directly to a surgical site. This has the advantage over the standard treatment with intravenous (IV) antibiotics in that the medication is concentrated and the dosage maximized at the area that is at risk of infection. In some embodiments, the concentration of the antibiotic drug and the local anesthetic drug within the TLAnti (which equals the maximum concentrations of these drugs within the tissues infiltrated with the TLAnti) far exceed the concentrations of these drugs which can be safely achieved by intravenous delivery. In embodiments of TLAnti comprising cefazolin, the concentration of antibiotic in the subcutaneous tissue at the surgical site may be three times or more than the measured maximum serum concentration of the same drug when administered intravenously prior to the procedure. Another advantage is that the therapeutic dosage of antibiotics at the surgical site lasts significantly longer with tumescent administration of TLAnti as compared to IV antibiotics. The result is that any bacteria present at the surgical site are exposed to a higher dosage of antibiotics for a longer period of time when TLAnti is used in place of IV antibiotics.

The bioavailability and effectiveness of an antibiotic can be assessed using the area under the curve (AUC) measurement of the tissue-concentration of the antibiotic as a function of time. After an IV infusion of an antibiotic, the serum-antibiotic AUC may be more than 100 times greater than the serum-antibiotic AUC following tumescent antibiotic delivery. On the other hand, the subcutaneous tissue-antibiotic AUC following the IV delivery of an antibiotic is less than 1/100th the tissue-antibiotic AUC following tumescent antibiotic delivery. Similarly the peak serum concentrations of an antibiotic is higher after IV infusion compared to tumescent antibiotic, while the peak tissue concentration of antibiotic is lower after IV infusion compared to tumescent antibiotic. Tumescent antibiotic delivery produces significantly lower systemic concentrations of antibiotic while at the same time the local tissue concentration of antibiotic at the site of tumescent antibiotic infiltration is dramatically higher than that which can be achieved by IV antibiotic delivery.

Some embodiments relate to a method of using TLAnti during various surgical procedures. For example, in a liposuction procedure, a therapeutic quantity of TLAnti is injected into the subcutaneous compartment. Once sufficient anesthesia is achieved, another cannula is inserted and adipose tissue removed. The cannula is subsequently removed and the surgical site dressed and/or closed as appropriate. The high levels of antibiotics that remain for some period of time in the surgical site can reduce the risk of postoperative infection. Similarly, a large number of general surgical procedures including, but not limited to, open gastrointestinal surgery, obstetric surgery, orthopedic surgery, and vascular surgery are appropriate for the use of subcutaneous TAD.

The targeted application of highly-concentrated antibiotics to the surgical site largely eliminates many of the problems inherent in systemic, prophylactic antibiotic use. In some embodiments where the tumescent solution comprises antibiotic and vasoconstrictive components, substantial quantities of antibiotics are injected into the surgical site using tumescent technique; however, the antibiotics enter the systemic circulation slowly due to the presence of a vasoconstrictive component. This delayed absorption minimizes the systemic antibiotic concentrations and reduces the possibility of the patient experiencing side effects compared with IV antibiotics. In addition, because the normal bacterial flora of the gut is not exposed to a bactericidal dosage of antibiotics when using the tumescent technique to deliver antibiotic, the risk of inadvertently eliminating the benign and protective bacteria in the gastrointestinal system is reduced. This reduces the likelihood of creating conditions favorable for the overgrowth of antibiotic-resistant and pathogenic bacteria such as *Clostridium difficile*. Finally, by not exposing any bacteria present beyond the surgical site to a therapeutic dosage of antibiotics, the risk of promoting the development of antibiotic resistant strains of a variety of pathogenic bacteria is minimized. This helps to reduce the problem of the spread of antibiotic resistant bacteria into the community.

Some embodiments relate to methods for using tumescent solutions in the subcutaneous space to treat a variety of medical conditions where systemic administration of medications is undesirable or impossible. Various embodiments include, but are not limited to, methods for using tumescent solutions as an anesthetic for medical procedures by clinicians, methods for using tumescent solutions in the administration of fluids to patients by medical professionals and first responders, methods for using tumescent antibiotic solutions to prevent and/or treat infections, methods for providing a chemotherapy agent to tissue after tumor removal and methods for using tumescent solutions in the controlled release of antibiotics and other pharmaceutical agents.

Tumescent administration of anesthetics, antibiotics, vasoconstrictors, and/or other pharmaceutical agents can improve the outcome of surgical procedures to remove tumors. Tumors may be benign or malignant, cancerous. Benign tumors are well circumscribed and are generally treated by surgery alone. Malignant/cancerous tumors on the other hand are more difficult to treat. When malignant tumors are localized, surgical removal is a common treatment option. Approximately 40% of all cancers are treated with surgery alone. In most other cases where surgery is an option, it is combined with other treatments—usually radiation therapy or chemotherapy. One danger of the surgical removal of malignant tumors is the possibility of spreading or seeding the cancerous cells during the process of removing the tumor. Tumescent delivery of a vasoconstrictor to the surgical site can reduce the risk of malignant cells entering the bloodstream. The tumescent technique may also be used to locally deliver chemotherapy agents. Local administration of chemotherapy agents allows for higher localized dosages of the chemotherapy agents than would be tolerated systemically and a reduction of adverse side effects. Examples of chemotherapy agents include, but are not limited to: actinomycin D, adriamycin, alkeran, ara-C, arsenic trioxide (trisenox), avastin, BiCNU, busulfan, carboplatinum, CCNU, cisplatinum, cytoxan, daunorubicin, DTIC, 5-FU, erlotinib, fludarabine, gemcitabine, herceptin, hydrea, idarubicin, ifosfamide, irinotecan, lapatinib, leustatin, 6-MP, methotrexate, mithramycin, mitomycin, mitoxantrone, navelbine, nitrogen mustard, rituxan, 6-TG, taxol, taxotere, topotecan, velban, vincristine, VP-16, and xeloda. Other anticancer drugs, such as angiogenesis inhibitors, may also be tumescently delivered. Examples of angiogenesis inhibitors include, but are not limited to, angiostatin, endostatin, and tumstatin.

In some embodiments, the tumescent solutions can be premixed and packaged prior to being sent to the provider. In other embodiments, one or more components of the tumescent solution can be added shortly before or during the medical procedure wherein they are to be used. In most embodiments, the bulk of the tumescent solution comprises a physiologically compatible solvent. Such solvents can include, for example, saline solution comprising sterile water and 0.9% sodium chloride. More dilute saline solutions can also be used. In other embodiments, a lactated Ringer's solution may be used. This comprises a mixture of sterile water, sodium, chloride, lactate, potassium and calcium that is isotonic with blood. Hartmann's solution can also be used as a solvent in some embodiments. Individuals skilled in the art will recognize that there are a wide variety of possible biologically compatible solvents for use in the solution.

In some embodiments, tumescent solution may be provided as a kit. In some embodiments, the tumescent solution is TLAnti. In one embodiment, TLAnti can be pre-mixed at a manufacturing site and distributed to practitioners in a ready to use form. In such embodiments, the TLAnti can be packaged in a form that allows easy interface with a tumescent reservoir or pumping system. Such packaging can come in a variety of sizes; however typical kits would include one liter or more of tumescent solution. In other embodiments, the tumescent solution may require rehydration or dilution to an administrable concentration.

In one embodiment, a kit can comprise a one liter solution of 0.9% normal saline, 500 mg of cefazolin, 500 mg lidocaine 2%, 1 mg epinephrine, 10 mEq bicarbonate. One of ordinary skill in the art would recognize that several variations in the concentration of lidocaine are possible depending on the intended clinical use. For example, embodiments comprising higher dosages of lidocaine, optionally buffered with additional bicarbonate, can be used when a procedure is to be performed in a sensitive area. Variations on the type and concentration of antibiotic component are also possible. Some embodiments can also include various concentrations of epinephrine or different types of vasoconstrictors. Persons skilled in the art will recognize that many standardized variations are possible and the above example should not be deemed to be limiting.

In some embodiments, the tumescent solution or components for preparing the tumescent solution can be packaged along with a set of cannulae, tubing and possibly other surgical instruments for performing liposuction. Such kits can include an appropriate mix of tumescent solution components for the body part where the procedure is to be performed along with appropriately sized, sterile instruments. In some embodiments, the sterile instruments are capable of interacting with standardized liposuction equipment (i.e., peristaltic pumps, adipose tissue receptacles, etc.). Kits for TLAnti use in mastectomy procedures can be prepared comprising the tumescent solution along with any appropriate instruments.

In some embodiments, the tumescent solution can be provided in prefilled tumescent reservoir bags. Such bags could be manufactured by a pharmaceutical company and be sold as "ready to use." Manufactured tumescent delivery bags are a more efficient and economical use of hospital staff than having to custom mix the tumescent solution for each surgical patient. Further, commercially produced prefilled tumescent reservoir bags would eliminate pharmacist error in mixing and preparing tumescent solution. In one embodiment, a TLAnti solution is provided in a prefilled tumescent reservoir bag comprising a dilute solution of local antibiotic such as lidocaine ($\leq 1$ g/L) or other water soluble antibiotic and a vasoconstrictor, such as epinephrine ($\leq 1$ mg/L) in a physiologic electrolyte solution sodium chloride. TLAnti solutions containing epinephrine can be manufactured at a moderately acidic pH to optimize epinephrine stability. The TLAnti solution can be neutralized prior to administration by the addition of approximately 10-25 mEq of sodium bicarbonate. An appropriate amount of sodium bicarbonate can be included for addition to the prefilled tumescent reservoir bag.

Although TLAnti solution is safe when infiltrated into subcutaneous tissue; rapid, systemic infusion of TLAnti may be lethal. There is thus a need to prevent inadvertent IV administration of tumescent solutions. Various safety features may be incorporated into the prefilled tumescent reservoir bags. Tumescent reservoir bags can be designed to be readily distinguishable from standard IV bags. Distinguishing features include, but are not limited to, unique shape, color-coding, and/or printed warnings. In some embodiments, tumescent reservoir bags may be provided as kits in conjunction with a non-standard (non-luer) connector system to prevent inadvertent connection to an IV line.

Tumescent solution can be injected into the subcutaneous space during surgical procedures using a variety of infiltration cannulae that are well known to persons skilled in performing surgical procedures. In some embodiments, the TLAnti can be injected into the treatment area using an infiltration cannula comprising a flexible cannula, a hub, and a rigid stylet. The flexible cannula has a proximal end and a distal end. The flexible cannula can also have a plurality of apertures disposed in a pattern about the distal end. The apertures are configured to infiltrate fluid into the subcutaneous tissue of a patient. The hub is configured to be held by a person performing the infiltration procedure. The hub has a first end and an opposing second end. The first end is attached to the proximal end of the flexible cannula and the second end includes a connector configured to connect to an input source for receiving the fluid to be infiltrated into the subcutaneous tissue of the patient. The fluid flows from the connector, through the hub and into the flexible cannula.

In some embodiments, the tumescent solution can also be delivered via a disposable catheter that can be used in emergency situations or under conditions when establishing intravenous access is difficult or impossible. In such embodiments, the tumescent solution can be injected into the subcutaneous space via a flexile cannula with a rigid stylet that can be fabricated from stainless metal or rigid plastic. The distal end of the cannula can be closed to cover the tip of the rigid stylet or open with a hole allowing the tip of the rigid stylet to protrude. In some embodiments, the tip of the rigid stylet can be sharp to facilitate the direct insertion through the skin of the patient. Other embodiments comprise a blunt tip requiring a skin incision to permit insertion of the rigid stylet and the cannula into the subcutaneous space. The stylet can be formed to have either a solid or hollow cross-sectional configuration. The hollow rigid stylet may have small holes distributed along its length in a pattern dissimilar or identical to the pattern of holes placed along the flexible cannula into which the stylet is inserted. Thus, in some embodiments, the stylet itself can be used as an infiltration cannula.

Method of Performing Liposuction Using Tumescent Antibiotic Solution

Some embodiments of TLAnti can be used to provide anesthesia, hemostasis, and antibiotic prophylaxis during liposuction or other medical procedures. Liposuction is a well known procedure that is disclosed in U.S. Pat. Nos. 5,052,999 and 5,472,416, the disclosures of which are incorporated herein in their entirety by reference thereto. In the procedure disclosed herein, once the liposuction site is adequately sterilized and prepared, TLAnti is infiltrated into the subcutaneous fat compartment ("infiltration procedure") using a small gauge injection cannula, typically beginning at the location that the practitioner expects to be the deepest portion of adipose tissue removal. This area is filled with a sufficient quantity of TLAnti so that it becomes saturated and swollen or "tumescent." Typically, the operator can recognize whether sufficient TLAnti has been injected during the infiltration procedure if the area appears swollen, pale and relatively cool because of vasoconstriction. Once the practitioner has determined that sufficient TLAnti has been injected, the removal of adipose tissue can begin through a cannula capable of suctioning fat out of the body and into a reservoir. An example of such a procedure, albeit one involving standard tumescent anesthesia without the use of TLAnti is described in Jeffrey A. Klein, Tumescent Technique Chronicles, DERMATOLOGIC SURGERY, vol. 21, pp. 449-457, 1995.

The cannulae typically used in such procedures include a tubular needle portion with proximal and distal ends. In some embodiments, the proximal end of the tubular needle is attached to a hub that is used by the anesthesiologist or surgeon to grasp and hold the cannula during the infiltration procedure. The hub is connected to the tubular needle at a first end and has a connector, such as a luer lock, at an opposing second end. The connector is, in turn, connected to a fluid source, such as tubing connected to a fluid reservoir containing the TLAnti such as an IV bag. The TLAnti enters via the connector. In some embodiments, the distal end of the cannula is sealed and the TLAnti exits the cannula through a plurality of apertures located proximate of the distal end in a linear, helical, or spiral pattern distributed over the distal 33% to 100% of the tubular needle. A detailed description of cannulae of this type can be found in pending U.S. patent application Ser. No. 11/800,355. However, the present disclosure is compatible with a numerous types of cannulae that are capable of being used in the infiltration procedure. Some examples can be found in U.S. Pat. Nos. 4,863,439, 6,336,925 and 7,018,354 the disclosures of which are incorporated by reference in their entirety by reference thereto. Such cannulae are typically connected to a handle and a hollow tube that is operable coupled to a pumping system and receptacle for physiologic tissue and fluids.

In some embodiments, the TLAnti can be withdrawn from the reservoir and injected into the patient manually using a syringe, hand pump or electrical pumping system. In other embodiments, the TLAnti is injected from the reservoir using a peristaltic pump. One example of this type of pump can be found in U.S. Pat. No. 5,236,414, the disclosure of which is incorporated herein in its entirety by reference thereto. Another embodiment of a peristaltic pump that can be used with the current disclosure is described in pending U.S. patent application Ser. No. 11/641,228. Persons skilled in the art will recognize that there are a number of possible mechanisms that can be used to transfer the TLAnti from the reservoir to the subcutaneous fat compartment.

In some embodiments, the same cannula that is used for the removal of adipose tissue can be used for the delivery of TLAnti. In some such embodiments, the cannula can have two lumens, one for incoming adipose tissue and blood and a second lumen for outgoing TLAnti. In other embodiments, such cannulae can have a single lumen that can be used alternatingly for the removal of adipose tissue and the injection of TLAnti. In such embodiments, the practitioner can switch the cannula from a mode wherein incoming adipose tissue and blood is being drawn into the cannula lumen, to an alternative mode wherein TLAnti passes out of the cannula lumen into the subcutaneous fat compartment. An example of such a switching system can be found in U.S. Pat. No. 4,696,669, the disclosure of which is incorporated herein in its entirety by reference thereto. Such embodiments can comprise separate pumping systems, for example, one for incoming tissue and fluid and another for the TLAnti. Other embodiments can utilize a single, reversible pumping system. An example of this technique, albeit one using standard tumescent anesthesia can be found in U.S. Pat. No. 5,472,416 the disclosures of which are incorporated herein in their entirety by reference thereto.

The Use of Tumescent Antibiotics in Mastectomy

TLAnti can be used during mastectomy procedures. The surgical excision of breast cancer is associated with a better prognosis than other therapeutic options such as chemotherapy, immunotherapy, endocrine therapy, or radiation therapy. However, surgery under general anesthesia is associated with significant systemic metabolic, neuroendocrine, and cytokine side-effects which may induce a transient perioperative inhibition of immune function including immune mediated anticancer surveillance thus enabling malignant cells to successfully spread to other parts of the body during the surgical procedure. Local anesthesia using the tumescent technique can reduce or prevent the immunosuppressive effects of general anesthesia. Lumpectomy and mastectomy are safer when performed by tumescent local anesthesia instead of general anesthesia. The tumescent technique also reduces or eliminates the need for postoperative narcotics which can inhibit immune function.

TLAnti can also help to reduce the risk of metastases by preventing malignant cells from entering the bloodstream through a number of mechanisms. The tumescent technique induces profound vasoconstriction, thus providing a physical barrier to malignant cells entering the blood stream and thereby reducing the risk of metastasis to distant organs. In addition, the use of TLAnti can reduce platelet activation which prevents endothelial wall retraction and reduces the likelihood of cancer cells entering the body. The surface of an activated platelet contains newly synthesized bioactive molecules including thromboxane A2 and thrombin. Activated platelets may produce and release products which augment tumor cell survival and decrease the effectiveness of immune surveillance. High localized tissue concentrations of tumescent lidocaine inhibit platelet activation and thereby reduce the risk of surgery-precipitated metastasis.

In some embodiments, TLAnti is administered utilizing the Klein infiltration cannula (Klein cannula) described in pending U.S. patent application Ser. No. 11/800,355. Klein cannulae are sealed on the distal end so that the TLAnti can exit the cannula from a series of apertures on the side of the cannula. This enables the operator to insert the cannula into the target area without the need for the operator to repeatedly push the cannula in and out of the surgical area during the infiltration procedure. By minimizing the amount of trauma to the treatment area and thereby reducing the risk of dislodging tumor cells, the likelihood of precipitating metastasis is reduced. In other embodiments, the procedure can be performed using cannulae other than the Klein cannula.

The use of TLAnti during this procedure also adds the benefit of the administration of antibiotics during the surgical procedure. Just as in the liposuction procedures described above, surgical site infections can be problematic during mastectomy and lumpectomy. In addition to providing anesthesia and reducing the risk of metastasis, TLAnti can help to reduce the risk of surgical site infection. Some embodiments relate to the tumescent delivery of chemotherapeutic agents.

Some embodiments relate to the prevention of chronic pain after mastectomy or other surgical procedures by administration of TLAnti to achieve preemptive analgesia and reduce post-surgical pain. Use of TLAnti along with a Klein cannula can reduce the risk of chronic pain after mastectomy. Post-mastectomy pain syndrome (PMPS) is a common complication of breast surgery. The prevalence rate of PMPS is estimated to be 43%. In a study from Northeast Scotland, of 408 women who reported PMPS in 1996, nearly half continued to experience PMPS at a mean of 9 years after surgery. The most important factor associated with chronic pain and phantom pain after mastectomy is the intensity of acute post-operative pain. This fact suggests that aggressive management of acute postoperative pain may reduce chronic post-mastectomy pain. Preemptive surgical analgesia, such as can be achieved by tumescent delivery of local anesthetic, has been shown to reduce the degree and incidence of significant post-surgical pain. Preincisional paravertebral block (a form of local anesthesia) reduces the prevalence of chronic pain after mastectomy. However paravertebral blocks are relatively difficult achieve, require considerable clinical expertise, and are associated with a relatively high risk of systemic local anesthetic toxicity as a result of inadvertent IV injection. In contrast, the tumescent technique is relatively easy to perform with virtually no risk of toxicity associated with tumescent infiltration using a Klein cannula.

Additional Advantages of Using Tumescent Antibiotics in Surgical Procedures

TLAnti can be used in a variety of surgical procedures. When so employed, TLAnti can also reduce the risk of deep vein thrombosis and post-operative thromboembolism. Thromboembolism, a leading cause of perioperative morbidity and mortality, is the direct result of platelet activation by surgical trauma. There is both clinical and experimental evidence that lidocaine can reduce surgical trauma-associated platelet activation and aggregation. For example, in vivo bleeding volume and bleeding time tests show prolonged bleeding after local subcutaneous infiltration of tumescent local anesthesia containing dilute lidocaine, indicating a decrease in platelet activity. Blood platelet activation is associated with a degranulation and release of vasoactive and thrombogenic chemical mediators including serotonin and thromboxane-A2, which play a role in acute coronary thrombosis and arrhythmias. However, the lidocaine present in the TLAnti solution can affect platelet function by means of several diverse mechanisms: For example, the release of the phospholipid messenger lysophosphatidate from activated platelets is inhibited by the extracellular application of lidocaine in concentrations injected into surgical wounds. In addition, lidocaine may inhibit platelet aggregation by acting on adenosine diphosphate (ADP). Lidocaine, as well as other local anesthetics, benzocaine and bupivacaine, have been shown to inhibit platelet aggregation induced by ADP. In addition, at concentrations much higher than that required to decrease platelet aggregation, lidocaine inhibits the shape change associated with platelet aggregation. The actual mechanism of platelet inhibition by lidocaine is not known. Not wishing to be bound to a particular theory, however, the concentration of calcium ions may play a role in platelet inhibition by lidocaine and other local anesthetics. Lidocaine and bupivacaine have been shown to inhibit lysophosphate signaling, which induces Ca(2+)-activated Cl-currents. Thus, Lidocaine and bupivacaine may act to impair trans-membrane calcium transportation. In addition, there is evidence that increasing the concentration of calcium decreases the inhibitory effect of lidocaine on platelets.

The tumescent drug delivery system, in conjunction with tumescent local anesthesia and tumescent antibiotic delivery, is uniquely able to deliver long-lasting elevated lidocaine concentration to the site of surgical trauma and thereby prevent thromboembolism. Unlike other delivery systems, the tumescent technique is capable of producing sufficient concentrations for lidocaine to achieve its antithrombic effects. At safe systemic concentrations (e.g. ≤6 micrograms/ml) lidocaine seems to have no effect on platelet aggregation. However at tissue concentrations achieved after infiltration of TLAnti there is a significant inhibition of in-vitro platelet aggregation. In-vitro platelet aggregation induced by ADP, epinephrine and collagen is consistently inhibited by lidocaine concentrations equal to or greater than 0.5 mg/ml. The concentration of lidocaine in TLAnti typically ranges from 0.4 mg/ml to 1.2 mg/ml. Furthermore, in-vitro testing of the effect of lidocaine on platelet aggregation has shown that the longer the incubation time with lidocaine, the more efficient the anti-aggregating effect. The local tissue vasoconstriction associated with TLAnti impairs systemic absorption of tumescent lidocaine and dramatically prolongs the local tissue concentrations of lidocaine. Tumescent local anesthesia infiltrated into the site of surgical incision produces very high and prolonged local tissue concentrations of lidocaine and can thereby significantly reduce platelet activation and the risk of perioperative thromboembolism.

It is well known that thromboembolism is a greater risk with surgery under general anesthesia compared to the same surgery under local anesthesia. For example, comparisons of orthopedic surgical procedures of the knee done under general anesthesia versus procedures done under epidural/spinal regional local anesthesia show that the incidence of pulmonary embolism and deep vein thrombosis associated with the procedure is reduced. Lidocaine, a component of the regional local anesthesia used may have contributed to the reduction in thromboembolism observed. Circumstantial evidence also supports the potential role of TLAnti in preventing the occurrence of thromboembolism. When liposuction is performed under general anesthesia, pulmonary embolism is the leading cause of death. However, there have been no reported cases of pulmonary embolism associated with liposuction under tumescent local anesthesia.

In some embodiments, TLAnti may be delivered to the surgical site while the patient is under general anesthesia. Not wishing to be bound by a particular theory, the higher tissue concentration of lidocaine achieved with TLAnti may inhibit platelet function far more effectively than either IV delivery or peripheral nerve block delivery. The preoperative infiltration with of the surgical site with TLAnti enables the lidocaine concentration within surgically traumatized tissues to reach sufficiently high levels for the lidocaine to achieve an antithrombic effect. Thus TLAnti can reduce the risk of perioperative thromboembolic disease such as deep vein thrombosis (DVT) and pulmonary embolism (PE), while the systemic concentrations of lidocaine remain uniformly well below the toxic threshold.

In some embodiments, lidocaine provided in TLAnti may act synergistically with other antibiotics to decrease the risk of surgical site infection. Lidocaine is known to affect nerve conduction by inhibiting cell membrane sodium pumps. Not wishing to be bound to a particular theory, it is likely that lidocaine exerts its antibiotic affect through inhibition of trans-membrane ion transport or antibiotic efflux channels. Synergy between lidocaine and other antibiotics, such as cefazolin or metronidazole, is tested by performing minimum inhibitory concentration (MIC), minimum bactericidal concentration (MBC), and Time-Kill studies involving methacillin-resistant *Staphylococcus aureus, Bacteroides fragilis*, and *Escherichia coli*.

Several embodiments relate to methods and compositions for reducing the risk of thromboembolism by oral administration of lidocaine. The bioavailability of orally administered lidocaine is limited by rapid degradation of lidocaine by cytochrome P450 enzymes. Several embodiments described herein relate to methods of reducing the risk of thromboembolism by oral administration of lidocaine in combination with an inhibitor of cytochrome P450 enzymes. Examples of cytochrome P450 inhibitors include free bases or pharmacologically acceptable salts of: alpha-naphthoflavone, beta-naphthoflavone, apigenin, baicalein, beta-myrcene, catechin, 3-phenylpropyl acetate, formononetin, gallic acid, hesperetin, hesperidin, isoquercitrin, lauryl alcohol, luteolin, luteolin-7-glycoside, narigin, nordihydroguaiaretic acid, quercitrin, swertiamarin, terpineol, and trans-cinnamaldehyde. Lidocaine and one or more cytochrome P450 inhibitors may be administered simultaneously or sequentially.

The Use of Tumescent Antibiotics in Emergency Medical Procedures

TLAnti can be delivered using a disposable, plastic cannula as described in U.S. patent application Ser. No. 11/800,355, the disclosures of which are incorporated herein in their entirety by reference thereto. This device provides a method for relatively rapid fluid resuscitation and the administration of anesthesia and antibiotics in situations wherein establishing intravenous (IV) access is not feasible (e.g., in a remote area, an obese patient with poor venous access, burn/trauma victim, unavailable trained medical professional, etc.). A significant advantage of using the tumescent technique to deliver fluids and medications is that the infiltration procedure is relatively easy to perform. This can make it a particularly valuable technique, for example, in the setting of overwhelming mass casualties where there is no hope or expectation of trained clinical personnel being available. In such cases, the ability of untrained first-responders to provide immediate fluid resuscitation can save many lives. Such situations can include disasters with overwhelming numbers of trauma or burn victims, or when a cholera epidemic results in widespread dysentery and dehydration, in conditions of biological warfare or widespread radiation exposure, etc. It is unlikely that under such conditions, there will be sufficient trained personnel to start an IV line for IV fluid resuscitation. In such a setting, anyone (e.g., an adult of average intelligence with minimal clinical training), perhaps even a victim himself, could simply insert one or more disposable plastic infiltration cannulae directly through the skin on the thigh(s) and into subcutaneous tissue, attach an IV bag and allow the force of gravity to propel the TLAnti into the subcutaneous space in a tumescent fashion. In a setting where rapid systemic absorption of fluids and systemic absorption of antibiotics is critical to resuscitation of a patient with dehydration and an infection, the tumescent antibiotic solution can be modified by eliminating a vasoconstrictor such as epinephrine, and instead adding a vasodilator such as methyl nicotinate. The resulting systemic absorption and redistribution of TLAnti into the intracellular and intravascular compartments could be life-saving.

The tumescent technique performed with disposable catheters and TLAnti provides a useful method of administering fluids and medications to patients when establishing an IV line is difficult or impossible. For example, it can be extremely difficult to obtain IV access among patients who are obese, elderly, have a history of IV drug abuse, or with severe dehydration. By contrast, the subcutaneous infiltration of medications using the tumescent technique can often be achieved relatively easily in many such cases. In such cases, the ability to administer IV fluids, anesthetic, and antibiotics through the alternative subcutaneous route can be invaluable and, at times, lifesaving. The use of tumescent drug delivery for emergency fluid resuscitation when IV access is not feasible has been previously described in U.S. Pat. No. 7,572,613 the disclosure of which is incorporated herein in their entirety by reference thereto.

The tumescent technique can also be useful in certain conditions where various aspects of the environment make IV insertion difficult or impractical. Such conditions could include the treatment of wounded soldiers in night-time combat conditions when establishing an IV access in total darkness is nearly impossible and the use of a flash light might attract enemy fire. It could also be useful in low gravity environments, such as on the International Space Station where a normal gravity-fed IV could not function, but injecting medications subcutaneously using the tumescent technique would not be affected. Cannulae with pre-mixed dosages of TLAnti could be provided in emergency medical kits for use in such conditions if and when the need arises.

Methods of Conducting Pharmacokinetic Measurements of Interstitial Space Fluid

It is important to reach pharmacologically active drug concentrations at the site of action for effective treatment of infectious diseases. Since the interstitial space fluid (ISF) of tissue represents the site of action for a majority of bacterial infections and since only free (unbound) molecules account for the drug effect, direct measurement of the free drug fraction in ISF is desirable. However, it is considerably more challenging to conduct pharmacokinetic measurements of interstitial space fluid (ISF) than serum. For example, measurements of extravascular antibiotic concentrations using excised tissue is problematic because tissue homogenates contain blood, intracellular organelle-bound, and protein-bound drug concentrations, which differ significantly from the concentrations of antibiotics within ISF, which is relatively blood and protein free. Recently, clinical pharmacologic studies of antibiotics have used microdialysis to determine drug concentrations in ISF; however, at present microdialysis technology is complex, expensive and not widely available.

Several embodiments described herein relate to a novel method for conducting pharmakinetic measurements of ISF by sequential sampling of tumescent interstitial space fluid (TISF). Several embodiments relate to a method of conducting pharmakinetic measurements of one or more drugs in ISF comprising obtaining from subcutaneous adipose tissue sequential samples of TISF by hand-held syringe liposuction for a period of time after tumescent delivery of the one or more drugs and measuring the amount of one or more drugs in each sample. In some embodiments, sequential sampling of TISF is conducted hourly, every two hours, every three hours, every four hours, every five hours, every six hours, every seven hours, every eight hours, every nine hours, or every ten hours for up to 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 hours. In some embodiments, the methods described herein may be used to investigate the absorption pharmacokinetics of antibiotics.

Several embodiments described herein relate to a novel method for conducting pharmakinetic measurements of one or more antibiotics in ISF comprising obtaining sequential samples of TISF from subcutaneous adipose tissue by hand-held syringe liposuction for a period of time after tumescent delivery of TLAnti solution and measuring the amount of the one or more antibiotics in each sample. In some embodiments, a sample of TISF is obtained every 5, 10, 15, 20, 25, 30, 35, 40, 45, 50, or 55 minutes after TAD. In some embodiments, a sample of TISF is obtained hourly after TAD. In some embodiments, a sample of TISF is obtained every 2, 3, 4, 5, 6, 7, 8, 9, 10, 11, 12, 13, 14, 15, 16, 17, 18, 19, 20, 21, 22, 23, or 24 hours after TAD. In some embodiments, sequential samples of TISF are obtained for a period of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 hours after TAD. One embodiment relates to a method of conducting pharmakinetic measurements of one or more antibiotics in ISF comprising obtaining a sample of TISF hourly for a period of 10 hours after TAD and measuring the amount of one or more antibiotics in each sample.

Since only free (unbound) antibiotic molecules account for the antimicrobial effect, determination of the free antibiotic fraction in ISF is desirable. The concentration of free (unbound) antibiotic in TISF after tumescent antibiotic delivery can reasonably be assumed to be equivalent to the entire antibiotic content in TISF (i.e., total[TISF]TAD≈free[TISF]TAD) because the antibiotic concentration of TAD solution is high, while the protein content of TISF is low. For intravenous antibiotic delivery, the physiology of molecular osmosis, where free (unbound) antibiotic molecules move without restriction across capillary walls, results in an equilibrium of free antibiotic in the serum and extra-vascular interstitial fluid (ISF) (free[ISF]IVAD≈free[Serum]IVAD).

The methods described herein may be utilized to measure important pharmacokinetic (PK) metrics for bioavailability of drugs, such as antibiotics, within subcutaneous adipose tissue, such PK metrics including: area under the curve of concentration as a function of time (AUC) and the maximum concentration (Cmax) of the drug. The magnitude of the cumulative tissue exposure a tissue over time to a given drug can be measured by determining the AUC of drug concentration within the interstitial fluid (ISF) as a function of time. With regard to the PK metrics of antibiotics, the methods described herein may further be utilized to measure the duration of time that the antibiotic concentration exceeds the minimal inhibitory concentration (MIC) for a specific bacteria (T>MIC).

The methods described herein may be utilized to evaluate the effectiveness of tumescent drug delivery compared to other modes of delivery. For example, in one embodiment, the methods described herein may be utilized to evaluate the effectiveness of tumescent antibiotic delivery (TAD) and intravenous antibiotic delivery (IVAD) for preventing surgical site infection (SSI). Only free (unbound) antibiotic molecules interact with bacteria or diffuse across capillary walls between serum and ISF; thus, for SSI prevention, the most effective modes of antibiotic delivery would result in the greatest free-antibiotic concentration in subcutaneous ISF. Accordingly, TAD is superior to WAD for preventing SSIs where free[ISF]IVAD<free[TISF]TAD. Since the total concentration of antibiotic is equivalent to free (unbound) antibiotic in TISF after tumescent antibiotic delivery and the concentrations of free antibiotic in the serum and ISF are equivalent after WAD, then TAD is superior to IVAD for preventing SSIs where experimental data demonstrates total [Serum]IVAD<total[TISF]TAD.

DEFINITIONS

Adit: a small round hole in the skin (typically 1 mm, 1.5 mm or 2 mm diameter) made by a skin-biopsy punch, and intended to be an access port for percutaneous entry into the subcutaneous fat by a tumescent infiltration cannula and/or a liposuction cannula.

Infiltration: an injection that causes a fluid to permeate or percolate through pores or interstices. Thus an infiltration refers to an injection directly into tissue.

Infusion: an injection that pours a fluid into a place or into (the lumen of a blood) vessel. Thus an infusion refers to an intravascular injection.

Injection: The action of forcing a fluid, etc. into tissue or cavity, as by means of a syringe, or by some impulsive force.

Tumescent Technique, Tumescent Infiltration: The tumescent technique is a method of subcutaneous drug delivery of large volumes of very dilute solution of a medication together with either a dilute vasoconstrictor such as epinephrine or a dilute vasodilator such a methyl nicotinate in an isotonic solution of crystalloid (e.g. physiologic saline, lactated Ringer's solution, Hartman's solution) infiltrated directly into subcutaneous fat or muscle or along the exterior of a length of vein or other tissue to produce either a vasoconstrictor-induced very slow systemic absorption or a vasodilator-induced rapid systemic absorption, as well as direct hydrostatic effect on capillaries, veins, and arterioles. The tumescent technique can be used to deliver large volumes of very dilute medication together with dilute epinephrine in isotonic solution of crystalloid (e.g. physiologic saline, lactated Ringer's solution, Hartman's solution, etc). Inclusion of a vasoconstrictor in the tumescent solution produces very slow systemic absorption as a result of intense subcutaneous vasoconstriction, as well as direct hydrostatic compression of capillaries and veins.

Minimum Bactericidal Concentration (MBC) is the lowest concentration of antibiotic required to kill a particular bacterial isolate in vitro. Antimicrobials are usually regarded as bactericidal if the MBC is no more than four times the MIC.

Minimum Inhibitory Concentration (MIC) is the lowest concentration of an antimicrobial that will inhibit the visible growth of a particular bacterial isolate. Measurements of MIC are used to confirm resistance of microorganisms to an antimicrobial agent and also to monitor the activity of new antimicrobial agents. Clinically, the minimum inhibitory concentrations may be used not only to determine the amount of antibiotic that the patient will receive but also the type of antibiotic used, which prevents the development of microbial resistance to antimicrobial agents.

Tumescent Drug Delivery, Tumescent Delivery: Tumescent drug delivery and synonyms refer to the tumescent technique for delivering a drug into the subcutaneous space. In other words, tumescent delivery is a process of infiltration of very large volumes of very dilute solutions of therapeutic substances dissolved in a crystalloid solution with either a vasoconstrictor such as epinephrine or a vasodilator such as methyl nicotinate into subcutaneous tissue to the point of producing tumescence of the targeted tissue.

Tumescent Local Anesthesia (TLA) is local anesthesia produced by direct infiltration into subcutaneous tissue of large volumes of dilute local anesthetic.

Tumescent Local Anesthetic Solution (TLA Solution) is the local anesthetic solution used to produce TLA. Several embodiments relate to a TLA solution comprising an antibiotic component, an anesthetic component, a vasoconstrictor component and a solvent. In some embodiments, TLA Solution consists of a 10 to 20 fold dilution of commercially available concentration of lidocaine and epinephrine. In one embodiment, TLA Solution comprises very dilute lidocaine ≤1 gram/liter) and epinephrine (≤1 milligram/liter) with sodium bicarbonate (10 milliequivalents/liter) in a crystalloid solution such as physiologic saline or lactated Ringer's solution. Typically the volume of TLA Solution infiltrated into the target tissue is so large that the skin and subcutaneous tissue becomes tumescent, in other words swollen and firm.

As used herein, the terms "tumescent local antibiotic solution," "TLAnti solution," "tumescent antibiotic delivery solution," or "TAD solution," may be used interchangeably to refer to a solution comprising an antibiotic component, an anesthetic component, a vasoconstrictor component and a solvent/pharmaceutically acceptable carrier.

Tumescent, tumescence: swollen and firm.

Tumescent liposuction: liposuction performed by local anesthesia using tumescent local anesthesia.

Tumescent fluid, tumescent solution: dilute solutions of therapeutic substances dissolved in an aqueous solvent, such as crystalloid solution, intended for tumescent delivery into subcutaneous tissue.

Tumescent "drug": the "drug" in the context as an ingredient in a tumescent solution and its pharmacokinetic behavior as a result of the pharmacokinetics of a tumescent solution; for example tumescent lidocaine, tumescent epinephrine, tumescent antibiotic.

Tumescent Pharmacokinetics: The absorption pharmacokinetics (the pharmacologic and physiologic factors associated with the systemic absorption of a drug) after tumescent infiltration of a drug is either dramatically slower with a vasoconstrictor such as epinephrine or dramatically faster with a vasodilator such as methyl nicotinate than the rate of systemic absorption of routine injection of the drug. In some embodiments, the intense vasoconstriction induced by epinephrine, slows the rate of drug absorption into the central circulation and prolongs the local effects of the drug. For example, the duration of routine local anesthesia with lidocaine is typically 2 hours; in contrast the duration of tumescent local anesthesia may be 12 to 18 hours or more. A similar prolonged effect of tumescent antibiotic infiltration significantly improves the prophylactic effect of preoperative antibiotic therapy in the prevention of surgical site infections.

As used herein, the term "[FLUID]MODE" refers to the concentration of an antibiotic in a specified FLUID, for example, interstitial fluid, blood serum, whole blood, amniotic fluid, aqueous humour, breast milk, cerebrospinal fluid, lymph, peritoneal fluid, pleural fluid, saliva, sweat, mucus, etc., after a specified MODE of drug delivery. Examples of MODES of drug delivery include, but are not limited to ingestion, topical administration, transmuscosal administration, inhalation, injection, intravenous administration, intrarterial administration, intramuscular administration, intraosseous administration, intrathecal administration, intraperitoneal administration, intravesical administration, intravitreal administration, intradermal administration, and tumescent administration. As used herein, [ISF]IVAD and [Serum]IVAD represent the antibiotic concentration in interstitial fluid (ISF) and serum, respectively, after IVAD. Similarly, [TISF]TAD and [Serum]TAD refer to the antibiotic concentrations in TISF and serum after TAD.

As used herein, the term "bound[FLUID]MODE" refers to the concentration of protein bound antibiotic in the specified FLUID after delivery by a specified MODE.

As used herein, the term "free[FLUID]MODE" refers to the concentration of free antibiotic (not bound to protein) in the specified FLUID after delivery by a specified MODE.

As used herein, the term "pharmacodynamic quantity" refers to a quantitative measure of drug effect in terms of drug concentration as a function of time. For example, the terms "area under the curve (AUC)" and "time to Cmax" refer to pharmacokinetic quantities.

As used herein, the term "Cmax" refers to the peak antibiotic concentration in a tissue after drug delivery. As used herein, the term "Cmax[FLUID]MODE" refers to the peak antibiotic concentration in a specified FLUID after delivery by a specified MODE.

As used herein, the term "T(Cmax)" refers to the time from initiation of antibiotic delivery to the time when Cmax is achieved.

As used herein, T>MIC refers to the length of time during which the antibiotic concentration exceeds the Minimum Inhibitory Concentration (MIC) for a given bacteria. As used herein, T[TISF]TAD>MIC refers to the length of time the antibiotic concentration exceeds the MIC for a given bacteria in Tumescent Interstitial Space Fluid (TISF) after TAD.

As used herein, the term "interstitial space fluid (ISF)" refers to an extracellular and extravascular fluid that fills the spaces between most of the cells of the body. ISF is relatively blood and protein free.

As used herein, the term "Tumescent Interstitial Space Fluid (TISF)" refers to a mixture of a small volume of ISF and a larger volume of tumescently-delivered solution, for example, TLA Solution, TLAnti Solution, TAD solution, etc., said mixture resulting from tumescent infiltration. Immediately after tumescent infiltration, TISF is chemically equivalent to the TAD solution.

As used herein, the term "Minimum Inhibitory Concentration (MIC)" refers to the lowest concentration of an antimicrobial that will inhibit the visible growth of a microorganism after overnight incubation. MIC is a function of both the bacteria and the antibiotic under consideration.

As used herein, the term "area under the curve (AUC)" is a pharmacokinetic term that refers to drug concentration as a function of time following drug delivery. AUC is calculated from the area under the plot of body fluid concentration of drug (not logarithm of the concentration) against time after drug administration. The AUC is of particular use in estimating bioavailability of drugs, and in estimating total clearance of drugs. Area under the curve (AUC) of drug concentration within blood or tissue as a function of time is a pharmacokinetic metric for measuring the magnitude of the cumulative tissue exposure over time to a given drug. Whenever drug concentration is measured continuously then AUC is defined as AUC=$\int_0^{t_n} C(t)dt$ evaluated from time t=0 to $t_n$. Whenever drug concentration is measured at discrete time points $\{t_0, t_1, t_2, \ldots, t_n\}$, AUC can be estimated using the trapezoid rule:

$$AUC = \sum_{i=1}^{i=n} \frac{[C(ti) + C(t(i-1))]}{2} (t(i) - t(i-1)).$$

As used herein, the term "AUC[FLUID]MODE" refers to the AUC of the drug in a specified body FLUID by a specified MODE. For example, the term "AUC[ISF]TAD" refers to the AUC in interstitial space fluid of the drug administered by tumescent delivery; the term "AUC[Serum]TAD" refers to the AUC in serum of the drug administered by tumescent delivery; the term "AUC[ISF]IVAD" refers to the AUC in interstitial space fluid of the drug administered by IV delivery; and the term "AUC[Serum]TAD" refers to the AUC in serum of the drug administered by IV delivery.

Each antibiotic has a characteristic fraction of its total concentration which is bound to proteins. Only free antibiotic molecules interact with bacteria or diffuse across capillary walls between serum and ISF. As used herein, the term "freeAUC[TISF]TAD" refers to the AUC of free (unbound) antibiotic in ISF after TAD. As used herein, the term "totalAUC[Serum]IVAD" refers to the AUC of total (bound and unbound) antibiotic in Serum after IVAD. Similarly, a fraction of an antibiotic in ISF is protein bound.

As used herein, the term "patient" refers to the recipient of a therapeutic treatment and includes all organisms within kingdom animalia. In preferred embodiments, the animal is within the family of mammals, such as humans, bovine, ovine, porcine, feline, buffalo, canine, goat, equine, donkey, deer and primates. The most preferred animal is human.

As used herein, the terms "treat" "treating" and "treatment" include "prevent" "preventing" and "prevention" respectively. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The term "effective amount" includes an amount effective, at dosages and for periods of time necessary, to achieve the desired result, e.g., sufficient to prevent thromboembolism or infection. An effective amount of TLAnti or other tumescent solution may vary according to factors such as the disease state, age, and weight of the subject, and the ability of TLAnti or other tumescent solution to elicit a desired response in the subject. Dosage regimens may be adjusted to provide the optimum therapeutic response. An effective amount is also one in which any toxic or detrimental effects (e.g., side effects) of TLAnti or other tumescent solution are outweighed by the therapeutically beneficial effects. The language "a prophylactically effective amount" of TLAnti refers to an amount of TLAnti which is effective, upon single or multiple dose administration to the subject, in preventing or treating infection or thromboembolism.

All documents, or portions of documents, cited in this application, including but not limited to patents, patent applications, articles, books, and treatises, are hereby expressly incorporated by reference in their entirety for any purpose.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved.

As used herein, an "increase" or "decrease" in a measurement, unless otherwise specified, is typically in comparison to a baseline value. For example, an increase in time to hospitalization for subjects undergoing treatment may be in comparison to a baseline value of time to hospitalization for subjects that are not undergoing such treatment. In some instances an increase or decrease in a measurement can be evaluated based on the context in which the term is used.

The following are provided for illustrative purposes only, and are in no way intended to limit the scope of the present invention.

EXAMPLES

Example 1

Clinical Evaluation of Tumescent Antibiotic Delivery

With IRB-approval, 4 subjects received Cefazolin IV Antibiotic Delivery (IVAD) or Tumescent Antibiotic Delivery (TAD) on repeated occasions. One patient received Metronidazole and Cefazolin.

TAD was achieved using blunt-tipped Monty infiltration cannulae and peristaltic tumescent infiltration pump. Treated areas included: abdomen (Patient 1 & Patient 4); female breasts (Patient 2); and hips-outer thighs (Patient 3). Patient 4 received Cefazolin and Metronidazole.

Figure 8:
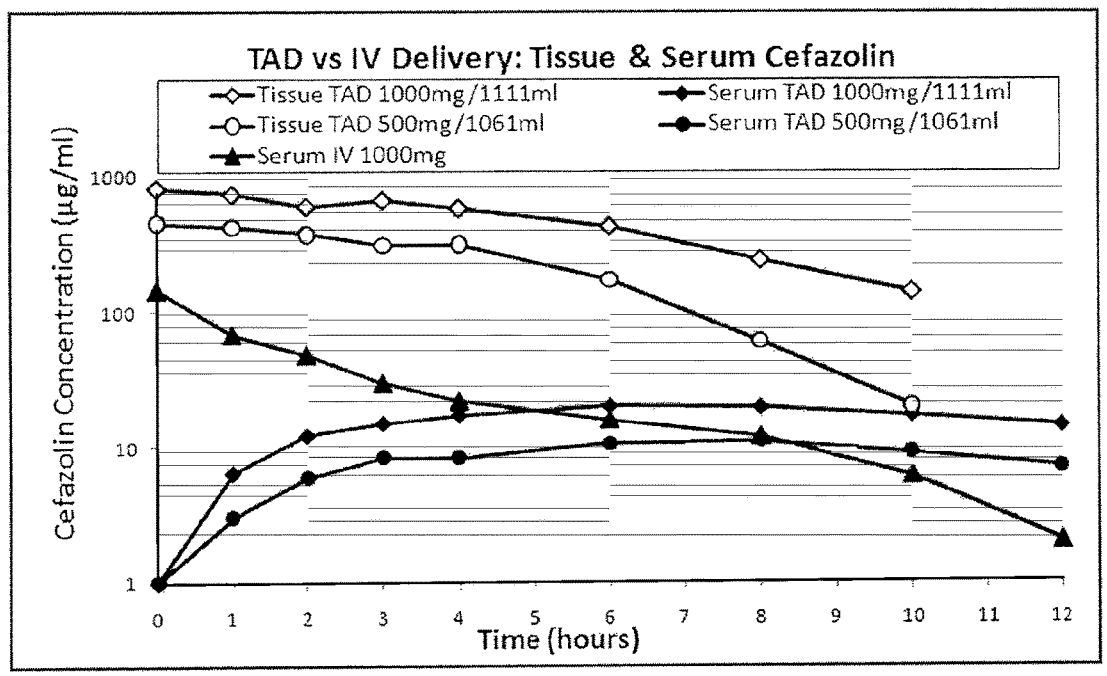
FIG. 8 shows the results of a comparison study of tumescent antibiotic delivery (TAD) versus IV delivery of Cefazolin.
Figure 9:
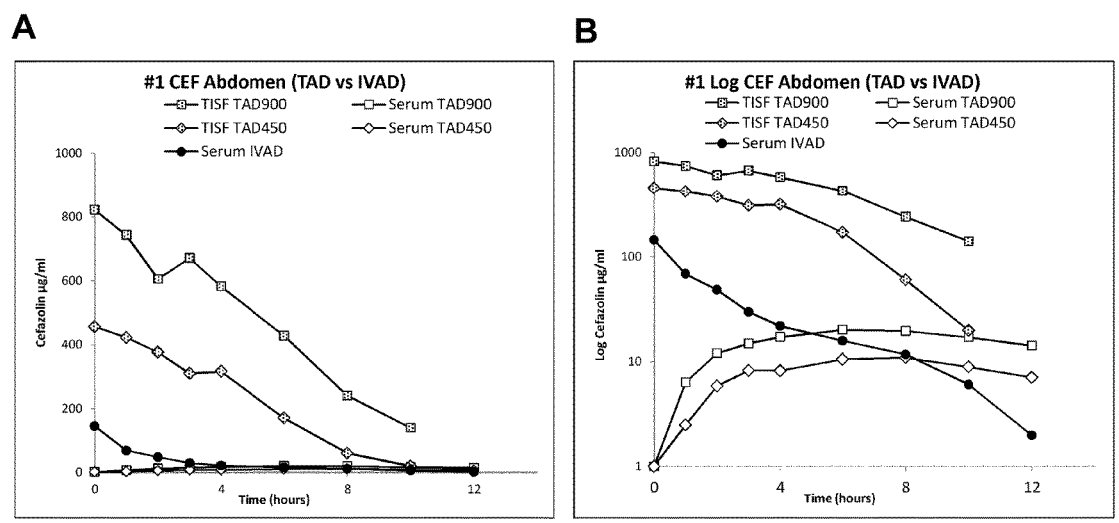
FIG. 9 shows graphs depicting the results of a pharmakinetic study comparing tumescent delivery of cefazolin to the abdomen and IV delivery. A total dose of 1 gm Cefazolin was administered by IV (IVAD) or by tumescent delivery (TAD) of cefazolin in 900 mg/ml or 450 mg/ml TAD solution. (A) shows a linear scale graph and (B) shows a log scale graph of area under the curve (AUC) of cefazolin concentration in tumescent subcutaneous interstitial fluid (TISF) and serum as a function of time.
Figure 10:
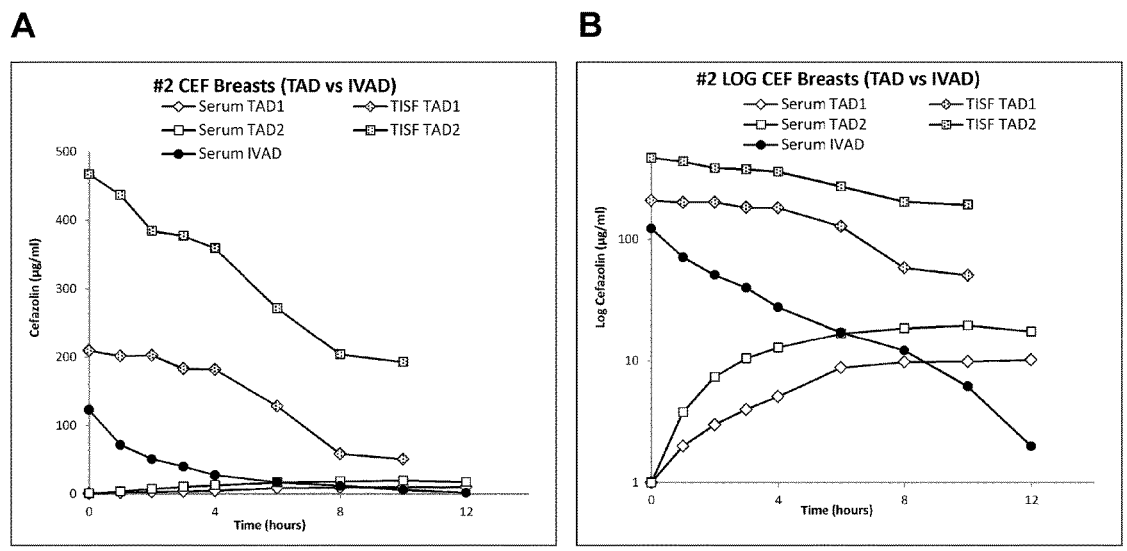
FIG. 10 shows graphs depicting the results of a pharmakinetic study comparing tumescent delivery of cefazolin to the breast and IV delivery. (A) shows a linear scale graph and (B) shows a log scale graph of AUC concentration of cefazolin in TISF and serum as a function of time for 1 gm IVAD cefazolin, 500 mg TAD cefazolin (225 mg/L TAD solution) and 1 gm TAD cefazolin (450 mg/L TAD solution).
Figure 11:
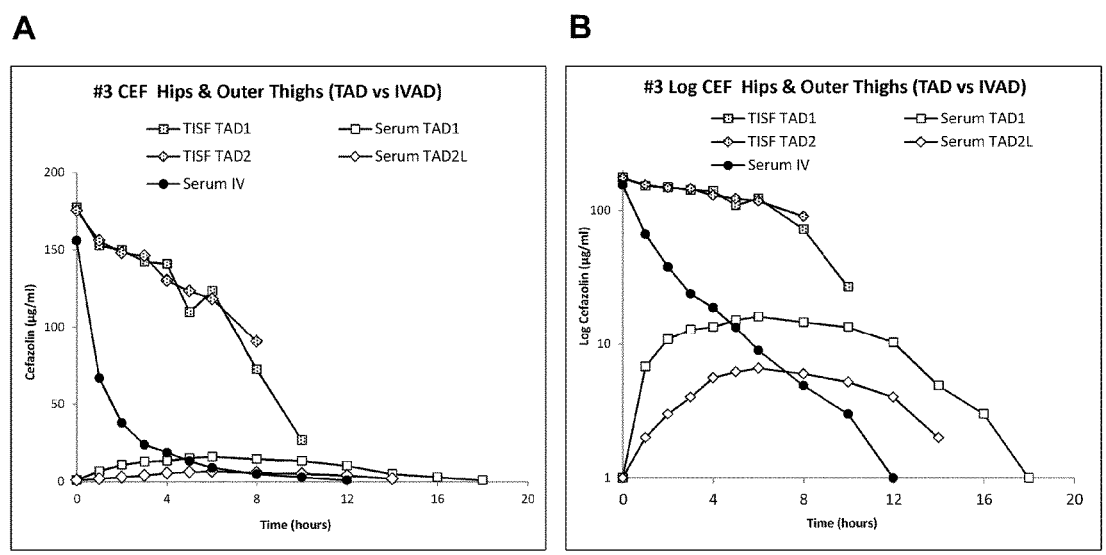
FIG. 11 shows graphs depicting the results of a pharmakinetic study comparing tumescent delivery of cefazolin to the hips and outer thighs and IV delivery. (A) shows a linear scale graph and (B) shows a log scale graph of AUC concentration of cefazolin in TISF and serum as a function of time for 1 gm IVAD cefazolin, 870 mg TAD cefazolin (228 mg/L TAD solution) and 435 mg TAD cefazolin (228 mg/L TAD solution).
Figure 12:
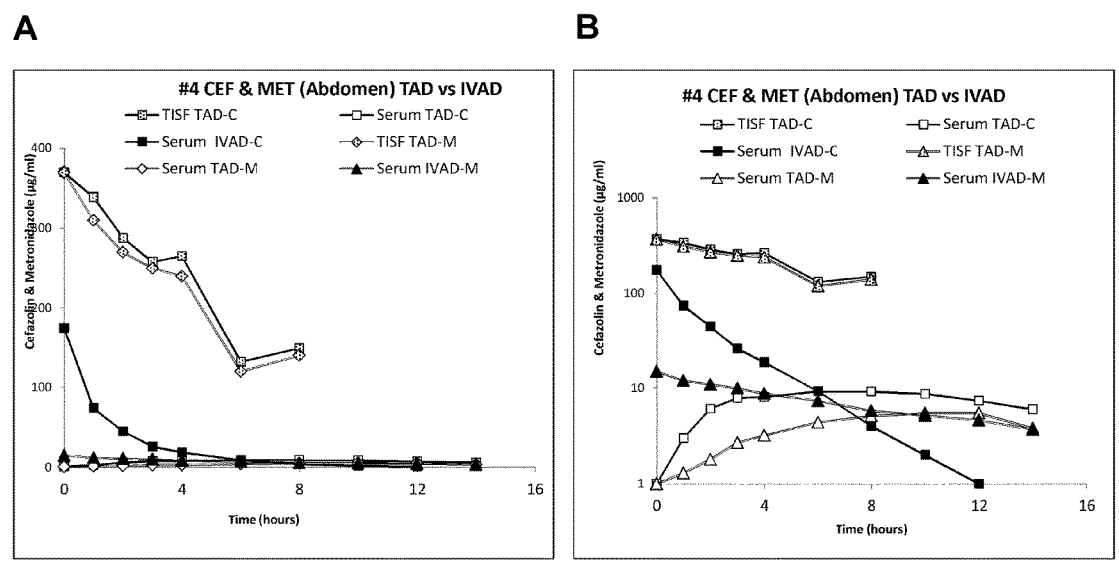
FIG. 12 shows graphs depicting the results of a pharmakinetic study comparing tumescent delivery of cefazolin and metronidazole to the abdomen with IV delivery. (A) shows a linear scale graph and (B) shows a log scale graph of AUC concentration of cefazolin and metronidazole in TISF and serum as a function of time for 500 mg cefazolin by IVAD, 500 mg metronidazole by IVAD, and 500 mg each of cefazolin and metronidazole in a 1211 ml TAD solution (413 mg/L TAD solution).
Figure 13:
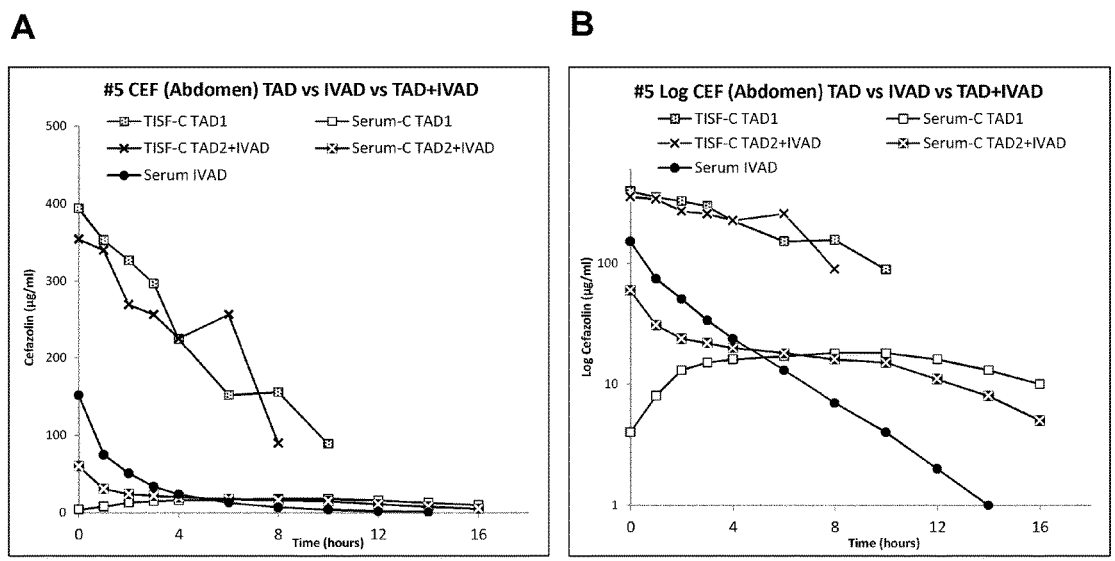
FIG. 13 shows graphs depicting the results of a pharmakinetic study of cefazolin concentration over time after IVAD, abdominal TAD and abdominal TAD in combination with IVAD. (A) is a linear scale graph and (B) is a log scale graph showing sequential AUC cefazolin concentrations in TISF after delivery of 1.2 gm cefazolin by TAD (345 mg/L TAD solution); in serum after delivery of 1.2 gm cefazolin by IVAD; and in TISF and serum after delivery of 800 mg cefazolin by TAD (400 mg/L TAD solution) administered simultaneously with 400 mg cefazolin by IVAD.
Figure 14:
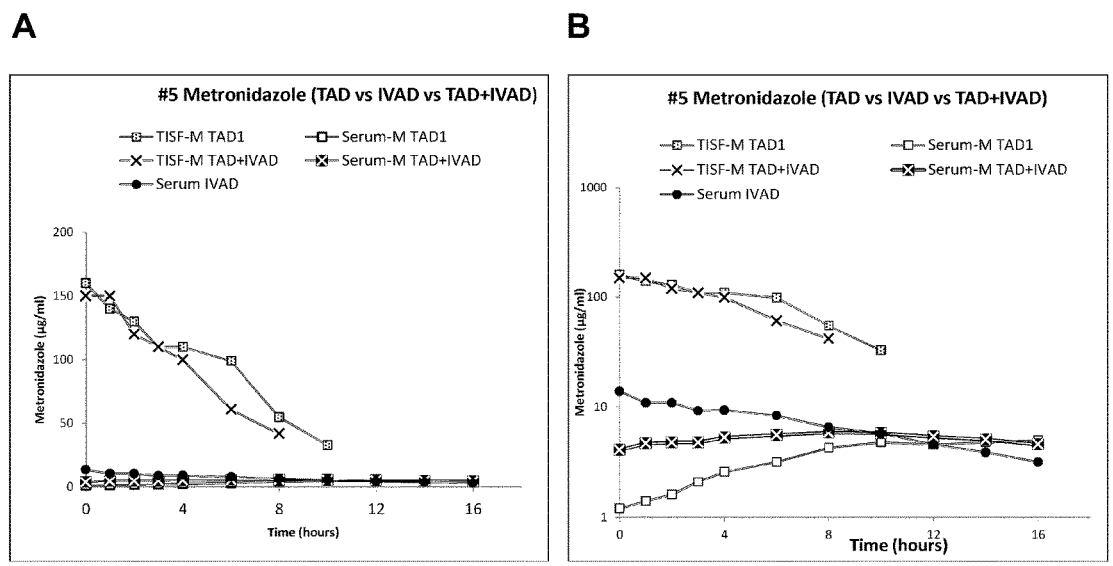
FIG. 14 shows graphs depicting the results of a pharmakinetic study of metronidazole concentration over time after IVAD, abdominal TAD and abdominal TAD in combination with IVAD. (A) is a linear scale graph and (B) is a log scale graph showing sequential AUC metronidazole concentrations in TISF after delivery of 600 mg metronidazole by TAD (172 mg/L TAD solution); in serum after delivery of 600 mg metronidazole by IVAD; and in TISF and serum after delivery of 400 mg metronidazole by TAD (200 mg/L TAD solution) administered simultaneously with 200 mg metronidazole by IVAD.
Figure 15:
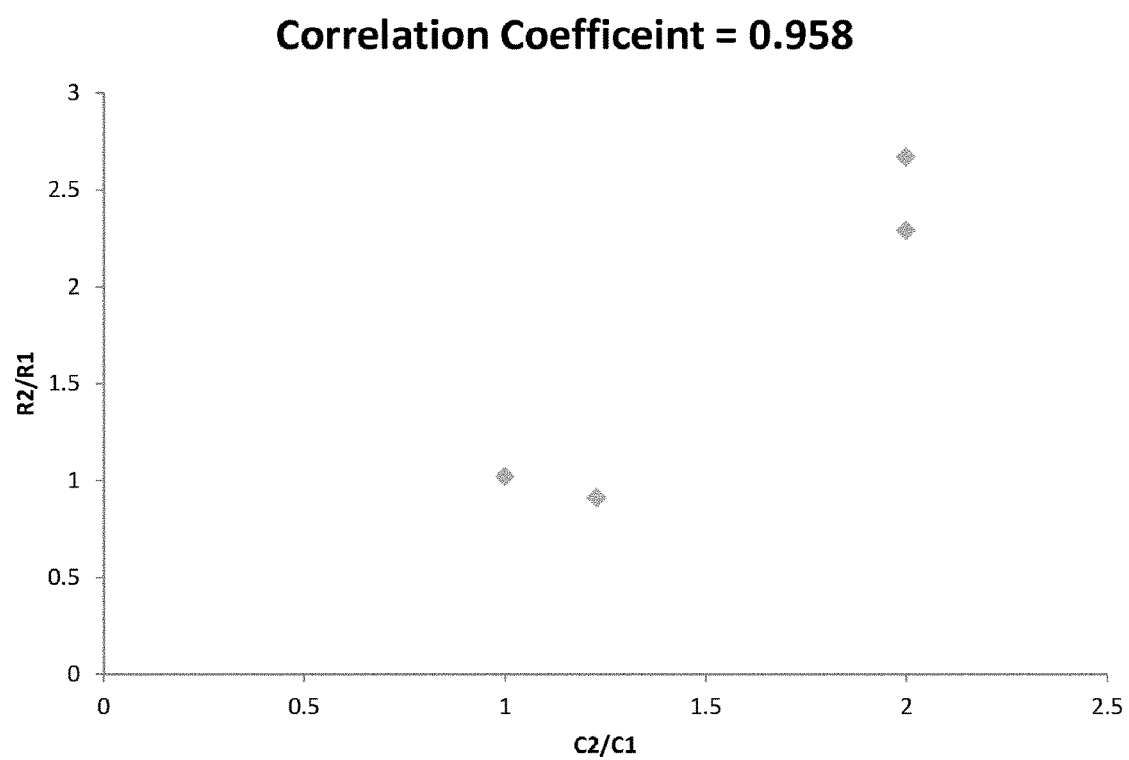
FIG. 15 is a scatter diagram of four of the cefazolin studies involving two TAD procedures. C2/C1 on the X axis shows the mg/L cefazolin concentration in the two TAD solutions and R2/R1 on the Y axis shows the cumulative exposure of the interstitial fluid to cefazolin after TAD in terms of $AUC_1[TISF]_{TAD}$ and $AUC_2[TISF]_{TAD}$.
Figure 16:
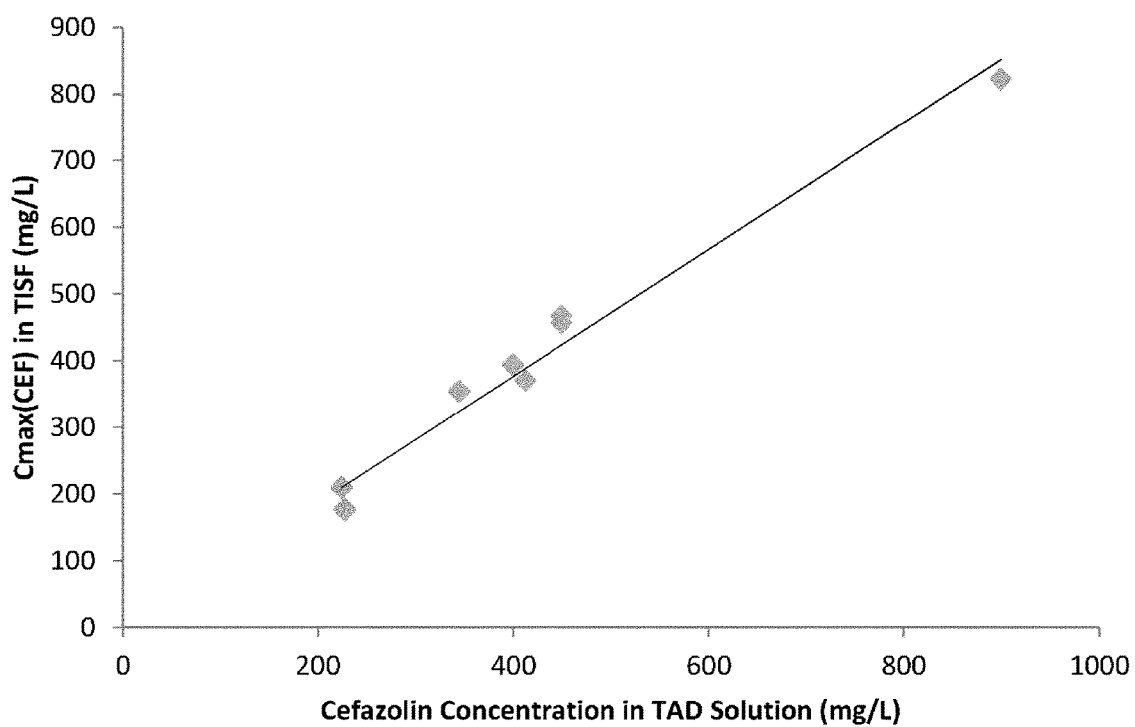
FIG. 16 depicts a graph showing the correlation between the concentration of cefazolin in TAD solution (mg/L) on the X axis and the concentration of cefazolin in TISF ($C_{max}$ mg/L) on the Y axis.

After TAD or IVAD treatment, blood was sampled at 1 to 2 hour intervals for a period of ≥12 hours. After TAD treatment, samples of subcutaneous fat/tumescent fluid were aspirated by hand-held syringe-liposuction at 1 to 2 hrs for a period of ≥8 hrs. Samples were centrifuged. Serum and subcutaneous interstitial tissue fluid were assayed for Cefazolin or Metronidazole by HPLC. Results are shown in FIG. 8.

Patient 1 was studied on 3 separate occasions with treatments occurring at least one week apart. Patient 1 was treated with: TAD 1000 mg Cefazolin/1111 ml; TAD 500 mg Cefazolin/1061 ml; or IVAD 1000 mg Cefazolin. The 10 hour Cefazolin AUC and Cmax for TAD (abdomen) and IVAD treatments for Patient 1 are shown in Table 1. Other patients studied gave similar results (not shown).

TABLE 1

| 10 HOUR CEFAZOLIN AUC AND CMAX FOR TAD (ABDOMEN) & IVAD | | |
|---|---|---|
| Sample | AUC | Cmax |
| Subcutaneous Cefazolin (TAD 1000 mg) | 4782 | 823 |
| Subcutaneous Cefazolin (TAD 500 mg) | 2280 | 456 |
| Serum Cefazolin (TAD 1000 mg) | 167 | 20 |
| Serum Cefazolin (TAD 500 mg) | 82 | 11 |
| Serum Cefazolin (IV 1000 mg) | 315 | 146 |

AUC Ratio TAD 1000 mg: IV 1000 mg = 4782/315 = 15.2
AUC Ratio TAD 500 mg: IV 1000 mg = 2280/315 = 7.2

In conclusion, subcutaneous tissue fluid AUC for TAD 1000 mg Cefazolin and TAD 500 mg Cefazolin yielded 15.2 and 7.2 times AUC, respectively, compared to IVAD 1000 mg Cefazolin (assuming Cefazolin concentration in subcutaneous tissue after IVAD is less than or equal to the concomitant Cefazolin concentration in serum). In serum, TAD yields reduced AUC & Cmax, while prolonging duration of serum Cefazolin compared to IVAD. Based on unique pharmacokinetic absorption characteristics, antibiotic surgical site infection prophylaxis by TAD may be better and have fewer risks compared to the current standard of care, IVAD.

Example 2

Evaluation of Antimicrobial Activity of Lidocaine and Cefazolin by Determination of Minimum Inhibitory Concentration and Minimum Bactericidal Concentration The bactericidal properties of three antimicrobial compounds (Cefazolin, Lidocaine and Lidocaine+Cefazolin) were evaluated by measuring the Minimum Inhibitory Concentration (MIC) and Minimum Bactericidal Concentration for *Staphylococcus aureus* (MRSA) ATCC 33592.

A standardized suspension of *Staphylococcus aureus* (MRSA) ATCC 33592 was prepared by culturing on tryptic soy agar for 3-5 days at 35° C. The agar slant was washed with sterile phosphate buffer solution and the organism concentration was adjusted. Innoculum levels of *Staphylococcus aureus* (MRSA) ATCC 33592 were between $4.4 \times 10^5$ to $4.7 \times 10^5$ CFU/ml.

In order to determine Minimum Inhibitory Concentrations (MIC) of Lidocaine, Cefazolin, and Lidocaine+Cefazolin standardized suspensions of *Staphylococcus aureus* (MRSA) ATCC 33592 were added into separate 10 ml aliquots of varied concentrations of Lidocaine, Cefazolin, and Lidocaine plus Cefazolin. Following inoculation, survival of test microorganisms was determined. This method of determining MIC was based on the method described in the NCCLS document M7: Methods for Dilution Antimicrobial Susceptibility Tests for Bacteria that Grow Aerobically; Approved Standard—Seventh Edition. The results of MIC analysis are summarized in Tables 2-7.

TABLE 2

DAY 1 RESULTS OF MINIMUM INHIBITORY CONCENTRATION (MIC) OF CEFAZOLIN VS. MRSA

| | Cefazolin Concentration (mg/L) | | | | | | | | | | Positive Control | Sterility |
|---|---|---|---|---|---|---|---|---|---|---|---|---|
| | 1000 | 500 | 250 | 125 | 62.5 | 31.25 | 15.6 | 7.8 | 3.9 | 1.95 | | |
| MRSA 4.7 × 10$^5$ CFU/ml | ○ | ○ | ○ | ○ | + | + | + | + | + | + | | |
| MRSA 4.7 × 10$^5$ CFU/ml | ○ | ○ | ○ | ○ | + | + | + | + | + | + | | |
| Cefazolin Only | ○ | ○ | ○ | ○ | ○ | ○ | ○ | ○ | ○ | ○ | | |
| MRSA Only 4.7 × 10$^5$ CFU/ml | + | + | + | + | + | + | + | + | + | + | | |
| Controls | | | | | | | | | | | + | ○ |

Legend:
+ = Positive
○ = Negative

TABLE 3

DAY 2 RESULTS OF MINIMUM INHIBITORY CONCENTRATION (MIC) OF CEFAZOLIN VS. MRSA

| | Cefazolin Concentration (mg/L) | | | | | | | | | | Positive Control | Sterility |
|---|---|---|---|---|---|---|---|---|---|---|---|---|
| | 8000 | 4000 | 2000 | 1000 | 500 | 250 | 125 | 62.5 | 31.25 | 15.6 | | |
| MRSA 4.4 × 10$^5$ CFU/ml | ○ | ○ | ○ | ○ | ○ | ○ | + | + | + | + | | |
| MRSA 4.4 × 10$^5$ CFU/ml | ○ | ○ | ○ | ○ | ○ | ○ | + | + | + | + | | |
| Cefazolin Only | ○ | ○ | ○ | ○ | ○ | ○ | ○ | ○ | ○ | ○ | | |
| MRSA Only 4.4 × 10$^5$ CFU/ml | + | + | + | + | + | + | + | + | + | + | | |
| Controls | | | | | | | | | | | + | ○ |

Legend:
+ = Positive
○ = Negative

TABLE 4

DAY 1 RESULTS OF MINIMUM INHIBITORY CONCENTRATION (MIC) OF LIDOCAINE VS. MRSA

| | Lidocaine Concentration (mg/L) | | | | | | | | | | Positive Control | Sterility |
|---|---|---|---|---|---|---|---|---|---|---|---|---|
| | 1000 | 500 | 250 | 125 | 62.5 | 31.25 | 15.6 | 7.8 | 3.9 | 1.95 | | |
| MRSA 4.7 × 10$^5$ CFU/ml | + | + | + | + | + | + | + | + | + | + | | |
| MRSA 4.7 × 10$^5$ CFU/ml | + | + | + | + | + | + | + | + | + | + | | |
| Lidocaine Only | ○ | ○ | ○ | ○ | ○ | ○ | ○ | ○ | ○ | ○ | | |
| MRSA Only 4.7 × 10$^5$ CFU/ml | + | + | + | + | + | + | + | + | + | + | | |
| Controls | | | | | | | | | | | + | ○ |

Legend:
+ = Positive
○ = Negative

TABLE 5

DAY 2 RESULTS OF MINIMUM INHIBITORY CONCENTRATION (MIC) OF LIDOCAINE VS. MRSA

| | Lidocaine Concentration (mg/L) | | | | | | | | | | Positive Control | Sterility |
|---|---|---|---|---|---|---|---|---|---|---|---|---|
| | 10000 | 5000 | 2500 | 1250 | 625 | 312.5 | 156 | 78 | 39 | 19.5 | | |
| MRSA 4.4 × 10⁵ CFU/ml | ○ | ○ | + | + | + | + | + | + | + | + | | |
| MRSA 4.4 × 10⁵ CFU/ml | ○ | ○ | + | + | + | + | + | + | + | + | | |
| Lidocaine Only | ○ | ○ | ○ | ○ | ○ | ○ | ○ | ○ | ○ | ○ | | |
| MRSA Only 4.4 × 10⁵ CFU/ml | + | + | + | + | + | + | + | + | + | + | | |
| Controls | | | | | | | | | | | + | ○ |

Legend:
+ = Positive
○ = Negative

TABLE 6

DAY 1 RESULTS OF MINIMUM INHIBITORY CONCENTRATION (MIC) LIDOCAINE (1000 mg/L) + CEFAZOLIN vs. MRSA

| | Cefazolin Concentration (mg/L) | | | | | | | | | | Positive Control | Sterility |
|---|---|---|---|---|---|---|---|---|---|---|---|---|
| | 200 | 100 | 50 | 25 | 12.5 | 6.25 | 3.125 | 1.56 | 0.78 | 0.39 | | |
| MRSA 4.4 × 10⁵ CFU/ml | ○ | ○ | + | + | + | + | + | + | + | + | | |
| MRSA 4.4 × 10⁵ CFU/ml | ○ | ○ | + | + | + | + | + | + | + | + | | |
| Lidocaine + Cefazolin Only | ○ | ○ | ○ | ○ | ○ | ○ | ○ | ○ | ○ | ○ | | |
| MRSA Only 4.4 × 10⁵ CFU/ml | + | + | + | + | + | + | + | + | + | + | | |
| Controls | | | | | | | | | | | + | ○ |

Legend:
+ = Positive
○ = Negative

TABLE 7

DAY 2 RESULTS OF MINIMUM INHIBITORY CONCENTRATION (MIC) OF LIDOCAINE (1000 mg/L) + CEFAZOLIN VS. MRSA

| | Cefazolin Concentration (mg/L) | | | | | | | | | | Positive Control | Sterility |
|---|---|---|---|---|---|---|---|---|---|---|---|---|
| | 200 | 100 | 50 | 25 | 12.5 | 6.25 | 3.125 | 1.56 | 0.78 | 0.39 | | |
| MRSA 4.6 × 10⁵ CFU/ml | ○ | + | + | + | + | + | + | + | + | + | | |
| MRSA 4.6 × 10⁵ CFU/ml | ○ | + | + | + | + | + | + | + | + | + | | |
| Lidocaine + Cefazolin Only | ○ | ○ | ○ | ○ | ○ | ○ | ○ | ○ | ○ | ○ | | |
| MRSA Only 4.6 × 10⁵ CFU/ml | + | + | + | + | + | + | + | + | + | + | | |
| Controls | | | | | | | | | | | + | ○ |

Legend:
+ = Positive
○ = Negative

Table 8 shows the results of the analysis of the Minimum Bactericidal Concentration (MBC) of Lidocaine, Cefazolin, and Lidocaine+Cefazolin. Determinations of MBC followed the method described in "Report on the Working Party on Antibiotic Sensitivity Testing of the British Society of Antimicrobial Chemotherapy: A Guide to Sensitivity Testing."

TABLE 8

MINIMUM BACTERICIDAL CONCENTRATION (BAC)

| Test Compound | Day | Concentration (mg/L) | | |
|---|---|---|---|---|
| | | 250 | 125 | 62.5 |
| Cefazolin | 1 (MRSA Inoculum 4.7 × $10^5$ CFU/ml) | 0 | + | + |
| Cefazolin | 2 (MRSA Inoculum 4.4 × $10^5$ CFU/ml) | 0 | + | + |

| Test Compound | Day | Concentration (mg/L) | | |
|---|---|---|---|---|
| | | 10,000 | 5,000 | 1,000 |
| Lidocaine | 1 (MRSA Inoculum 4.7 × $10^5$ CFU/ml) | NA | NA | + |
| Lidocaine | 2 (MRSA Inoculum 4.4 × $10^5$ CFU/ml) | 0 | + | + |

TABLE 8-continued

MINIMUM BACTERICIDAL CONCENTRATION (BAC)

| Test Compound | Day | Concentration (mg/L) | | |
|---|---|---|---|---|
| | | 200 | 100 | 50 |
| Cefazolin + Lidocaine (1000 mg/L) | 1 (MRSA Inoculum 4.4 × $10^5$ CFU/ml) | 0 | + | + |
| Cefazolin + Lidocaine (1000 mg/L) | 2 (MRSA Inoculum 4.6 × $10^5$ CFU/ml) | 0 | 0 | + |

Legend:
+ = Positive
O = Negative

Endpoints were achieved for all 3 test products, Lidocaine, Cefazolin, and Lidocaine+Cefazolin, evaluated in the MIC and MBC study. The MIC endpoints are shown in Table 9 and the MBC endpoints are shown in Table 10. The results of this evaluation indicate that the MIC for Cefazolin is between 125 and 250 mg/L, Lidocaine was around 5,000 mg/L and the combination of both Cefazolin and Lidocaine had an MIC of 100 mg/L. The slight reduction in the MIC and MBC endpoints for the combined (Lidocaine+Cefazolin) test product indicated that the potency of the Cefazolin was not inhibited by the presence of Lidocaine against MRSA (ATCC #33592). All controls met the criteria established for a valid test.

TABLE 9

MIC END POINTS

| Challenge Organism | Cefazolin | | Lidocaine | | Cefazolin + Lidocaine (1000 mg/L) | |
|---|---|---|---|---|---|---|
| | Day 1 | Day 2 | Day 1 | Day 2 | Day 1 | Day 2 |
| Staphylococcus aureus (MRSA) ATCC 33592 | 125 mg/L | 250 mg/L | NA* | 5000 mg/L | 100 mg/L | 100 mg/L |

*Growth present in all wells/dilutions. No endpoint could be determined on Day 1.

TABLE 10

MBC END POINTS

| Challenge Organism | Cefazolin | | Lidocaine | | Cefazolin + Lidocaine (1000 mg/L) | |
|---|---|---|---|---|---|---|
| | Day 1 | Day 2 | Day 1 | Day 2 | Day 1 | Day 2 |
| Staphylococcus aureus (MRSA) ATCC 33592 | 250 mg/L | 250 mg/L | NA* | 10,000 mg/L | 100 mg/L | 200 mg/L |

*No endpoint could be determined on Day 1.

Example 3

Tumescent Antibiotic Delivery in Treatment of Infection

A patient presenting with a localized infection characterized by a central abscess and inflammation is treated by tumescent antibiotic delivery to the affected area. A solution of 250 mg of cefazolin (150 ml from a solution consisting of 500 mg of cefazolin), 300 mg lidocaine. 0.3 mg epinephrine, 3 meq sodium bicarbonate is dissolved in saline to a total volume of 280 ml. The solution is then infiltrated in the area of inflammation. The patient is examined approximately 12-24 hours after infiltration for visible evidence of inflammation and/or redness.

Example 4

Prophylactic Tumescent Antibiotic Delivery to a Surgical Site of a Patient Under General Anesthesia TLAnti is administered to the subcutaneous compartment of a surgical site in a 70 kg adult patient under general anesthesia. The patient is subsequently monitored for perioperative and postoperative thromboembolism.

Example 5

Prophylactic Tumescent Antibiotic Delivery to a Surgical Site of a Patient without General Anesthesia TLAnti is administered to the subcutaneous compartment of a surgical site or site of other injury in a 70 kg adult patient without general anesthesia. The patient is subsequently monitored for perioperative and postoperative thromboembolism.

Example 6

Tumescent Antibiotic Delivery in Treatment of Infection

TLAnti is administered to the subcutaneous compartment at a site of infection in a 70 kg adult patient without general anesthesia. The concentrations of the antibiotic component and anesthetic component used in TLAnti for the treatment of infection exceed concentrations considered safe for systemic use. The progress of the infection is subsequently monitored in the treated patient.

Example 7

Tumescent Antibiotic Delivery in Surgical Treatment of Breast Cancer

A catheter is inserted into the surgical site and the area infiltrated with a tumescent solution. The tumescent solution comprising 0.9% normal saline, 500 mg of cefazolin, 500 mg lidocaine 2%, 1 mg epinephrine, and 10 mEq bicarbonate. Once sufficient anesthesia is achieved, the surgeon removes cancerous tissue with sufficient margins to ensure complete removal of the tumor. The site can subsequently be closed and dressed.

Example 8

Comparison of Tumescent Antibiotic Delivery (TAD) Vs. IV Antibiotic Delivery (IVAD) in Reducing the Risk of Surgical Site Infections (SSI)

Two modes of antibiotic delivery, Tumescent Antibiotic Delivery (TAD) and IV Antibiotic Delivery (IVAD), are compared in their ability to reduce the risk of infection following inoculation with *Staphylococcus aureus*.

Solutions of cefazolin are prepared for TAD and IVAD. When a single route of delivery of cefazolin is used (either IVAD or TAD), the total dosage of antibiotic is equal to 250 mg/kg. When both routes of delivery are used (both IVAD & TAD), the total dosage of antibiotic is equal to 250 mg/kg; however, the relative IVAD and TAD dosages may vary. In this protocol, the relative dosages of antibiotic delivered via IVAD and TAD are 125 mg/kg each.

Eighty rats are anesthetized and their backs shaved and cleansed. Groups of 20 rats each are given a 250 mg/kg dose of cefazolin either by subcutaneous tumescent administration (TAD), intraperitoneal injection (IVAD), or a combination of TAD and IVAD 15 to 35 minutes prior to making a 4 cm sterile vertical incision through the skin of the back into the subcutaneous tissue. The incisions are then immediately inoculated with *Staphylococcus aureus* at concentrations of $10^2$, $10^3$, $10^4$ or $10^5$ organisms per ml and closed. As controls, one group of 10 rats is untreated prior to undergoing incision and inoculation as described above and one group of 10 rats is given a 250 mg/kg dose of cefazolin by a combination of TAD and IVAD prior to incision, but the incision is closed without inoculation. Four days after surgery, the rats are euthanized and samples of 1 $cm^2$ of tissue from the lateral side of the incisions is collected for microbiological assessment.

The collected tissue is weighed and placed in individual sterile tubes containing 1 ml of sterile tryptic soybean broth (TBS). The tissue is homogenized and four 1:10 serial dilutions of each homogenate with 0.5-ml aliquots and diluted with 4.5 ml of sterile TSB: $10^{-1}$ to $10^4$ are made. Blood agar plates are inoculated with 0.1 ml of each dilution and the plates are incubated at 35° C. for 18 to 24 hours. On each plate containing 30-300 CFU the colonies are counted and the number of CFU per gram of tissue is calculated using the formula described in Barron E J, Peterson L R, Finegold S M, Catalase-positive gram positive-cocci, *Staphylococcus, Micrococcus*, and similar organisms. Baily and Scott's Diagnostic Microbiology, $9^{th}$ ed., St Louis Mo.: Mosby 1994. p. 284-95. One-way ANOVA statistical analysis is performed to determine the effectiveness of TAD vs. IVAD in reducing the risk of infections.

Example 9

Ability of Lidocaine in Tumescent Local Anesthesia to Impair Platelet Activation The Duke method of determining bleeding time is used to assess effect of tumescent administration of TLAnti comprising 0.5 mg/ml lidocaine on hemostatic function (platelet response to injury and functional capacity of vasoconstriction).

The skin of the left and right thigh of a subject is cleaned and allowed to dry. A 1 liter solution of TLAnti comprising 0.9% normal saline, 500 mg of cefazolin, 500 mg lidocaine 2%, 1 mg epinephrine, 10 mEq bicarbonate is infiltrated into the subcutaneous tissue of the left thigh until the skin becomes swollen and taught—tumescent. Simultaneous 4 mm deep puncture wounds are made to the same area of the left and right thighs with disposable lancets. The puncture sites are blotted with filter paper every 30 seconds, until bleeding stops and the bleeding time for each thigh is recorded. The bleeding times of the left and right thigh are compared to determine if administration of TLAnti increases bleeding time. Normal bleeding time measured by the Duke method is 1 to 3 minutes.

In a preliminary experiment, bleeding time and bleeding area were measured in a patient before and after tumescent lidocaine exposure. The results are shown in Table 11. There was essentially no change in Average Bleeding Time (BT). In contrast, there was a 40% increase in Average Bleeding Area (BA). Bleeding Area (BA) was a more sensitive and a more specific test for platelet function compared to Bleeding Time (BT). Thus, this pilot study provides the hypothesis that tumescent lidocaine may impair platelet function and may decrease the risk of post-op thromboembolism. In otherwords, TAD may reduce the risk of both post-operative surgical site infection and post-operative thromboembolism.

TABLE 11

COMPARING PRE-OP CONTROLS TO POST-OP
TUMESCENT LIDOCAINE EXPOSURE

| Pt# | Name last first | Test # | Bleeding Time BT x 2 | Bleeding Area BA |
|---|---|---|---|---|
| 1 | Rivera-Me | T1 Control | 12 | 579.42 |
| 1 | Rivera-Me | T2 Control | 12 | 502.52 |
|   |           |            | Control BT = 6 | Control BA = 541 |
| 1 | Rivera-Me | T3 Lidocaine | 10 | 791.81 |
| 1 | Rivera-Me | T4 Lidocaine | 13 | 726.03 |
|   |           |              | Lidocaine BT = 5.75 | Lidocaine BA = 759 |

Example 10

Pharmacokinetics of Tumescent Antibiotic Delivery (Cefazolin and Metronidazole) in Preventing Surgical Site Infections The time from surgical incision until wound closure is when bacterial contamination is most likely to occur. Surgical site infections (SSIs) increase morbidity, length of hospitalization, and hospital costs. SSIs can be devastating for patients and a tremendous financial burden on a health care system. The incidence of SSI among certain common clean and clean-contaminated surgical procedures ranges from 1% to 11%, respectively. The Center for Disease Control (CDC) has defined 3 classes of surgical site infection (SSI): 1) Superficial Incisional SSI, an infection involving skin or subcutaneous tissue within 30 days of surgery; 2) Deep Incisional SSI, an infection involving fascia and muscle layers within 30 days after surgery without an implant or 1 year if an implant is left in place and the infection appears to be related to the surgery and the incision; and 3) Organ/Space SSI, an infection involving any organ or spaces opened and manipulated during the surgery occurring within 30 days of surgery without an implant or 1 year if an implant is left in place and the infection appears to be related to the surgery and the infection.

Prevention of SSI by antibiotics depends upon the concentration profile of the antibiotic (magnitude and duration) within the interstitial space fluid (ISF) at the site of potential bacterial contamination. In turn, antibiotic concentration in ISF depends upon the mode of antibiotic delivery and the total dose of antibiotic. The area under the curve of concentration as a function of time (AUC), the maximum concentration (Cmax) and the duration of time that the antibiotic concentration exceeds the MIC for specific bacteria (T>MIC) are important pharmacokinetic (PK) metrics for bioavailability of antibiotics within subcutaneous adipose tissue. The mode of antibiotic delivery with the greatest AUC, Cmax and T>MIC in subcutaneous tissue is expected to be the most effective at preventing surgical incision site infections.

Modes of Antibiotic Delivery

Most pharmacokinetic studies of antibiotics for SSI prevention consider only one mode of antibiotic delivery, intravenous antibiotic delivery (IVAD). A common metric used to quantitatively compare cumulative antibiotic exposure in different clinical situations after IVAD is the penetration ratio (P) of an antibiotic from serum into subcutaneous ISF, where P=freeAUC[ISF]IVAD/freeAUC[SERUM]IVAD. Penetration ratios can be used to compare different drugs or different formulations of the same drug after IVAD. Antibiotic penetration ratio varies widely between different patients and between different tissues and is decreased by surgery, diabetes and obesity. For example, the penetration of an antibiotic is quantitatively different after IVAD among obese patients compared to normal patients.

Peri-incisional or intra-incisional injection of antibiotics has been found to reduce the risk of SSI compared to IVAD. Such techniques for local delivery of antibiotics involve the infiltration of small volumes of antibiotic solution, resulting in a minimal reservoir effect and minimal dispersion into adjacent tissue. Antibiotic solutions introduced by peri-incisional or intra-incisional injection, which do not contain a vasoconstrictor drug like epinephrine, are rapidly absorbed with rapid decline of antibiotic concentrations within the targeted tissue. The small volumes of antibiotic solutions introduced by peri-incisional or intra-incisional injection do not produce hyper-hydration of the targeted tissues or prevent wound surface desiccation, which impairs migration of neutrophils and macrophages onto the wound surface. Despite some evidence that peri-incisional or intra-incisional injection of antibiotics can reduce SSI risk, such techniques are not used for SSI prophylaxis and consensus opinion suggests that subcutaneous administration of antibiotics for SSI prophylaxis shows "unreliable results and therefore should be avoided as far as possible." See Stratchounski L S, Taylor E W, Dellinger E P, Pechere J C. Antibiotic policies in surgery: a consensus paper. Int J Antimicrob Agents 26:312-322, 2005.

Unlike peri-incisional or intra-incisional antibiotic injection, tumescent antibiotic delivery (TAD) involves the infiltration of a relatively large volume of an antibiotic-containing solution into the subcutaneous compartment, such that the surrounding tissue becomes swollen and firm, i.e., tumescent. A TAD solution comprises one or more antibiotics dissolved in tumescent local anesthesia (TLA), which comprises relatively large volumes of dilute lidocaine ($\leq 1$ grams/L), epinephrine ($\leq 1$ milligrams/L), sodium bicarbonate (10 milliequivalents/L) in physiologic saline or lactated Ringer's solution. The physical and physiologic effects of infiltrating a TAD solution are identical to the effects of a solution of TLA and include prolonged and profound local anesthesia, extensive local epinephrine-induced capillary and venous constriction for surgical hemostasis, hydrostatic pressure-induced capillary and venous compression, inhibition of incisional-trauma-induced platelet activation and delayed systemic absorption of solution components, for example, lidocaine and antibiotics.

The spread of tumescent fluid within subcutaneous tissue occurs by means of rapid bulk flow through the interstitial gel substance. Efficient infiltration of up to five liters of solution or more into subcutaneous fat may be facilitated by use of specialized infiltration cannulas, peristaltic infiltration pumps and tubing. Equilibration of ISF pressures results in a uniform distribution of tumescent fluid throughout the infiltrated tissues. A process of detumescence occurs during 1 to 2 hours following infiltration. The rate of systemic absorption of antibiotics from tumescent subcutaneous tissue is slow as a result of wide spread tumescent vasoconstriction. TAD produces a prolonged large-volume subcutaneous reservoir of an antibiotic solution within a mass of vasoconsticted local tissues. The pharmacokinetic behavior of this reservoir is analogous to a slow-release oral tablet or a slow constant IV Infusion.

Tumescent techniques were developed for local delivery of to enable liposuction to be done totally by local anesthesia. Tumescent local anesthesia (TLA) produces profound surgical local anesthesia persisting for more than 6 to 8 hours with peak serum lidocaine concentrations occurring between 10 to 16 hours after completion of the subcutaneous infiltration. In contrast, 1% or 2% commercial concentrations of lidocaine with epinephrine reliably provide local anesthesia for 2 to 3 hours or less. Because of its prolonged local anesthesia and profound local vasoconstriction, tumescent local anesthesia (TLA) has become the standard of care for a number of surgical procedures limited to skin, subcutaneous tissue, or vascular structures including liposuction totally by local anesthesia, endovenous laser ablation of large leg-vein venous varicosities, skin grafting in burn patients. TLA has been successfully be used for mastectomy and subclavian steal syndrome repair totally by local anesthesia in patients who were not good candidates for general anesthesia. When TLA is used for liposuction the maximum safe mg/kg dosage of tumescent lidocaine is 45 mg/kg to 55 mg/kg. In adults, the maximum safe mg/kg dosage of tumescent lidocaine for TLA without liposuction is estimated to be 30 mg/kg, while the current dosage limitation approved by the FDA for infiltration local anesthesia using commercial lidocaine (1%=10 gm/L) with epinephrine (1:100,000=10 mg/L) is 7 mg/kg.

A clinical pharmacologic investigation was conducted to compare the pharmacokinetic advantages of two modes of systemic antibiotic delivery, Tumescent antibiotic delivery (TAD), which involves the delivery of a relatively large volume of an antibiotic-containing solution to the subcutaneous compartment, and intravenous antibiotic delivery (IVAD), which results in direct delivery of antibiotics to the blood stream, for prophylaxis of SSI. The antibiotics, cefazolin and metronidazole, were chosen for this study because cefazolin is inexpensive and effective against most skin pathogens and metronidazole is inexpensive and effective against GI anaerobic pathogens. The mode of systemic antibiotic delivery providing the most effective antibiotic concentration at a surgical incision site was determined by examining sequential antibiotic concentrations within tumescent subcutaneous interstitial fluid (TISF) and in serum.

Methods

With Institutional Review Board (IRB) approval, the absorption pharmacokinetics of tumescent antibiotic delivery (TAD) and intravenous antibiotic delivery (IVAD) were tested in human subjects and the antibiotic delivery modes were evaluated with respect to the area under the curve (AUC) of antibiotic concentration as a function of time and peak antibiotic concentration (Cmax) in serum and TISF. 4 female subjects participated in at least one study, one subject volunteered for 2 separate studies. 5 studies were conducted: 3 involved TAD to the abdomen, 1 involved TAD to the hips and outer thighs and 1 involved TAD to the breasts. In 3 of the 5 studies, cefazolin was administered and in 2 of the 5 studies cefazolin and metronidazole were administered in combination. Each of the 5 studies consisted of 2 to 3 pharmacokinetic procedures, for a total of 14 procedures. Any procedures conducted on an individual subject were separated by at least one week. In 13 procedures only IVAD or TAD, was used. In one procedure both IVAD and TAD were used concurrently, with IVAD started and finished within five minutes after completing TAD. Results of the studies are shown in FIGS. 9-16.

Antibiotic solutions for tumescent delivery were formulated according to Tables 12 (cefazolin) and 13 (cefazolin and metronidazole). The TAD solutions containing cefazolin were prepared by withdrawing 10 ml from a 1 liter IV bag of TLA and injecting it into a vial containing powdered cefazolin. After the cefazolin was completely dissolved, the 10 ml containing cefazolin was re-injected into the bag of TLA thereby converting the TLA solution into a TAD solution of cefazolin. TAD bags containing metronidazole were prepared by adding metronidazole, available as 500 mg dissolved in 100 ml of saline, to a TAD bag already containing cefazolin. This procedure was varied in one study in order that the ultimate volume of the TAD solution per bag was precisely 1 L: Matching volumes of saline were removed from the 1 L bag of saline before adding solutions of lidocaine, epinephrine, sodium bicarbonate and metronidazole.

TABLE 12

DOSE: CEFAZOLIN & TLA LIDOCAINE

| Cefazolin (CEF) | Study 1-Abdomen | | Study 2-Bilateral Breasts | | Study 3-Hips & Outer Thigh(s) | |
|---|---|---|---|---|---|---|
| | TAD-900 | TAD-450 | TAD-225 | TAD-450 | TAD-870 | TAD-435 |
| Lidocaine 1% | 1 gm in 100 ml | 500 mg in 100 ml | 1 gm in 100 ml | 1 gm in 100 ml | 850 mg in 85 ml | 850 mg in 85 ml |
| Epinephrine 1:1000 | 1 ml | 1 ml | 1 ml | 1 ml | 0.85 ml | 0.85 ml |
| Sodium Bicarb 1 mEq/ml | 10 ml | 10 ml | 10 ml | 10 ml | 10 ml | 10 ml |
| Physiologic saline 0.9% | 1000 ml | 1000 ml | 1000 ml | 1000 ml | 1,000 ml | 1,000 ml |
| Total volume per bag | 1,111 ml | 1,111 ml | 1,111 ml | 1,111 ml | 1,096 ml | 1,096 ml |
| Total Volume Infiltrated | 1,111 ml | 2,222 ml | 2,222 ml | 2,222 ml | 3,774 ml | 1,887 ml |
| [Lidocaine] Conc. in TAD | 900 mg/L | 900 gm/L | 900 mg/L | 900 mg/L | 775 mg/L | 775 mg/L |
| [Epinephrine] Conc. in TAD | 0.9 mg/L | 0.9 mg/L | 0.9 mg/L | 0.9 mg/L | 0.77 mg/L | 0.77 mg/L |
| TLA Lidocaine dose (mg) | 900 mg/L | 1,800 mg | 1,800 mg | 1,800 mg | | |
| TLA Lidocaine dosage (mg/kg) | 13.45 mg/kg | 26.9 mg/kg | 26.2 mg/kg | 26.2 mg/kg | 44 mg/kg | 22 mg/kg |
| Patients weight (kg) | 74.3 kg | | 76.4 kg | | 66.4 kg | |
| Cefazolin IVAD dose (mg) | 1 gm | | 1 gm | | 1 gm | |
| Cefazolin TAD dose (mg) | 1 gm | 1 gm | 1 gm | 500 mg | 870 mg | 435 mg |
| [Cefazolin] Conc in TAD | 900 mg/L | 450 mg/L | 450 mg/L | 225 mg/L | 228 mg/L | 228 mg/L |

TABLE 13

DOSE: CEFAZOLIN, METRONIDAZOLE & TLA LIDOCAINE

| | Study 4 (Abdomen) | Study 5 (Abdomen) | |
|---|---|---|---|
| | TAD | TAD1 | TAD2 + IVAD |
| Lidocaine 1% | 1 gm in 100 ml | 1 gm in 100 ml | 1 gm in 100 ml |
| Epinephrine 1:1000 | 1 ml | 1 ml | 1 ml |
| Sodium bicarbonate 1 mEq/ml | 10 ml | 10 ml | 10 ml |
| Physiologic saline 0.9% | 1000 ml | 1000 ml | 809 ml |
| Total volume per bag | 1,211 ml | 1,221 ml | 1000 ml |
| Total Volume Infiltrated | 1,211 ml | 3,483 ml | 2000 ml |
| [Lidocaine] Conc. in TAD | 825 mg/L | 819 mg/L | 1 gm/L |
| [Epinephrine] Conc. in TAD | 0.83 mg/L | 0.82 mg/L | 1 mg/L |
| Cefazolin TAD dose (mg) | 500 mg | 1,200 mg | 400 mg IVAD + 800 mg TAD |
| [Cefazolin] Conc. in TAD | 413 mg/L | 345 mg/L | 400 mg/L |
| Cefazolin IVAD dose (mg) | 500 mg | 1,200 mg | |
| Metronidazole TAD dose (mg) | 500 mg in 100 ml | 600 mg in 1200 ml | 200 mg IVAD + 400 mg/2 L TAD |
| [Metronidazole] Conc. in TAD | 413 mg/L | 172 mg/L | 200 mg/L |
| Metronidazole IVADdose (mg) | 500 mg | 600 mg | |
| Patients weight (kg) | 66.4 kg | 83 kg | |
| TLA Lidocaine dosage (mg/kg) | 15.1 mg/kg | 34.4 mg/kg | 24.1 mg/kg |

TAD was conducted as described herein. Following TAD, sequential 10 ml samples of tumescent adipose tissue were obtained using a hand-held syringe-liposuction technique. Sampling began immediately after completing the TAD infiltration (T0), and continuing until the patients reported significant discomfort. Liposuction aspirate samples were obtained at 0, 1, 2, 3, 4, 6, and 8 hours in all procedures; in 4 TAD procedures, sampling continued until 10 hours. Sequential serum samples for measurement of antibiotic concentration in serum after TAD ([Serum]TAD) were obtained simultaneously.

For IVAD, the antibiotic was delivered into an antecubital vein. Following IVAD, serum samples were taken from the contralateral arm via an indwelling venous catheter beginning immediately after completion of the antibiotic delivery (T0). Sequential serum samples for measurement of [Serum] IVAD were obtained every one to two hours for up to 12 to 16 hours, for example, at hours 0, 1, 2, 3, 4, 6, 8, 10, 12, and 14 hours.

The samples of liposuction aspirate were centrifuged to obtain infranatant TISF, which comprises minimally blood-tinged tissue-free residual tumescent solution. Serum and TISF samples were assayed for cefazolin and/or metronidazole by high pressure liquid chromatography or high pressure flame chromatography.

AUC (Area Under the Curve) of drug concentration as a function of time, a metric for measuring the cumulative exposure to an individual drug within a specified tissue, was estimated for time T0 to time Tn using the trapezoid rule:

$$AUC = \sum_{i=1}^{i=n} \frac{[C(ti) + C(t(i-1))]}{2}(t(i) - t(i-1)),$$

based on the concentration of cefazolin and/or metronidazole in TISF and serum sampled at discrete time points $\{t_0, t_1, t_2, \ldots, t_n\}$. For the purpose of comparing outcomes of different AUCs, an estimate of $AUC[0,\infty]$, where $AUC[0,\infty] = AUC[0,Tn] + AUC[Tn,\infty]$, was calculated as the area of a triangle having Height $C(Tn)$=antibiotic concentration at time Tn and Base (TN−Tn) where TN is the graphically estimated earliest time where $C(TN)=0$, based on the fact that the elimination rate of an antibiotic from TISF is approximately a constant. Cmax in serum after TAD was determined by the total mg-dose of antibiotic contained within the TAD solution. The calculated AUC and Cmax values for the studies are shown in Tables 14 and 15.

TABLE 14

CONCENTRATION: CEFAZOLIN & TLA LIDOCAINE

| | Study 1-Abdomen | | Study 2-Bilateral Breasts | | Study 3-Hips & Outer Thigh(s) | |
|---|---|---|---|---|---|---|
| Cefazolin (CEF) | TAD-900 | TAD-450 | TAD-225 | TAD-450 | TAD-870 | TAD-435 |
| Cefazolin IVAD dose (mg) | 1 gm | | 1 gm | | 1 gm | |
| Cefazolin TAD dose (mg) | 1 gm | 1 gm | 1 gm | 500 mg | 870 mg | 435 mg |
| [Cefazolin] Conc in TAD | 900 mg/L | 450 mg/L | 450 mg/L | 225 mg/L | 228 mg/L | 228 mg/L |
| Cmax[Serum]IVAD | 146.1 mg/L | | 123.3 mg/L | | 156 mg/L | |
| Cmax[TISF]TAD | 822.7 mg/L | 456.8 mg | 467.4 mg | 209.4 mg | 175.3 mg | 177.2 mg |
| Cma[Serum]TAD | 20.2 mg/L | 11 mg/L | 19.8 mg/L | 10.2 mg/L | 16.2 mg/L | 6.6 mg/L |
| AUC[TISF]TAD | 5349 | 2339 | 4071 | 1586.6 | 1196 | 1332 |
| AUC[Serum]TAD | 245.8 | 111.6 | 239.9 | 114.5 | 178 | 64.6 |
| AUC[Serum]IVAD | 324.2 | 324.2 | 124.3 | 124.3 | 270.6 | 270.6 |
| ER1 = AUC[TISF]TAD/ AUC[Serum]IVAD | 16.5 | 7.21 | 17 | 12.8 | 4.42 | 4.92 |
| ER2 = AUC[Serum]TAD/ AUC[Serum]IVAD | 0.76 | 0.34 | 1.93 | 0.92 | 0.66 | 0.24 |

TABLE 14-continued

CONCENTRATION: CEFAZOLIN & TLA LIDOCAINE

|  | Study 1-Abdomen | | Study 2-Bilateral Breasts | | Study 3-Hips & Outer Thigh(s) | |
| --- | --- | --- | --- | --- | --- | --- |
| Cefazolin (CEF) | TAD-900 | TAD-450 | TAD-225 | TAD-450 | TAD-870 | TAD-435 |
| ER = ER1/ER2 = AUC[TISF]TAD/ AUC[Serum]TAD | 21.8 | 20.9 | 8.8 | 13.9 | 6.72 | 20.6 |

TABLE 15

CONCENTRATION: CEFAZOLIN, METRONIDAZOLE & TLA LIDOCAINE

|  | Study 4 (Abdomen) | Study 5 (Abdomen) | |
| --- | --- | --- | --- |
|  | TAD | TAD1 | TAD2 + IVAD |
| CEF | | | |
| Cefazolin TAD dose (mg) | 500 mg | 1,200 mg | 400 mg IVAD + 800 mg TAD |
| [Cefazolin] Conc, in TAD | 413 mg/L | 345 mg/L | 400 mg/L |
| Cefazolin IVAD dose (mg) | 500 mg | 1,200 mg | |
| AUC[TISF]TAD | 2580.5 | 2484 | 2257 |
| AUC[Serum]TAD | 129 | 144 | 288 |
| AUC[Serum]IVAD | 292.2 | 325 | 325 |
| ER1 = AUC[TISF]TAD/ AUC[Serum]IVAD | 8.83 | 7.64 | 6.94 |
| ER2 = AUC[Serum]TAD/ AUC[Serum]IVAD | 0.44 | 0.44 | 0.89 |
| ER = ER1/ER2 = AUC[TISF]TAD/ AUC[Serum]TAD | 20 | 17.2 | 7.83 |
| MET | | | |
| Metronidazole TAD dose (mg) | 500 mg in 100 ml | 600 mg in 1200 ml | 200 mg IVAD + 400 mg/2 L TAD |
| [Metronidazole] Conc. in TAD | 413 mg/L | 172 mg/L | 200 mg/L |
| Metronidazole IVADdose (mg) | 500 mg | 600 mg | |
| AUC[TISF]TAD | 2595 | 1032 | 853 |
| AUC[Serum]TAD | 67 | 81 | 114.6 |
| AUC[Serum]IVAD | 121.9 | 127 | 127 |
| ER1 = AUC[TISF]TAD/ AUC[Serum]IVAD | 21.3 | 8.13 | 6.72 |
| ER2 = AUC[Serum]TAD/ AUC[Serum]IVAD | 0.55 | 0.64 | 0.9 |
| ER3 = ER1/ER2 = AUC[TISF]TAD/ AUC[Serum]TAD | 38.8 | 12.7 | 7.45 |

Results

FIGS. 9-14 illustrate the differences between TAD and IVAD in terms of the cumulative exposure (AUC) in serum and subcutaneous tumescent interstitial fluid (TISF).

As shown in FIG. 9A, cefazolin (1 gm total dose) at a concentration of 900 mg/L in TAD solution resulted in an AUC of cefazolin within TISF after TAD which was 16.5 times greater than the AUC in serum after delivery of 1 gm cefazolin by IVAD. Cefazolin (1 gm total dose) at a concentration of 450 mg/L in TAD solution resulted in an AUC in TISF after TAD which was 7.2 times greater than the AUC in serum after delivery of 1 gm cefazolin by IVAD. As shown in FIG. 9B, the AUC of cefazolin in serum after TAD are 0.76 and 0.34 times less than the AUC in serum after IVAD. Beyond 6 to 8 hours, serum cefazolin concentrations after TAD exceeded serum concentration after IVAD. Lower serum AUC after TAD is thus expected to result in less cumulative cefazolin exposure in well perfused tissues, such as the gut, than IVAD.

As shown in FIG. 10A, cefazolin (500 mg total dose) at a concentration of 225 mg/L in TAD solution and cefazolin (1 gm total dose) at a concentration of 450 mg/L in TAD solution resulted in AUC[TISF]TAD which are 12.8 and 17 times greater than AUC[Serum]IVAD, the cefazolin exposure in serum after delivery of 1 gm cefazolin by IVAD. As shown in FIG. 10B, TAD yields an exposure to cefazolin in serum (AUC[Serum]AD) which is 0.92 and 1.93 times less than the exposure to cefazolin in serum after IVAD (AUC[Serum]IVAD). Suggesting that depending on the concentration of antibiotic in the TAD solution, TAD may yield less or more cumulative exposure to cefazolin in the gut than IVAD. The rate of absorption of cefazolin from TISF into serum observed after TAD to the breasts was less than that observed for TAD to the abdomen or the hips and outer thighs.

As shown in FIG. 11A, total doses of 870 mg cefazolin and 435 mg cefazolin administered by TAD at 228 mg/L in the TAD solutions yielded AUC[TISF]TAD which are approximately equal and 4.42 and 4.92 times greater than AUC[Serum]IVAD after administration of 1 gm cefazolin by IVAD. This suggests that AUC[TISF]TAD is determined by the mg/L concentration of cefazolin in the TAD solution. As shown in FIG. 11B, TAD yields AUC[Serum]TADs which are 0.66 and 0.24 times less than AUC[Serum]IVAD.

The cumulative cefazolin exposure in serum after TAD appears to depend on the total mg dose, rather than concentration, of cefazolin in the TAD solution. Serum cefazolin concentration after 1 gm IVAD and after 870 mg TAD exceed 10 µg/ml for 6 and 10 hours, respectively.

As shown in FIG. 12A, total doses of 500 mg each of cefazolin and metronidazole administered by tumescent infiltration in 1211 ml TAD solution (413 mg/L) produced nearly identical concentrations in TISF. Consequently, the AUC[TISF]TAD values for cefazolin and metronidazole are also nearly identical. However, the ratio of the cumulative exposure to cefazolin and metronidazole in TISF following TAD, relative to the cumulative exposure to cefazolin and metronidazole in serum following IVAD (AUC[TISF]TAD/AUC[Serum]IVAD) equaled 8.83 and 21.3 respectively. This incongruity is attributable to the differences the values of the denominators, AUC[Serum]IVAD, for cefazolin and metronidazole, which were 292 and 122, respectively, after identical 500 mg doses by IVAD. These difference in AUC [Serum]IVAD are in turn attributable to the difference in the volume of distribution of each antibiotic. As shown in FIG. 12B, despite equal 500 mg IVAD doses of cefazolin and metronidazole, the respective Cmax in serum and AUC in serum differ significantly. This difference is attributable to differences between the antibiotics in tissue binding and in volume of distribution. After equal doses of metronidazole by TAD or IVAD, the serum concentrations of metronidazole are essentially identical from 8 hours and beyond.

FIG. 13A shows sequential cefazolin concentrations in: 1) TISF after administration of 1.2 gm cefazolin by TAD at 345 mg/L in the TAD solution; 2) serum after administration of 1.2 gm cefazolin by IVAD; and 3) TISF and serum after simultaneous administration of 800 mg cefazolin by TAD at 400 mg/L and by IVAD (400 mg). The resulting cumulative exposures to cefazolin in TISF after TAD, AUC[TISF]TAD, are 7.64 and 6.94 times greater than the AUC[Serum]IVAD, the cefazolin exposure in serum after administration of 1.2 gm cefazolin by IVAD. This demonstrates that the mg/L concentration of an antibiotic in the TAD solution largely determines the AUC[TISF]TAD. As shown in FIG. 13B, after IVAD of 1200 mg, the serum concentration of cefazolin only exceeds 10 µg/ml from 0 to 4 hours. After TAD of 1200 mg at 345 mg/L, the serum concentration of cefazolin only exceeded 10 µg/ml from 2 to 14 hours. After IVAD 400 mg plus TAD of 800 mg at 400 mg/L, the serum concentration of cefazolin exceeded 10 µg/ml from 0 to 12 hours. Thus, a combination of TAD and IVAD can eliminate any insufficiencies of either IVAD or TAD alone.

FIG. 14A shows sequential metronidazole concentrations in: 1) TISF after administration of 600 mg metronidazole by TAD at 172 mg/L in TAD solution; 2) serum after administration of 600 mg metronidazole by IVAD; and 3) TISF and serum after simultaneous administration of 400 mg metronidazole by TAD at 200 mg/L in TAD solution and 200 mg by IVAD. The resulting cumulative exposures to metronidazole in TISF after TAD (AUC[TISF]TAD), are 8.13 and 6.72 times greater than the metronidazole exposure in serum after administration of 600 mg metronidazole by IVAD (AUC[Serum]IVAD). This demonstrates that the AUC[TISF]TAD is largely determined by the concentration of an antibiotic in TAD solution. As shown in FIG. 14B, after IVAD of 600 mg, the serum concentration of metronidazole only exceeds 4 µg/ml from 0 to 12 hours. After TAD of 400 mg at 200 mg/L and IVAD of 200 mg, the serum concentration of metronidazole exceeded 4 µg/ml from 0 to 12 hours. After IVAD 200 mg plus TAD of 400 mg at 200 mg/L, the serum concentration of metronidazole exceeded 4 µg/ml from 0 to 16+hours. Thus, a combination of TAD and WAD can eliminate any insufficiencies of either IVAD or TAD alone.

Taken together, the graphs of linear concentration-scale in FIGS. 9A, 10A, 11A, 12A, 13A and 14A show an exponential rate of elimination of antibiotic from serum after IVAD, while the rate of elimination from both serum and TISF after TAD is a nearly constant or straight-line rate of elimination. For IVAD, the concentration of antibiotic in serum and in well-perfused tissues are in dynamic equilibrium with each other, therefore serum and ISF can be expected to follow the similar rates of elimination following IVAD. The exponential rate of elimination of antibiotic from serum after IVAD implies that the rate of elimination can be represented by a first order differential equation, which depends on the concentration (mg/ml) of the drug in serum as a function of time. The straight line decline of concentration (constant rate of elimination) over time observed in serum and TISF after TAD implies that the rate of elimination can be represented by a zero-order differential equation. A constant rate of elimination depends only on the total amount of drug in the TISF and is independent of the concentration (mg/ml) of the drug in TISF.

Graphs of log concentration-scale presented in FIGS. 9B, 10B, 11B, 12B, 13B and 14B allows for simultaneous visualization of lower concentrations of antibiotics in serum after TAD, the intermediate concentrations in serum after IVAD as well as the higher concentrations of antibiotic in TISF after TAD.

The Cmax in serum after IVAD always exceeded Cmax in serum after TAD. Because of its exponential decline after IVAD, the serum cefazolin concentration is essentially zero after 10 to 12 hours. On the other hand, beginning at about 6 hours after TAD or IVAD and continuing for the duration of the studies, serum cefazolin concentrations were uniformly greater after TAD compared concentrations of cefazolin after IVAD.

Cmax in serum after TAD is determined by the total mg-dose of antibiotic contained within the TAD solution. The total length of time that serum concentration of an antibiotic exceeds a given MIC can be greater for TAD than for IVAD. This may have implications for re-dosing requirements during prolonged surgical procedures. After rapid dosing by IVAD, the Cmax in serum is achieved immediately accompanied by a rapid exponential fall in serum concentration. After TAD, however, the profound widespread vasoconstriction results in prolonged slow systemic antibiotic absorption. After TAD, the antibiotic concentration in serum over time resembles a constant slow IV infusion over several hours. Hence, after TAD the serum concentration rises steadily and achieves a prolonged plateau with a relatively low Cmax and then falls slowly.

At equal antibiotic doses, the AUC, Cmax and T>MIC after IVAD can be significantly different from the AUC, Cmax and T>MIC after TAD. In TSIF, the AUC, Cmax and T>MIC after TAD was always observed to be greater than the AUC, Cmax and T>MIC after IVAD. Thus, TAD is expected to be more effective than IVAD in preventing surgical incision site infections. In serum, however, the relative values of AUC, Cmax and T>MIC depended on the mode of delivery. For example, the Cmax following IVAD always exceeded the Cmax after TAD in serum, while the AUC in serum following IVAD or TAD are, at least theoretically, approximately equal.

When comparing equal doses of antibiotic administered by IVAD and TAD, the relative advantages of IVAD and TAD, in terms of T>MIC, depend on the value of MIC. If MIC is greater than the Cmax[serum] after both IVAD and TAD then (T>MIC)=0 for both IVAD and TAD. If MIC is less than Cmax[serum] after WAD but MIC is greater than Cmax[serum] after TAD, then (T>MIC)=0 in serum after TAD and T>MIC in serum after IVAD is always greater 0. If MIC is less than Cmax[serum] after both IVAD and TAD, then the relative magnitudes of T>MIC in serum after WAD or TAD depend on the magnitude of MIC relative the magnitudes of Cmax in serum for IVAD and TAD. For example, if MIC is significantly less than Cmax[serum] for both IVAD and TAD, then, because of the concentration plateau in serum after TAD, it is likely that the duration T>MIC is greater for TAD than for IVAD. At equal doses of antibiotic, the situation where Cmax[serum] after IVAD is less than Cmax[serum] after TAD would not occur.

Within TISF at a surgical incision site, with equal doses of cefazolin given by IVAD or by TAD, and with approximately 1 gm cefazolin/L in TAD solution, pharmacokinetic analysis suggests that: 16 is less than AUC[TISF]TAD/AUC[Serum]IVAD which is less than AUC[TISF]TAD/AUC[ISF]IVAD; and 5.6 is less than Cmax[TISF]TAD/Cmax[Serum]IVAD which is less than Cmax[TISF]TAD/Cmax[ISF]IVAD.

Within serum, or equivalently, within the highly perfused gut, where [Serum]IVAD=[ISF(gut)]IVAD, pharmacokinetic analysis suggests that: 0.75 is less than AUC[Serum]TAD/AUC[Serum]IVAD, which is equal to AUC[Serum]TAD/AUC[ISF(gut)]IVAD; and 0.14 is less than Cmax[Serum]TAD/Cmax[Serum]IVAD which is equal to Cmax[Serum]TAD/Cmax[ISF(gut)]IVAD.

The clinical pharmacokinetic studies further demonstrated that immediately after IVAD of 1200 mg of cefazolin and 600 mg of metronidazole, peak serum concentrations are 152 µg/ml and 14 µg/ml, respectively, and decrease exponentially to 75 µg/ml and 11 µg/ml within one hour. At the conclusion of TAD of 1200 mg of cefazolin and 600 mg of metronidazole, the respective TISF concentrations are 1000 µg/ml of cefazolin and 600 µg/ml of metronidazole, which exceed the peak IVAD serum concentrations of 152 µg/ml cefazolin and 14 µg/ml metronidazole for 8 hours or more.

DISCUSSION

With rapid IVAD, the absorption of cefazolin and metronidazole is essentially instantaneous. The exponential decline of the serum concentrations of cefazolin and metronidazole with approximate log-linear elimination after IVAD indicates that the rate of antibiotic elimination from serum is dependent on antibiotic concentration in serum. These observations are consistent with first-order absorption kinetics and a one-compartment model. See FIGS. 13A and 14A. After TAD, however, the rates of absorption of cefazolin and metronidazole from subcutaneous tumescent interstitial fluid (TISF) into serum are dependent on the total milligram dose of the antibiotic. The approximate straight line graph of antibiotic concentration within the subcutaneous TISF as a function of time indicates the rate of elimination from TISF is nearly constant and independent antibiotic concentration in TISF, which is consistent with zero-order absorption kinetics. Further, after TAD the Cmax within TISF is essentially equal to the concentration of the antibiotic within the TAD solution. See FIG. 15. Thus, any desired Cmax (mg/ml) of an antibiotic within TISF at a surgical site can easily be achieved simply by formulating the TAD solution to contain at least that concentration.

The results of the clinical investigation of pharmacokinentic properties of TAD and WAD, demonstrate the superiority of TAD with respect to AUC, Cmax and T>MIC over IVAD for prevention of SSI.

Further, in obese patients, TAD is expected to be more effective than IVAD at preventing SSI. For example, studies have shown that the degree of antibiotic penetration (P) into subcutaneous ISF after IVAD (defined as P=AUC[ISF]IVAD/AUC[SERUM]IVAD) is less than 0.1 in 8/10 obese subjects and 3/10 normal controls. Toma O, Suntrup P, Stefanescu A, London A, Mutch M, Kharasch E. Pharmacokinetics and tissue penetration of cefoxitin in obesity: Implications for risk of surgical site infection. Anesth Analg 113:730-737, 2011. Thus, clinically significant percentages of normal and obese patients have a cefoxitin penetration less than 10% (10× AUC[ISF]IVAD<AUC[SERUM]IVAD). Our data regarding cefazolin shows that, at equal mg-doses, the AUC[Serum]IVAD is approximately 15 times less than the AUC[TISF]TAD (15×AUC[SERUM]IVAD<AUC[TISF]TAD). The protein binding of cefoxitin and cefazolin are approximately 72% and 70%-80%, respectively. Based on the fact that cefazolin and cefoxitin have similar protein binding (72% and 70%-80%, respectively) and similar volumes of distribution, it can be reasoned that they have similar penetration ratios. Based on this assumption, inequalities in tissue penetration in obese patients and protein binding antibiotic can be combined, to give 150× AUC[ISF]IVAD<AUC[TISF]TAD. Thus, for cefoxitin and cefazolin, TAD is expected to provide 150 times greater antibiotic exposure in ISF than WAD. Accordingly, TAD is expected to be more effective than IVAD at preventing SSI, especially in obese patients.

In addition, antibacterial effect of aminoglycoside antibiotics is best correlated with Cmax. The pharmacokinetic studies demonstrate that when equal antibiotic doses of antibiotic are given by IVAD and TAD, Cmax[ISF]IVAD<Cmax[TISF]TAD over many hours. Thus, for aminoglycoside antibiotics, TAD is expected to be superior to IVAD in preventing subcutaneous SSI.

Further, the results of the pharmacokinetic studies show that the time T[ISF]WAD>MIC, is always less than T[TISF]TAD>MIC for any given MIC. The antimicrobial effect of β-lactam antibiotics such as cefazolin on susceptible bacteria is best correlated with T>MIC. Thus for β-lactam antibiotics TAD is superior to IVAD at preventing SSL Accordingly, TAD is expected to be more effective than IVAD for preventing superficial and deep incisional SSL TAD requires slightly more time, different equipment and new clinical skills compared to WAD. However from the perspective of those concerned with surgical quality improvement, TAD represents an opportunity to substantially reduce the incidence of SSI.

For GI surgery, optimal antibiotic SSI prophylaxis requires adequate antibiotic concentrations in cutaneous and intra-peritoneal tissues. For contaminated or dirty colorectal surgery it may be advantageous to use a combination of TAD and IVAD. For non-GI surgeries, however, TAD alone may be superior to IVAD.

Intraoperative contamination of the surgical incision site is the cause of SSI and virtually all bacteria associated with SSI are extracellular pathogens. Successful antibiotic prophylaxis of SSI requires bactericidal concentrations of antibiotic within the contaminated interstitial fluid (ISF) of incised tissue. IVAD reliably achieves sufficient antibiotic concentrations in well perfused tissues. However, the transfer of antibiotic from blood into the ISF of surgically traumatized tissue is impaired by interruption of vascular supply, capillary thrombosis, edema, tissue desiccation, capillary vasoconstriction, hemorrhage and hypotension with slowing of capillary blood flow. Further, as described above, obese patients have impaired tissue penetration and IVAD provides inadequate antibiotic concentration within surgically traumatized subcutaneous tissue. Thus, WAD does not always achieve adequate antibiotic concentrations in peri-incisional tissue because of the confounding pathophysiology of surgically traumatized tissue in very ill patients with complex comorbidities.

Adequate antibiotic concentrations in serum does not guarantee adequate antibiotic concentrations in subcutaneous interstitial fluid [ISF] due to inadequate penetration of an antibiotic into subcutaneous interstitial fluid (ISF) from the serum. Penetration (P), expressed as P=AUC[ISF]IVAD/AUC[Serum]IVAD, is a measure of the cumulative exposure to an antibiotic within subcutaneous interstitial fluid (ISF) after IVAD compared to the exposure within serum after IVAD. In general, Penetration is less than or equal to 1 and can vary widely from patient to patient depending on several factors including the patient's degree of obesity. For example, when subcutaneous ISF cefoxitin is measured by microdialysis, among morbidly obese patients P=0.05±0.04 (range 0.02 to 0.1), in obese patients P=0.11±0.08 (range 0.02 to 0.22) and in normal weight volunteers PR=0.37±0.26 (range 0.04 to 0.7). Thus, among obese patients the degree of antibiotic penetration into ISF is only 22% that of normal weight subjects. It is incorrect to assume that if serum antibiotic concentrations are adequate in terms of T>MIC, then the resulting ISF antibiotic concentrations will also be adequate.

In addition, AUC(ISF)IVAD, the cumulative exposure to an antibiotic within subcutaneous ISF after IVAD, is not only a function of the total mg dose given by IVAD but it is also a random variable with a large statistical variance. For any group of patients, there is no dose of the antibiotic given by IVAD which will guarantee that all patients will achieve an AUC(ISF)IVAD sufficient to prevent an SSI. In other words, no matter how large an IVAD dose of antibiotic, there is a finite likelihood that 10% or more of patients will not achieve an insufficient AUC(ISF)IVAD for effective SSI prophylaxis. TAD, on the other hand, is a reliable mode of antibiotic delivery that allows for control of ISF antibiotic concentration at an incision site. Further, with TAD the antibiotic is delivered directly into the targeted tissue. Increasing concern about bacterial antibiotic resistance associated with antibiotic SSI prophylaxis has focused on both killing bacteria in situ and preventing survival of antibiotic resistant subpopulations. TAD may reduce the exposure of gut bacteria to antibiotics. Accordingly, TAD is superior to IVAD for SSI prevention.

What is claimed is:

1. A method of subcutaneous delivery of a drug or a therapeutic agent to a subject to treat a localized condition, the method comprising:
  (a) preparing a liquid composition consisting of the drug or the therapeutic agent dissolved in a tumescent solution, wherein the tumescent solution consists of a local anesthetic, a vasoconstrictor and a pharmaceutically acceptable carrier, and
  (b) delivering a mass of the liquid composition subcutaneously to a localized tissue in the subject, wherein the drug or the therapeutic agent treats the localized condition in the localized tissue,
  wherein a concentration of the drug or the therapeutic agent subcutaneously delivered exceeds a concentration of the drug or the therapeutic agent that can be safely achieved by intravenous delivery, and wherein an amount of the drug or the therapeutic agent located at an outer boundary of the mass of fluid and available for absorption is less than an amount of the drug or the therapeutic agent located within a central portion of the mass of fluid and virtually isolated from the systemic circulation by virtue of capillary vasoconstriction,
  wherein the localized condition is selected from the group consisting of a tumor, surgical site infection, chronic post-operative pain, risk of deep vein thrombosis, risk of post-operative thromboembolism and a burn wound.

2. The method of claim 1, wherein the vasoconstrictor component comprises epinephrine.

3. The method of claim 2, wherein the concentration of epinephrine is approximately 0.2 to 1.5 mg per L.

4. The method according to claim 1, wherein the drug or the therapeutic agent is an antibiotic.

5. The method of claim 4, wherein the antibiotic component comprises cefazolin.

6. The method of claim 4, wherein the antibiotic component comprises a mixture of two or more antibiotics.

7. The method of claim 1, wherein the composition further comprises an anti-inflammatory agent.

8. The method of claim 1, wherein the local anesthetic comprises lidocaine.

9. The method of claim 8, wherein the concentration of lidocaine is approximately 1,500 mg to 2,500 mg per L of solution.

10. The method according to claim 1 wherein the drug or therapeutic agent is a chemotherapeutic agent.

11. The method according to claim 1, used in the context of an emergency resuscitation where insertion of an IV catheter into a vein cannot be readily achieved.

12. The method according to claim 1, the subject is treated for an acute trauma or burn wound in a civilian or a military situation wherein access for intravenous delivery of fluids is not possible.

13. The method according to claim 1, wherein the subject is an obese patient in which finding an accessible vein for IV access is difficult.

14. The method of claim 1, comprising making an incision through the skin into the subcutaneous tissue of the patient and/or removal of subcutaneous tissue from the patient.

15. The method according to claim 1, wherein the mass of fluid comprising the tumescent composition is administering into a subcutaneous fat compartment.

16. The method according to claim 1, wherein the mass of fluid comprising the tumescent composition is administered to the subject by tumescent delivery to a subcutaneous compartment of a surgical site in a subject undergoing a surgical procedure, wherein a risk of surgical site infection in the subject is thereby reduced.

17. The method of claim 1, wherein the chemotherapy agent comprises adriamycin.

18. The method of claim 1, wherein the angiogenesis inhibitor comprises angiostatin.

19. A method of subcutaneous delivery of a drug or a therapeutic agent to a subject to treat a localized condition, the method comprising:
  (a) providing a liquid composition consisting of the drug or the therapeutic agent dissolved in a tumescent solution, wherein the tumescent solution consists of a vasoconstrictor and a pharmaceutically acceptable carrier, and
  (b) delivering a mass of the liquid composition subcutaneously to a localized tissue in the subject, wherein the drug or the therapeutic agent treats the localized condition in the localized tissue, wherein a concentration of the drug or the therapeutic agent subcutaneously delivered exceeds a concentration of the drug or the therapeutic agent that can be safely achieved by intravenous delivery, and wherein an amount of the drug or the therapeutic agent located at an outer boundary of the mass of fluid and available for absorption is less than an amount of the drug or the therapeutic agent located within a central portion of the mass of fluid and virtually isolated from the systemic circulation by virtue of capillary vasoconstriction, and wherein the localized condition is selected from the group consisting of a tumor, surgical site infection, chronic post-operative pain, risk of deep vein thrombosis, risk of post-operative thromboembolism and a burn wound.

* * * * *